(12) United States Patent
Snow et al.

(10) Patent No.: US 6,563,016 B1
(45) Date of Patent: May 13, 2003

(54) PERLECAN TRANSGENIC ANIMALS AND METHODS OF IDENTIFYING COMPOUNDS FOR THE TREATMENT OF AMYLOIDOSES

(75) Inventors: Alan D. Snow, Lynnwood, WA (US); Ken-Ichiro Fukuchi, Birmingham, AL (US); John Hassell, Tampa, FL (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 09/536,231

(22) Filed: Mar. 27, 2000

Related U.S. Application Data

(63) Continuation of application No. 08/870,987, filed on Jun. 6, 1997, now abandoned.
(60) Provisional application No. 60/017,830, filed on Jun. 6, 1996.

(51) Int. Cl.[7] ..................... A01K 67/00; A01K 67/027; C12N 15/00; C12N 5/00
(52) U.S. Cl. ................... 800/12; 800/8; 800/9; 800/3; 800/14; 800/18; 800/21; 800/22; 800/25; 435/320.1; 435/325; 435/455
(58) Field of Search .................. 800/3, 12, 14, 800/18, 21, 22, 8, 9, 25; 435/320.1, 325, 455; 536/23.1, 23.5

(56) References Cited

U.S. PATENT DOCUMENTS

| | | |
|---|---|---|
| 5,672,805 A | 9/1997 | Neve ............................. 800/2 |
| 5,811,633 A | 9/1998 | Wadsworth et al. ........... 800/2 |

FOREIGN PATENT DOCUMENTS

| | | |
|---|---|---|
| CA | 2135595 | 5/1995 |

OTHER PUBLICATIONS

Wall RJ Theriogenology 45:57–68, 1996.*
Pursel VG et al J. Reprod Fert. Sup 40: 235–245 1990.*
Kappel et al. Current Opinion in Biotechnology 3:548–553 1992.*
Viville, in Transgenic Animals, Houdebine (eds), Harwood academic publishers, France. pp307–321, 1997.*
Lannfelt et al, Behav. Brain Res. 57(2):207–213, 1993.*
Podlisny et al Neurobiol Aging 13(5)561–7, 1992.*
Lamb BT et al Nature Genetics 5:22–29, 1993.*
Sandhu et al J Biol Chem 266(32):21331–4, Nov. 15, 1991.*
Noonan et al J Bio. Chem. 266(34):22939–47, 1991.*
Aillies et al Lab. Invest. 69(4):443–448, 1993.*
Sponaas et al Int. Immnol. 6(2):277–287 1994.*
Couchman et al., Perlecan and basement membrane–chrondroitin sulfate proteoglycan (Bamacan) are two basement membrane chondroitin/dermatan sulfate proteoglycans in the engelbreth–holm–swarm tumor matrix, 1996, The J Of Biol.Chem., vol. 271, pp. 9595–9602.*

Chakravarti et al., Recombinant Domain III of perlecan promotes cell attachment through it's RGDS sequence, 1995, The Journal Of Biological Chemistry, vol. 270, pp. 404–409.*
kokenyesi et al., Formation of heparan sulfate or chrondroitin/dermatan sulfate on recombinant domain I of mouse perlecan expressed in chinese hamster ovary cells, 1995, Biochemical And Biophysical Research Communications, vol. 211, pp. 262–267.*
Sekiguchi et al., Characterization of proteoglycans synthesized by murine embryonal carcinoma cells (P19) reveals increased expression of perlecan (heparan sulfate proteoglycan) during neuronal differentiation, 1994, J Neurosci Res. , vol. 38, pp. 670–686.*
Cohen et al. "Structural Characterization of the Complete Human Perlecan Gene and Its Promoter," Proceedings of the National Academy of Sciences (USA), vol. 90, pp. 10404–10408 (especially 10405–10406), Nov. 1993.
Ailles et al. "Induction of Perlecan Gene Expression Precedes Amyloid Formation During Experimental Murine AA Amyloidogenesis," Laboratory Investigation, vol. 69, No. 4, pp. 443–448 (especially 445–446), 1993.
Noonan et al. "The Complete Sequence of Perlecan, a Basement Membrane Heparan Sulphate Prteoglycan, Reveals Extensive Similarity with Laminin A Chain, Low Density Lipoprotein–Receptor, and the Neural Cell Adhesion Molecule," Journal of Bio. Chem., vol. 266, No. 34, pp. 22939–22947 (especially 22941–22943), Dec. 5, 1991.
Maresh et al. "Detection and Quantitation of Perlecan mRNA Levels in Alzheimer's Disease and Normal Aged Hippocampus by Competitive Reverse Transcription–Polymerase Chain Reaction," Journal of Neurochemistry, vol. 67, No. 3, pp. 1132–1144, 1996.

(List continued on next page.)

*Primary Examiner*—Scott D. Priebe
*Assistant Examiner*—Sumesh Kaushal
(74) *Attorney, Agent, or Firm*—Patrick M. Dwyer

(57) ABSTRACT

The invention provides a transgenic non-human animal expressing a perlecan encoding transgene. Also provided is a double-transgenic non-human animal expressing a perlecan and a amyloid encoding transgene. A method of screening for a compound which alters the rate or extent of amyloid deposition is additionally provided. The method consists of: (a) constructing a perlecan transgenic animal; (b) administering an effective amount of a test compound to said perlecan transgenic animal; and (c) determining whether said test compound alters the extent or rate of amyloid deposition. Finally, the invention provides a method of screening for a compound which alters the rate or extent of amyloid deposition. The method consists of: (a) constructing a perlecan/amyloid double-transgenic animal; (b) administering an effective amount of a test compound to said perlecan/amyloid double-transgenic animal; and (c) determining whether said test compound alters the extent or rate of amyloid deposition.

2 Claims, 25 Drawing Sheets

OTHER PUBLICATIONS

Fukuchi et al. "Increased Expression of β–Amyloid Protein Precursor and Microtubule–Associated Protein τ During the Differentiation of Murine Embryonal Carcinoma Cells," Journal of Neurochemistry, vol. 58, No. 5, pp. 1863–1873, 1992.

Sekiguchi et al. "Rapid Communications: Characterization of Proteoglycans Synthesized by Murin Embryonal Carcinoma Cell (P19) Reveals Increased Expression of Perlecan (Heparan Sulfate Proteoglycan) During Neuronal Differentiation," Journal of Neuroscience Research, vol. 38, pp. 670–686, 1994.

Miller et al. "Localization of Perlecan (or a Perlecan–Related Macromolecule) to Isolated Microglia In Vitro and to Microglia/Macrophages Following Infusion of Beta–Amyloid Protein Into Rodent Hippocampus," GLIA, vol. 21, pp. 228–243, 1997.

Castillo et al. "Novel Purification and Detailed Characterization of Perlecan Isolated from the Engelbreth–Holm–Swarm Tumor fo Use in an Animal Model of Fibrillar Aβ Amyloid Persistence in Brain," Journal of Biochemistry, vol. 120, No. 2 pp. 433–444, 1996.

Snow et al. "Immunolocalization of Heparan Sulfate Proteoglycans to the Prion Protein Amyloid Plaques of Gerstmann–Straussler Syndrome, Creutzfeldt–Jakob Disease and Scrapie," Laboratory Investigation, vol. 63, No. 5, pp. 601–611, 1990.

Kammesheidt et al. "Deposition of β/A4 Immunoreactivity and Neuronal Pathology in Transgenic Mice Expressing the Carboxyl–terminal Fragment of the Alzheimer and Amyloid Precursor in the Brain," Proc. Nat. Acad. Sci. USA, vol. 89, pp. 10857–10861, Nov. 1992.

Schmidt et al. "The Cytomegalovirus Enhancer: a Pan–Active Control Element in Transgenic Mice," Molecular and Cellular Biology, vol. 10, pp. 4406–4411, Aug. 1990.

Castillo et al. "Perlecan Binds to the β–Amyloid Proteins (Aβ) of Alzheimer's Disease, Accelerates Aβ Fibril Formation, and Maintains Aβ Fibril Stability," Journal of Neurochemistry, vol. 69, No. 6, pp. 2452–2465, 1997.

Snow et al. "An Important Role of Heparan Sulfate Proteoglycan (Perlecan) in a Model System for teh Deposition and Persistence of Fibrillar Aβ–Amyloid in Rat Brain," Nerron, vol. 12, pp. 219–234, Jan. 1994.

Snow et al. "The Presence of Heparan Sulfate Proteoglycans in the Neuritic Plaques and Congophilic Angiopathy in Alzheimer's Disease," American Journal of Pathology, vol. 133, No. 3, pp. 456–463, Dec. 1988.

Snow et al. "Specific Proteoglycans as Potential Causative Agents and Relevant Targets for Therapeutic Intervention in Alzheimer's Disease and Other Amyloidoses," Amyloid: Int. J. Exp. Clin. Invest., vol. 4, pp. 135–141, 1997.

Kallunki et al. "Human Basement Membrane Haparan Sulfate Proteoglycan Core Protein: A 467–kD Protein Containing Multiple Domains Resembling Elements of the Low Density Lipoprotein Receptor, Laminin, Neural Cell Adhesion Molecules, and Epidermal Growth Factor," The Journal of Cell Biology, vol. 116, pp. 559–571, 1992.

Murdoch et al. "Primary Structure of the Human Heparan Sulfate Proteoglycan from Basement Membrane (HSPG2/Perlecan)," Journal of Bio. Chem., vol. 267, No. 12, pp. 8544–8557, Apr. 25, 1992.

Kato et al. "Basement Membrane Proteoglycan in Various Tissues: Characterization Using Monoclonal Antibodies to the Engelbreth–Holm–Swarm Mouse Tumor Low Density Heparan Sulfate Proteoglycan," Journal of Cell Biology, pp. 2203–2210, Jun. 1988.

Dziadek et al. "Immunological Characterization of Basement Membrane Types of Heparan Sulfate Proteoglycan," EMBO Journal, vol. 4, No. 4, pp. 905–912, 1985.

Kinsella et al. "Structural Characterization of Heparan Sulfate Proteoglycan Subclasses Isolated from Bovine Aortic Endothelial Cell Cultures," Biochemistry, vol. 27, pp. 2136–2144, 1988.

Saku et al. "Characterization of the Major Heparan Sulfate Proteoglycan Secreted by Bovin Aortic Endothelial Cells in Culture," Journal of Bio. Chem., vol. 264, No. 6, pp. 3514–3523, Feb. 25, 1989.

Rescan et al. "Distribution and Origin of the Basement Membrane Component Perlecan in Rat Liver and Primary Hepatocyte Culture," American Journal of Pathology, vol. 142, No. 1, pp. 199–208, Jan. 1993.

Nikkari et al. "Smooth Muscle Cell Expression of Extracellular Matrix Genes after Arterial Injury," American Journal of Pathology, vol. 144, No. 6, pp. 1348–1356, Jun. 1994.

Murdoch et al. "Widespread Expression of Perlecan Proteoglycan in Basement Membranes and Extracellular Matrices of Human Tissues as Detected by a Novel Monoclonal Antibody Against Domain III and by In Situ Hybridization," Journal of Histochemistry and Cytochemistry, vol. 42, No. 2, pp. 239–249, 1994.

Heremans et al. "Matrix–associated Heparan Sulfate Proteoglycan: Core Protein–specific Monoclonal Antibodies Decorate the Pericellular Matrix of Connective Tissue Cells and the Stromal Side of Basement Membrane," Journal of Cell Biology, vol. 109, pp. 3199–3211, 1989.

Laemmli, U.K. "Cleavage of Structural Proteins during the Assembly of the Head of Bacteriophage T4," Nature, vol. 227, pp. 680–685, Aug. 15, 1970.

Elder et al. "Multiple Nuclear Factors Interact with the Promoter of the Human Neurofilament M Gene," Molecular Brain Research, vol. 15, pp. 99–107, 1992.

Potter, H. "The Involvement of Astrocytes and an Acute Phase Response in the Amyloid Deposition of Alzheime's Disease," Progress in Brain Research, vol. 94, pp. 447–458, 1992.

Palmiter et al. "MT–III, a Brain–specific Member of the Metallothionein Gene Family," Proc. Natl. Acad. Sci. USA, vol. 89, pp. 6333–6337, Jul. 1992.

Pursiner et al. "Transgenic Studies Implicate Interactions between Homologous PrP Isoforms in Scrapie Prion Replication," Cell, vol. 63, pp. 673–686, Nov. 16, 1990.

Scott et al. "Transgenic Mice Expressing Hamster Prion Protein Produce Species–specific Scrapie Infectivity and Amyloid Plaques," Cell, vol. 49, pp. 846–857, Dec. 1, 1989.

Hsiao et al. "Age–related CNS Disorder and Early Death in Transgenic FVB/N Mice Overexpressing Alzheimer Amyloid Precursor Proteins," Neuron, vol. 15, pp. 1203–1218, Nov. 1995.

Morris et al. "Specific Stimulation of Basal Lamina Heparan Sulfate Proteoglycan in Mouse Uterine Epithelium by Matrigel and by Transforming Growth Factor–β1," In Vitro Cell Dev. Biol., vol. 30A, pp. 120–128, Feb. 1994.

Ohji et al. "Basement Membrane Synthesis by Human Corneal Epithelial Cells In Vitro," Investigative Ophtalmoloygy & Visual Science, vol. 35, No. 2, pp. 479–485, Feb. 1994.

Van Det et al. "Proteoglycan Production by Human Glomerular Visceral Epithelial Cells and Mesangial Cells In Vitro," Biochem. Journal, vol. 307, pp. 759–768, 1995.

Dodge et al. "Expression of the Basement Membrane Heparan Sulfate Proteoglycan (Perlecan) in Human Synovium and in Cultured Human Synovial Cells," Laboratory Investigation, vol. 73, No. 5, pp. 649–657, 1995.

Grässel et al. "The Proteoglycan Perlecan is Expressed in the Erythroleukemia Cell Line K562 and Is Upregulated by Sodium Butyrate and Phorbol Ester," Molecular and Cellular Biology, vol. 145, pp. 61–68, 1995.

Cohen et al. "Abnormal Expression of Perlecan Proteoglycan in Metastatic Melanomas," Cancer Research, vol. 54, pp. 5771–5774, 1994.

Guelstein et al. "Myoepithelial and Basement Membrane Antigens in Benign and Malignant Human breast Tumors," Int. J. Cancer, vol. 53, pp. 269–277, 1993.

Chakravarti et al. "Perlecan Gene Expression Precedes Laminin Gene Expression During Differentiation of F9 Embryonal Carcinoma Cells," Developmental Dynamics, vol. 197, pp. 107–114, 1993.

Fukuchi et al. "Overexpression of a C–Terminal Portion of the β–Amyloid Precursor Protein in Mouse Brains by Transplantation of Transformed Neuronal Cells," Experimental Neurology, vol. 127, pp. 253–264, 1994.

Niwa et al. "Efficient Selection for High–expression Transfectants with a Novel Eukaryotic Vector," Gene, vol. 108, pp. 193–200, 1991.

Palmer et al. "Efficient Expression of a Protein Coding Gene Under the Control of RNA Polymerase I Promoter," Nucleic Acids Research, vol. 21, No. 15, pp. 3451–3457, 1993.

Mizushima et al. "pEF–BOS, a Powerful Mammalian Expression Vector," Nucleic Acids Research, vol. 18, No. 17, pp. 5322, 1990.

Ahearn et al. "Cloning and Sequence Analysis of the Mouse Genomic Locus Encoding the Largest Subunit of RNA Polymerase II," Journal of Bio. Chem., vol. 262, No. 22, pp. 10695–10705, Aug. 5, 1987.

Games et al. "Alzheimer–type Neuropathology in Transgenic Mice Overexpressing V717F β–Amyloid Precursor Protein," Nature, vol. 373, pp. 523–527, Feb. 9, 1995.

Sasahara et al. "PDGF B–Chain in Neurons of the Central Nervous System, Posterior Pituitary, and in a Transgenic Model," Cell, vol. 64, pp. 271–227, Jan. 11, 1991.

Begemann et al. "Expression of Chicken Liver Cell Adhesion Molecule Fusion Genes in Transgenic Mice," Proc. Natl. Acad. Sci. USA, vol. 87, pp. 9042–9046, Nov. 1990.

Balcarek et al. "Structure of the Mouse Glial Fibrillary Acidic Protein Gene: Implications for the Evolution of the Intermediate Filament Multigene Family," Nucleic Acids Research, vol. 13, No. 15, pp. 5527–5543, 1985.

Uchida et al. "The Growth Inhibitory Factor That Is Deficient in the Alzheimer's Disease Brain Is a 68 Amino Acid Metallothionein–like Protein," Neuron, vol. 7, pp. 337–347, Aug. 1991.

Sarvetnick et al. "Insulin–Dependent Diabetes Mellitus Induced in Transgenic Mice by Ectopic Expresson of Class II MHC and Interferon–Gamma," Cell, vol. 52, pp. 773–782, Mar. 11, 1988.

Petter et al. "Transgenic Mice Expressing β–Galactosidase in Mature Neurons under Neuron–specific Enolase Promoter Control," Neuron, vol. 5, pp. 187–197, Aug. 1990.

Quon et al. "Formation of β–Amyloid Protein Deposits in Brains of Transgenic Mice," Nature, vol. 352, pp. 239–241, Jul. 18, 1991.

Taiji et al. "Basic Fibroblast Growth Factor Enhances Nerve Growth Factor Receptor Gene Promoter Activity in Human Neuroblastoma Cell Line CHP100," Molecular and Cellular Biology, vol. 12, No. 5, pp. 2193–2202, May 1992.

Yi et al. "Systemic Amyloidosis in Transgenic Mice Carrying the Human Mutant Transthyretin (Met30) Gene," American Journal of Pathology, vol. 138, No. 2, pp. 403–412, Feb. 1991.

Fukuchi et al. "Overexpression of cDNAs for α–Amyloid Precursor Proteins 695, 751, and 770 Enhance the Secretion of β–Amyloid Precursor Protein Derivatives and the Survival of P19–Derived Neurons," Journal of Neurochemistry, vol. 66, No. 5, pp. 2201–2204, 1996.

Haass et al. "Cellular Processing of β–Amyloid Precursor Protein and the Genesis of Amyloid β–Peptide," Cell, vol. 75, pp. 1039–1042, Dec. 17, 1993.

Board Of Trustees Of The University Of Illinois "Transgenic Animal Models for Alzheimer's Disease," WIPO International Publication No. WO 94/242266, Oct. 27, 1994. (PCT/US94/042026, filed Apr. 12, 1994).

Athena Neurosciences, Inc. "Method for Identifying Alzheimer's Disease Therapeutics Using Transgenic Animal Models," WIPO International Publication No. WO 96/40895, Dec. 19, 1996. (PCT/US/09679, filed Jun. 7, 1996).

Trustees Of Columbia University In The City Of New York, "Identification of sel–12 and Uses Thereof," WIPO International Publication No. WO 97/11956, Apr. 3, 1997. (PCT/US96/15727, filed Sep. 27, 1996).

Cephalon, Inc. "Transgenic Animal Model for Alzheimer's Disease," WIPO International Publication No. WO 94/12627, Jun. 9, 1994. (PCT/US93/11480, filed Nov. 24, 1993).

California Biotechnology, Inc. "Transgenic Non–human Mammal displaying the Amyloid–forming Pathology of Alzheimer's Disease," WIPO International Publication No. WO 91/19810, Dec. 26, 1991. (PCT/US91/04447, filed Jun. 17, 1991).

Regents Of The University Of Minnesota "Transgenic Non–human Mammals with Progressive Neurologic Disease," WIPO International Publication No. WO 95/20666, Aug. 3, 1995. (PCT/US95/01088, filed Jan. 27, 1995).

Athena Neurosciences, Inc. "Transgenic Animals Harboring APP Allele Having Swedish Mutation," WIPO International Publication No. WO 95/11968, May 4, 1995. (PCT/US94/11827, filed Oct. 18, 1994).

Athena Neurosciences, Inc. "Method for Identifying Alzheimer's Disease Therapeutics Using Transgenic Animal Models," WIPO International Publication No. WO 96/40896, Dec. 19, 1996. (PCT/US96/09857, filed Jun. 7, 1996).

TSI Corporation "Transgenic Animal Models for Alzheimer's Disease," WIPO International Publication No. WO 93/14200, Jul. 22, 1993. (PCT/US92/11276, filed Dec. 29, 1992.

Hoechst Japan Limited "Transgenic Animal for Alzheimer's Disease," EPO Publication No. 0653154A2, Bulletin 95/20, May 17, 1995. (EPO Application No. 94117512.7, filed Nov. 7, 1994).

* cited by examiner

PERLECAN TRANSGENIC ANIMALS AND METHODS OF IDENTIFYING COMPOUNDS FOR THE TREATMENT OF AMYLOIDOSES

This is a continuation of Ser. No. 08/870,987 filed Jun. 6, 1997 now abandoned, which claims priority to Ser. No. 60/017,830 filed Jun. 6, 1996.

The invention relates to the overproduction of perlecan in transgenic animals and transfected animal cells as screening tools to identify lead therapeutics for the amyloid diseases.

BACKGROUND OF THE INVENTION

The Amyloid Diseases

The "amyloid diseases" consist of a group of clinically and generally unrelated human diseases which all demonstrate a marked accumulation in tissues of an insoluble extracellular substance known as "amyloid", and usually in an amount sufficient to impair normal organ function. Rokitansky in 1842 (Rokitansky, "Handbuch der pathologischen Anatomie", Vol. 3, Braumuller and Seidel, Vienna) was the first to observe waxy and amorphous looking tissue deposits in a number of tissues from different patients. However, it wasn't until 1854 when Virchow (Virchow, Arch. Path. Anat. 8:416 (1854)) termed these deposits as "amyloid" meaning "starch-like" since they gave a positive staining with the sulfuric acid-iodine reaction, which was used in the 1850's for demonstrating cellulose. Although cellulose is not a constituent of amyloid, nonetheless, the staining that Virchow observed was probably due to the present of proteoglycans (PGs) which appear to be associated with all types of amyloid deposits. The name amyloid has remained despite the fact that Friederich and Kekule in 1859 discovered the protein nature of amyloid (Friedrich and Kekule, Arch. Path. Anat. Physiol. 16:50 (1859)). For many years, based on the fact that all amyloids have the same staining and structural properties, lead to the postulate that a single pathogenetic mechanism was involved in amyloid deposition, and that amyloid deposits were thought to be composed of a single set of constituents. Current research has clearly shown that amyloid is not a uniform deposit and that amyloids may consist of different proteins which are totally unrelated (Glenner, N. England J. Med. 302:1283–1292 (1980)).

Although the nature of the amyloid itself has been found to consist of completely different and unrelated proteins, all amyloids appear similar when viewed under the microscope due to amyloid's underlying protein structure to adapt into a fibrillar structure. All amyloids regardless of the nature of the underlying protein 1) stain characteristically with the Congo red dye and display a classic red/green birefringence when viewed under polarized light (Puchtler et al, J. Histochem, Cytochem. 10:355–364 (1962)), 2) ultrastructurally consists of fibrils with a diameter of 7–10 nanometers and of indefinite length, 3) adopt a predominant beta-pleated sheet secondary structure. Thus, amyloid fibrils viewed under an electron microscope (30,000 times magnification) from the post-mortem brain of an Alzheimer's disease patient would look nearly identical to the appearance of amyloid present in a biopsied kidney from a rheumatoid arthritic patient. Both these amyloids would demonstrate a similar fibril diameter of 7–10 nanometers.

In the mid to late 1970's amyloid was clinically classified into 4 groups, primary amyloid, secondary amyloid, familial amyloid and isolated amyloid. Primary amyloid, is amyloid appearing de novo, without any preceding disorder. In 25–40% of these cases, primary amyloid was the antecedent of plasma cell dysfunction such as the development of multiple myeloma or other B-cell type malignancies. Here the amyloid appears before rather than after the overt malignancy. Secondary amyloid, appeared as a complication of a previously existing disorder. 10–15% of patients with multiple myeloma eventually develop amyloid (Hanada et al., J. Histochem. Cytochem. 19:1–15 (1971)). Patients with rheumatoid arthritis, osteoarthritis, ankylosing spondylitis can develop secondary amyloidosis as with patients with tuberculosis, lung abscesses and osteomyelitis (Benson and Cohen, Arth. Rheum. 22:36–42 (1979); Kamei et al., Acta Path. Jpn. 32:123–133 (1982); McAdam et al., Lancet 2:572–575 (1975)). Intravenous drug users who self-administer and who then develop chronic skin abscesses can also develop secondary amyloid (Novick, Mt. Sin. J. Med. 46:163–167 (1979)). Secondary amyloid is also seen in patients with specific malignancies such as Hodgkin's disease and renal cell carcinoma (Husby et al., Cancer Res. 42:1600–1603 (1982)). Although these were all initially classified as secondary amyloid, once the amyloid proteins were isolated and sequenced many of these turned out to contain different amyloid proteins.

The familial forms of amyloid also showed no uniformity in terms of the peptide responsible for the amyloid fibril deposited. Several geographic populations have now been identified with genetically inherited forms of amyloid. One group is found in Israel and this disorder is called Familial Mediterranean Fever and is characterized by amyloid deposition, along with recurrent inflammation and high fever (Mataxas, Kidney 20:676–685 (1981)). Another form of inherited amyloid is Familial Amyloidotic Polyneuropathy, and has been found in Swedish (Skinner and Cohen, Biochem. Biophys. Res. Comm. 99:1326–1332 (1981)), Portuguese (Saraiva et al., J. Lab. Clin. Med. 102:590–603 (1983); J. Clin. Invest. 74:104–119 (1984)) and Japanese (Tawara et al., J. Lab. Clin. Med. 98:811–822 (1981)) nationalities. Amyloid deposition in this disease occurs predominantly in the peripheral and autonomic nerves. Hereditary amyloid angiopathy of Icelandic origin is an autosomal dominant form of amyloid deposition primarily affecting the vessels in the brain, and has been identified in a group of families found in Western Iceland (Jennson et al., Clin. Genet. 36:368–377 (1989)). These patients clinically have massive cerebral hemorrhages in early life which usually causes death before the age of 40.

The primary, secondary and familial forms of amyloid described above tend to involve many organs of the body including heart, kidney, liver, spleen, gastrointestinal tract, skin, pancreas, and adrenal glands. These amyloid diseases are also referred to as "systemic amyloids" since so many organs within the body demonstrate amyloid accumulation. For most of these amyloidoses, there is no apparent cure or effective treatment and the consequences of amyloid deposition can be detrimental to the patient. For example, amyloid deposition in kidney may lead to renal failure, whereas amyloid deposition in heart may lead to heart failure. For these patients, amyloid accumulation in systemic organs leads to eventual death generally within 3 to 5 years.

Isolated forms of amyloid, on the other hand, tend to involve a single organ system. Isolated amyloid deposits have been found in the lung, and heart (Wright et al., Lab. Invest. 30:767–773 (1974); Pitkanen et al., Am. J. Path. 117:391–399 (1984)). Up to 90% of type II diabetic patients (non-insulin dependent form of diabetes) have isolated amyloid deposits in the pancreas restricted to the beta cells in the islets of Langerhans (Johnson et al., New Engl. J. Med. 321:513–518 (1989); Lab Invest 66:522–535 (1992)). Isolated forms of amyloid have also been found in endocrine tumors which secrete polypeptide hormones such as in medullary carcinoma of the thyroid (Butler and Khan, *Arch. Path. Lab. Med.* 110:647–649 (1986); Berger et al., *Virch. Arch. A Path. Anat. Hist.* 412:543–551 (1988)). A serious complication of long term hemodialysis is amyloid deposited in the medial nerve and clinically associated with carpal tunnel syndrome (Gejyo et al., *Biochem. Biophys. Res. Comm.* 129:701–706 (1985); *Kidney Int.* 30:385–390 (1986)). By far, the most common type and clinically relevant type of organ-specific amyloid, and amyloid in general, is that found in the brains of patients with Alzheimer's disease (see U.S. Pat. No. 4,666,829 and Glenner and Wong, *Biochem. Biophys. Res. Comm.* 120:885–890 (1984); Masters et al., *Proc. Natl. Acad. Sci. USA* 82:4245–4249 (1985)). In this disorder, amyloid is predominantly restricted to the central nervous system. Similar deposition of amyloid in the brain occurs in Down's syndrome patients once they reach the age of 35 years (Rumble et al., *New England J. Med.* 320:1446–1452 (1989); Mann et al., *Neurobiol. Aging* 10:397–399 (1989)). Other types of central nervous system amyloid deposition include rare but highly infectious disorders known as the prion diseases which include Creutzfeldt-Jakob disease, Gerstmann-Straussler syndrome, and kuru (Gajdusek et al., *Science* 197:943–960 (1977); Prusiner et al., *Cell* 38:127–134 (1984); Prusiner, *Scientific American* 251:50–59 (1984); Prusiner et al., *Micr. Sc.* 2:33–39 (1985); Tateishi et al., *Ann. Neurol.* 24:35–40 (1988)).

It was misleading to group the various amyloidotic disorders strictly on the basis of their clinical features, since when the major proteins involved were isolated and sequenced, they turned out to be different. For example, amyloid seen in rheumatoid arthritis and osteoarthritis, now known as AA amyloid, was the same amyloid protein identified in patients with the familial form of amyloid known as Familial Mediterranean Fever. Not to confuse the issue, it was decided that the best classification of amyloid should be according to the major protein found, once it was isolated, sequenced and identified.

Thus, amyloid today is classified according to the specific amyloid protein deposited. The amyloid diseases include, but are not limited to, the amyloid associated with Alzheimer's disease, Down's syndrome and hereditary cerebral hemorrhage with amyloidosis of the Dutch type (wherein the specific amyloid is now known as the beta-amyloid protein or Aβ), the amyloid associated with chronic inflammation, various forms of malignancy and Familial Mediterranean Fever (AA amyloid or inflammation-associated amyloidosis), the amyloid associated with multiple myeloma and other B-cell abnormalities (AL amyloid), the amyloid associated with type II diabetes (amylin or islet amyloid), the amyloid associated with the prion diseases including Creutzfeldt-Jakob disease, Gerstmann-Straussler syndrome, kuru and animal scrapie (PrP amyloid), the amyloid associated with long-term hemodialysis and carpal tunnel syndrome (beta$_2$-microglobulin amyloid), the amyloid associated with senile cardiac amyloid and Familial Amyloidotic Polyneuropathy (prealbumin or transthyretin amyloid), and the amyloid associated with endocrine tumors such as medullary carcinoma of the thyroid (variants of procalcitonin).

Although there are many different types of amyloid diseases as described above, there are only a few animal models for these diseases to develop new therapeutic agents. Inflammation-associated or AA amyloidosis has a well-defined experimental mouse model which is used to induce amyloid deposition in systemic organs such as spleen, liver and kidney (Snow and Kisilevsky, *Lab. Invest.* 53:37–44 (1985)). In addition, only some of the Alzheimer's disease neuropathology is observed in current animal models of the disease (described below). Thus, there is a need for the development of new transgenic animal models for the amyloid diseases including Alzheimer's disease. In addition, there is a need for new cell culture models to rapidly screen and identify new lead therapeutics for each of the amyloid diseases.

SUMMARY OF THE INVENTION

The invention provides a transgenic non-human animal expressing a perlecan encoding transgene. Also provided is a double-transgenic non-human animal expressing a perlecan and a amyloid encoding transgene. A method of screening for a compound which alters the rate or extent of amyloid deposition is additionally provided. The method consists of: (a) constructing a perlecan transgenic animal; (b) administering an effective amount of a test compound to said perlecan transgenic animal; and (c) determining whether said test compound alters the extent or rate of amyloid deposition. Finally, the invention provides a method of screening for a compound which alters the rate or extent of amyloid deposition. The method consists of: (a) constructing a perlecan/amyloid double-transgenic animal; (b) administering an effective amount of a test compound to said perlecan/amyloid double-transgenic animal; and (c) determining whether said test compound alters the extent or rate of amyloid deposition.

DETAILED DESCRITION OF THE INVENTION

Figure 1:
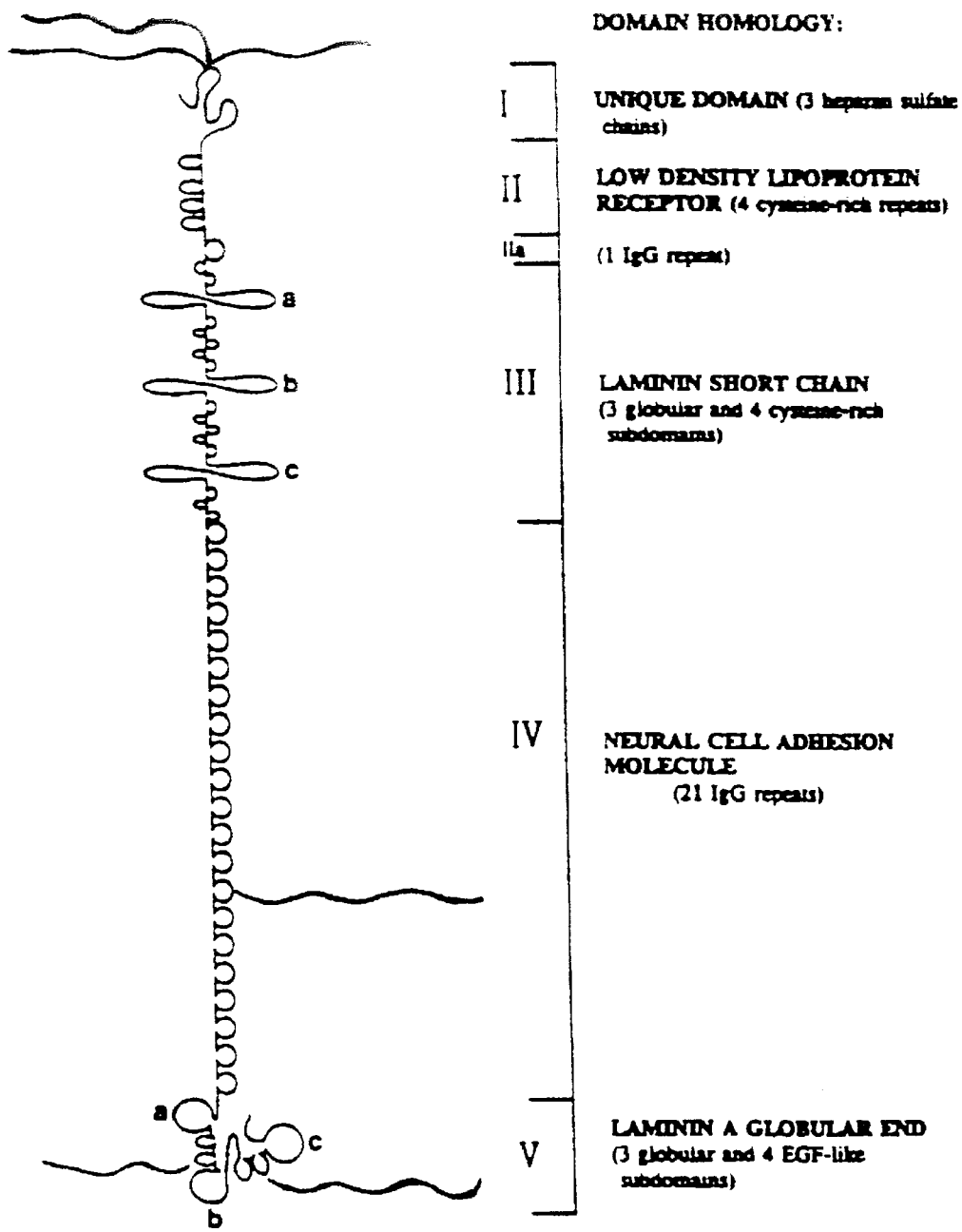
FIG. 1 is a schematic demonstrating the five structural domains of perlecan.

As stated previously, perlecan is a specific heparan sulfate proteoglycan and a common constituent of all amyloid deposits regardless of the specific amyloid protein involved. Perlecan is believed to play a primary role in the pathogenesis of amyloidosis and contributes to the formation, deposition, accumulation and/or persistence of amyloid in a variety of tissues and different clinical settings. Previous animal models overexpressing a specific amyloid protein only rarely produce some of the pathology associated with different amyloid diseases, or produce fibrillar amyloid in a different location than that observed clinically in humans, making it extremely difficult to screen in vivo for potential therapeutics for the various amyloid diseases. Additionally, perlecan is an extremely difficult macromolecule to isolate in pure and substantial quantities, and a transfected cell line that overexpresses perlecan would enable one to isolate perlecan for purification in sufficient quantities for use in a number of different biological assays. Since perlecan is a proteoglycan which contains a large core protein (~400 kilodaltons), previous attempts to successfully produce transgenic mice which overexpress the entire perlecan core protein have not been achieved. It appears that for the successful overexpression of the entire perlecan core protein the strategies for ligating overlapping cDNA clones which cover the entire 12 kb message of murine perlecan core protein (or the entire 14 kb message of human perlecan core protein), as well as the choice of specific promoter and enhancers for use in the construction strategy of perlecan transgenic mice is essential. In the present invention, unique restriction sites were used to ligate together 7 overlapping cDNA clones to produce a single 12 kb cDNA clone that encodes for mouse perlecan's ~400 kDa core protein. A novel construct, designated pCA-DI-V, which utilizes a cytomegalovirus enhancer and chick β-actin promoter, has led to successful overexpression of mouse perlecan (domains I–V) in transfected cells and in transgenic mice. Overproduction of perlecan was achieved in both COS cells and P19 cells (embryonic carcinoma cells which differentiate into neuron-like cells following retinoic acid treatment). Overexpression of perlecan in P19 cells led to an 8–10-fold increase in secreted beta-amyloid protein (Aβ) levels, and contributed to a marked decrease in neuronal survival.These latter studies suggest that perlecan overexpression in animal cells or non-human transgenic animals may be sufficient to cause the accumulation of Alzheimer's-type amyloid leading to neuropathological and behavioral consequences. Production of perlecan transgenic mice, and the mating of these mice with transgenic animals which overexpress a given amyloid protein or its precursor protein, and/or other components implicated in amyloid pathogenesis (i.e. double transgenic mice) will produce progeny that develop much or all of the phenotypic pathology of a given amyloid disease. As an example for screening methods for Alzheimer's disease, perlecan transgenic animals, cells derived from perlecan transgenic animals, or perlecan-transfected animal cells, either alone or in combination with other amyloid disease implicated components, are used to screen for compounds altering the pathological course of Alzheimer's disease as measured by their effect on beta-amyloid precursor proteins (βPPs), Aβ, and numerous other Alzheimer's disease markers in animals, the neuropathology of the animals, as well as behavioral alterations in the animals. As an example of production of double transgenic mice, successful mating of perlecan transgenic animals with transgenic mice which overproduce the C-terminal 99 amino acids of βPP, has been achieved and led to the birth of progeny which carry both the perlecan and βPP genes. The production of new transgenic animal models, and animal cells of amyloid diseases may be used as in vivo and in vitro screening tools to aid in the identification of lead therapeutics for the amyloidoses and for the treatment of clinical manifestations associated with these diseases. The successful overproduction of perlecan in transfected cells also serves as a new means to isolate perlecan which will meet the increasing demands for use of perlecan for a variety of in vitro and in vivo assays.

"Amyloid" as a Therapeutic Target in Alzheimer's Disease

The most common form of amyloidosis is found in the brains of patients with Alzheimer's disease. Alzheimer's disease is the most common cause of dementia in middle and late life, and is manifested by progressive impairment of memory, language, visuospatial perceptions and behavior (A Guide to the Understanding of Alzheimer's Disease and Related Disorders, edited by Jorm, New York University Press, New York (1987)). A diagnosis of probable Alzheimer's disease can be made on clinical criteria (usually by the exclusion of other diseases, memory tests etc.), but a definite diagnosis requires the histological examination of specific abnormalities in the brain tissue usually obtained at autopsy.

In Alzheimer's disease, the parts of the brain essential for cognitive processes such as memory, attention, language, and reasoning degenerate, robbing victims of much that makes us human, including independence. In some inherited forms of Alzheimer's disease, onset is in middle age, but more commonly, symptoms appear from the mid-60's onward. Alzheimer's disease is characterized by the deposition and accumulation of a 39–43 amino acid peptide termed the beta-amyloid protein, A$\beta$ or $\beta$/A4 (Glenner and Wong, *Biochem. Biophys. Res. Comm.* 120:885–890 (1984); Masters et al., *Proc. Natl. Acad. Sci., USA* 82:4245–4249 (1985); Husby et al., *Bull. WHO* 71:105–108 (1993)). This small peptide is a major component which makes up the amyloid deposits of neuritic "plaques" and in the walls of blood vessels (known as cerebrovascular amyloid deposits) in the brains of patients with Alzheimer's disease. In addition, Alzheimer's disease is characterized by the presence of numerous neurofibrillary "tangles", consisting of paired helical filaments which abnormally accumulate in the neuronal cytoplasm (Grundke-Iqbal et al., *Proc. Natl. Acad. Sci. USA* 83:4913–4917 (1986); Kosik et al., *Proc. Natl. Acad. Sci. USA* 83:4044–4048 (1986); Lee et al., *Science* 251:675–678 (1991)). The pathological hallmarks of Alzheimer's disease is therefore the presence of "plaques" and "tangles", with amyloid being deposited in the central core of plaques and within the blood vessel walls. It is important to note that a so-called "normal aged brain" has some amyloid plaques and neurofibrillary tangles present. However, in comparison, an Alzheimer's disease brain shows an over abundance of plaques and tangles. Therefore, differentiation of an Alzheimer's disease brain from a normal brain from a diagnostic point of view is primarily based on quantitative assessment of "plaques" and "tangles".

In an Alzheimer's disease brain, are usually thousands of neuritic plaques. The neuritic plaques are made up of extracellular deposits consisting of an amyloid core usually surrounded by enlarged axons and synaptic terminals, known as neurites, and abnormal dendritic processes, as well as variable numbers of infiltrating microglia and surrounding astrocytes. The neurofibrillary tangles present in the Alzheimer's disease brain mainly consist of tau protein, which is a microtubule-associated protein (Grundke-Iqbal et al., *Proc. Natl. Acad. Sci. USA* 83:4913–4917 (1986); Kosik et al., *Proc. Natl. Acad. Sci. USA* 83:4044–4048 (1986); Lee et al., *Science* 251:675–678 (1991)). At the ultrastructural level, the tangle consists of paired helical filaments twisting like a ribbon, with a specific crossing over periodicity of 80 nanometers. In many instances within a neurofibrillary tangle, there are both paired helical filaments and straight filaments. In addition, many times the nerve cell will die, leaving the filaments behind. These tangles are known as "ghost tangles" since they are the filamentous remnants of the dead neuron.

The other major type of lesion found in the brain of an Alzheimer's disease patient is the accumulation of amyloid in the walls of blood vessels, both within the brain parenchyma and in the walls of the larger meningeal vessels which lie outside the brain. The amyloid deposits localized to the walls of blood vessels are referred to as cerebrovascular amyloid or congophilic angiopathy (Mandybur, *J. Neuropath. Exp. Neurol.* 45:79–90 (1986); Pardridge et al., *J. Neurochem.* 49:1394–1401 (1987)).

In addition, Alzheimer's disease patients demonstrate neuronal loss and synaptic loss. Furthermore, these patients also exhibit loss of neurotransmitters such as acetylcholine. Tacrine, the first FDA approved drug for Alzheimer's disease is a cholinesterase inhibitor (Cutler and Sramek, *New Engl. J. Med.* 328:808–810 (1993)). However, this drug has showed limited success, if any, in the cognitive improvement in Alzheimer's disease patients and initially had major side effects such as liver toxicity.

For many years there has been an ongoing scientific debate as to the importance of "amyloid" in Alzheimer's disease and whether the "plaques" and "tangles" characteristic of this disease, were a cause or merely the consequences of the disease. Recent studies during the last few years have now implicated that amyloid is indeed a causative factor for Alzheimer's disease and not merely an innocent bystander. The Alzheimer's disease major protein known as beta-amyloid protein (A$\beta$), in cell culture has been shown to cause degeneration of nerve cells within short periods of time (Pike et al., *Br. Res.* 563:311–314 (1991); *J. Neurochem.* 64:253–265 (1994)). Studies suggest that it is the fibrillar structure, a characteristic of all amyloids, that is responsible for the neurotoxic effects. The A$\beta$ has also been found to be neurotoxic in slice cultures of hippocampus (the major memory region affected in Alzheimer's) (Harrigan et al., *Neurobiol. Aging* 16:779–789 (1995)) and induces nerve cell death in transgenic mice (Games et al., *Nature* 373:523–527 (1995); Hsiao et al., *Neuron* 15:1203–1218 (1995)). In addition, injection of the Alzheimer's A$\beta$ into rat brain causes memory impairment and neuronal dysfunction (Flood et al., *Proc. Natl. Acad. Sci.* 88:3363–3366 (1991); *Br. Res.* 663:271–276 (1994)), two hallmarks of Alzheimer's disease. Probably, the most convincing evidence that amyloid (i.e. beta-amyloid protein) is directly involved in the pathogenesis of Alzheimer's disease comes from recent genetic studies. It has been discovered that the production of A$\beta$ can result from mutations in the gene encoding, its precursor, known as the beta-amyloid precursor protein (Van Broeckhoven et al., *Science* 248:1120–1122 (1990); *Euro. Neurol.* 35:8–19 (1995); Murrell et al., *Science* 254:97–99 (1991); Haass et al., *Nature Med.* 1:1291–1296 (1995)). This precursor protein when normally processed only usually produces very little of the toxic A$\beta$. The identification of mutations in the amyloid precursor protein gene which causes familial, early onset Alzheimer's disease is the strongest argument that amyloid is central to the pathogenetic process underlying this disease. Four reported disease-causing mutations have now been discovered which demonstrate the importance of the beta-amyloid protein in causing familial Alzheimer's disease (reviewed in Hardy, *Nature Genet.* 1:233–234 (1992)). These studies suggest that providing a drug to reduce, eliminate or prevent fibrillar beta-amyloid protein formation, deposition, accumulation and/or persistence in the brains of human patients should be considered an effective therapeutic.

Proteoglycans

Proteoglycans (PGs) are a group of complex macromolecules which are found in all organs and tissues, intracellularly in a variety of different cell types, or extracellularly in the matrix where they are exported for a variety of functions. Proteoglycans consist of a linear protein core backbone to which one or more glycosaminoglycan (GAG) chains are covalently linked (Hascall and Hascall, in *Cell Biology of the Extracellular Matrix*, Hay editor, New York, Plenum Press, pp. 39, (1981); Hassell et al., *Ann. Rev. Biochem.* 55:539–567 (1986)). The highly anionic GAG chains consist of repeating disaccharide units, containing 1) hexosamine (either D-glucosamine or D-galactosamine), and hexuronic acid (either D-glucuronic acid or L-iduronic acid)(Muir, *Am. J. Med.* 47:673–690 (1969)). The PGs are traditionally named according to the identification of the primary GAG present and several major GAGs have been identified. These are hyaluronic acid, heparan sulfate, heparin, chondroitin-4-sulfate, chondroitin-6-sulfate, dermatan sulfate and keratan sulfate. Usually the linkage between the GAG chains and the protein core backbone consists of a xylose-galactose-galactose attachment region with the xylose molecule covalently linked to the hydroxyl groups of a serine residue on the protein core (Roden and Armand, *J. Biol. Chem.* 241:65–70 (1966)). The exception is hyaluronic acid which has a backbone consisting of alternating D-glucuronic acid and D-glucosamine units with no protein component. Keratan sulfate os the one PG which lacks the typical xylose-serine linkage. It is linked to protein either via a N-acetylgalactosamine residue linked to either serine or threonine (in cartilage) or via a N-acetylglucosamine residue attached directly to an asparagine residue (in cornea)(Hascall and Hascall, in *Cell Biology of the Extracellular Matrix*, Hay editor, New York, Plenum Press, pp. 39, (1981); Muir, *Am. J. Med.* 47:673–690 (1969)).

Heparan Sulfate Proteoglycans: A Common Component of All Amyloids

It is clear from the research literature that finding novel therapeutics for amyloid formation, deposition, accumulation and persistence is today considered a relevant strategy for Alzheimer's disease and other amyloid diseases. The major question that persisted in amyloid research was: why do all amyloids containing unrelated proteins all form an amyloid fibril with similar characteristics (i.e. all consist of fibrils of 7–10 nm and contain a predominant beta-pleated sheet secondary structure)? Is there a common component that may play a similar role in the pathogenesis of all amyloids?

The answer to this central and important question in understanding the mechanisms involved in amyloid diseases. Early studies demonstrated that highly sulfated GAGs (later determined to be specific heparan sulfate PGs) were concurrently deposited with inflammation-associated amyloid (i.e. AA amyloid) in a well-defined experimental mouse model (Snow et al., *Lab. Invest.* 56:665–675 (1987)). Later studies demonstrated that heparan sulfate PGs were temporally and structurally associated with the deposition and accumulation of AA amyloid in a variety of different tissues (Snow et al., *J. Histochem. Cytochem.* 39:1321–1330 (1991)). Specific staining techniques and immunohistochemical methods then determined that highly sulfated PGs were a common feature of most, if not all, amyloids, independent of the specific amyloid protein involved, the stage of the amyloid disease, and the tissue site of amyloid deposition (Snow et al., *Lab. Invest.* 56:120–123 (1987); *Am. J. Path.* 133:456–463 (1988); *Acta Neuropath.* 77:337–342, (1980); *Lab. Invest.* 63:601–611 (1990)).

Studies were then pursued to further try to understand the potential involvement of specific PGs in Alzheimer's disease amyloidosis. In initial studies using specific immunohistochemical probes it was first determined that heparan sulfate PGs were an important constituent of amyloid in neuritic plaques and cerebrovascular amyloid deposits (Snow et al., *Am. J. Path.* 133:456–463 (1988)). It was later revealed that the antibodies employed for this initial study were in fact those that specifically recognized the core protein of a large heparan sulfate PG, known as "perlecan". Heparan sulfate PGs (and specifically perlecan) were also co-localized to prion protein (PrP) amyloid plaques in Gerstmann-Straussler syndrome, Creutzfeldt-Jakob disease, kuru and animal scrapie (Snow et al., *Lab. Invest.* 63:601–611 (1990)). It was initially postulated that specific heparan sulfate PGs play important roles in amyloidosis by 1) influencing amyloidogenic proteins to adapt predominantly beta-pleated sheet structures (i.e. indicative of amyloid), 2) determining the anatomical location of amyloid deposition, and 3) contributing to the stability of amyloid and its inaccessibility to proteolytic degradation in tissues, thus not allowing the body to properly degrade and remove unwanted amyloid deposits (Snow and Wight, *Neurobiol. Aging* 10:481–497 (1989)).

Perlecan and/or heparan sulfate PG accumulation in conjunction with a variety of different amyloid proteins is an early event, and does not merely represent secondary and non-specific deposition. In experimental inflammation-associated amyloidosis, perlecan expression actually precedes AA amyloid deposition (Ailles et al., *Lab. Invest.* 69:443–447 (1993)) suggesting that up-regulation of specific PGs may be an initiating event leading to eventual amyloid formation and/or deposition. In a previous study (Snow et al., *Am. J. Path.* 137:1253–1270 (1990)), the brains of Down's syndrome patients (aged 1 day to 51 years) were examined to determine the possible sequence of events leading to beta-amyloid protein (Aβ) and PG deposition. Down's syndrome patients, who were completely devoid of any Aβ immunoreactivity, demonstrated prominent heparan sulfate immunoreactivity in neurons as early as 1 day after birth, which was not observed in similar aged-matched non-Down's syndrome brains. In older patients, aged 18 and 24 years, diffuse Aβ immunoreactivity (which was Congo red negative and therefore suggestive of non-fibrillar deposits) in the extracellular matrix was accompanied by co-localized heparan sulfate deposition. In patients, over the age of 35 years, fibrillar Aβ deposits in neuritic plaques and cerebrovascular amyloid accumulation were also observed with co-localized heparan sulfate immunoreactivity. This important study suggested that heparan sulfate accumulation within neurons may be a primary event eventually leading to the co-accumulation of heparan sulfate and Aβ in the extracellular matrix. It is feasible that once the interaction between heparan sulfate and Aβ (or its precursor protein) takes place, a cascade of events occurs which lead to fibril formation, deposition and eventual persistence.

The Importance of Heparan Sulfate Proteoglycans in Alzheimer's Disease

To date at least four different classes of PGs/GAGs have now been shown to be present in the Aβ-containing deposits (i.e. neuritic plaques, cerebrovascular amyloid) of Alzheimer's disease. In 1988, it was discovered that heparan sulfate PGs were specifically present in the amyloid deposits and neurofibrillary tangles of Alzheimer's disease (Snow et al., *Am. J. Path.* 133:456–463 (1988)). In later years, the particular type of heparan sulfate PG found was a large PG with a total molecular weight of ~800,000 known as "perlecan". In 1992, a second PG present in the periphery of neuritic plaques and within neurofibrillary tangles was discovered, which was a small dermatan sulfate PG known as decorin (Snow et al., *J. Histochem. Cytochem.* 40:105–113 (1992)). In 1993, a third class of PGs were discovered, namely chondroitin sulfate, which were present in the periphery of neuritic plaques and within neurofibrillary tangles of Alzheimer's disease brain (DeWitt et al., *Exp. Neurol.* 121:149–152 (1993)). The specific type of chondroitin sulfate PG present to this day has yet to be identified. In 1996, a keratan sulfate PG, known as SV2PG, was discovered which was localized primarily to synaptic vesicles in the periphery of neuritic plaques (Snow et al., *Exp. Neurol.* 138:305–317 (1996)).

Of all the different specific PGs/GAGs mentioned above, it has become exceedingly clear that the heparan sulfate PGs may be the most important class of PG implicated in Alzheimer's disease. This is due to the fact that heparan sulfate PGs still remain the only class of PG that has been immunolocalized to 1) all three characteristic lesions of Alzheimer's disease (i.e. neuritic plaque, neurofibrillary tangles, and cerebrovascular amyloid deposits), and 2) specifically to the Aβ-containing amyloid fibrils in both neuritic plaques and cerebrovascular amyloid deposits. The data suggests that perlecan is a major heparan sulfate PG found within the amyloid core of neuritic plaques and appears to be present in most, if not all, central nervous system and systemic amyloids (reviewed in Snow and Wight, *Neurobiol. Aging* 10:481–497 (1989)). Overproduction of perlecan in a transgenic animal or transfected cell line has, as yet, not been achieved, and is needed to develop new models for developing therapeutics for the amyloid diseases.

Perlecan Production by Different Cell Types and its Postulated Roles in the Pathogenesis of Amyloid Diseases Perlecan is present on all basement membranes (Dziadek et al., *EMBO J*. 4:905–912 (1985); Kato et al., *J. Cell Biol*. 106:2203–2210 (1988); Murdoch et al., *J. Histochem. Cytochem*. 42:239–249 (1994)) and was previously cloned from both human (Murdoch et al., *J. Biol. Chem*. 267:8544–8557 (1992); Kallunki and Tryggvason, *J. Cell. Biol*. 116:559–571 (1992)) and mouse (Noonan et al., *J. Biol. Chem*. 266:22939–22947 (1991)). Perlecan is known to be produced by different cell types including endothelial cells (Kinsella and Wight, *Biochem*. 27:2136–2144 (1988); Saku and Furthmayr, *J. Biol. Chem*. 264:3514–3523 (1989); Rescan et al., *Am. J. Path*. 142:199–208 (1993)), smooth muscle cells (Nikkari et al., *Am. J. Path*. 144:1348–1356 (1994)), fibroblasts (Murdoch et al., *J. Histochem. Cytochem*. 42:239–249 (1994); Heremans et al., *J. Cell Biol*. 109:3199–3211 (1989)), epithelial cells (Morris et al., *In Vitro Cell Dev. Biol*. 30:120–128 (1994); Ohji et al., *Invest. Opth. Vis. Sci*. 35:479–485 (1994); Van Det et al., *Biochem. J*. 307:759–768 (1995)), and synovial cells (Dodge et al., *Lab. Invest*. 73:649–657 (1995)). Perlecan is also synthesized by bone marrow derived cells (Grassel et al., *Mol. Cell Biochem*. 145:61–68 (1995)) and is present in cancerous tissue including metastatic melanomas (Cohen et al., *Cancer Res*. 54:5771–5774 (1994)), human breast tumors (Guelstein et al., *Int. J. Cancer* 53:269–277 (1993)), and liver tumors (Kovalsky et al., *Acta Biomed. Ateneo Parmense* 64:157–163 (1993)). Both F9 embryonal carcinoma cells (which form parietal endoderm) and P19 embryonal carcinoma cells (which form cholinergic neurons) also demonstrate marked increased perlecan expression and synthesis upon differentiation (Chakravarti et al., *Dev. Dyn*. 197:107–114 (1993); Sekiguchi et al., *J. Neurosc. Res*. 38:670–686 (1994)).

Perlecan is postulated to play a primary role in the pathogenesis of Alzheimer's disease (AD) amyloidosis, as well as in other types of central nervous system and systemic amyloidoses (reviewed in Snow and Wight, *Neurobiol. Aging* 10:481–497 (1989)). Only the heparan sulfate class of PGs have been found to be immunolocalized to all three major lesions (i.e. neuritic plaques, neurofibrillary tangles and cerebrovascular amyloid deposits) in Alzheimer's disease brain and specifically to the beta-amyloid protein (Aβ)-containing amyloid fibrils in both amyloid plaques and congophilic angiopathy (Snow et al., *Am. J. Path*. 133:456–463 (1988); Snow and Wight, *Neurobiol. Aging* 10:481–497 (1989); Perlmutter and Chui, *Brain Res. Bull*. 24:677–686 (1990); Snow et al., *Am. J. Path*. 137:1253–1270 (1990); Su et al., *Neuroscience* 51:801–813 (1992); Van Gool et al, *Dementia* 4:308–314 (1993)). Accumulating evidence suggests that perlecan is a major heparan sulfate PG present within the AS-containing amyloid deposits in Alzheimer's disease (Snow et al., *Am. J. Path*. 133:456–463 (1988); Snow and Wight, *Neurobiol. Aging* 10:481–497 (1989); Snow et al., *Am. J. Path*. 137:1253–1270 (1990); Snow et al., *Am. J. Path*. 144:337–347 (1994)) and may play a primary role in Aβ fibril formation, deposition, accumulation and persistence. The consistent co-localization of perlecan to Aβ deposits which exist in both a fibrillar and non-fibrillar form (Snow et al., *Am. J. Path*. 144:337–347 (1994)) is probably due to perlecan's high affinity interactions with Aβ (Snow et al., *J. Neuropath. Exp. Neurol*. 48:352 (1989) Abstract; Buee et al., *Brain Res*. 601:154–163 (1993); Buee et al., *Brain Res*. 627:199–204 (1993); Snow et al., *Arch. Biochem. Bionhys*. 320:84–95 (1995)) and with beta-amyloid precursor proteins (Narindrasorasak et al., *J. Biol. Chem*. 266:12878–12883 (1991)). Residues 13–16 of Aβ have been identified as a perlecan binding site (Snow et al., *J. Neuropath. Exp. Neurol*. 48:352 (1989) Abstract; Brunden et al., *J. Neurochem*. 61:2147–2154 (1993); Snow et al., *Arch. Biochem. Biophys*. 320:84–95 (1995)). This region contains a heparin/heparan sulfate binding consensus sequence (Cardin and Weintraub, *Arterioscl*. 9:21–32 (1989)), and is adjacent to the postulated alpha-secretase cleavage site on Aβ (at Lys-16). Once bound, perlecan is believed to influence the secondary structure and/or aggregation properties of Aβ and/or beta-amyloid precursor proteins (Fraser et al., *J. Neurochem*. 59:1531–1540 (1992)). Perlecan also appears to play a role in stabilizing fibrillar Aβ amyloid when deposited in vivo (Snow et al., *Neuron* 12:219–234 (1994); Snow et al., *Soc. Neurosc. Abst*. 21:1292 (1995) Abstract), and protects Aβ from degradation by proteases as demonstrated in vitro (Gupta-Bansal et al., *J. Biol. Chem*. 270:18666–18671 (1995)). The combined results described above suggest that perlecan is an important macromolecule that has now been implicated at several key steps in the pathogenesis of Aβ amyloidosis in Alzheimer's disease. However, due to perlecan's large size and complex structure (described below), production of transgenic animals or transfected cells which overproduce perlecan has, as yet, not been achieved.

DNA Sequences and the Structure of Perlecan

The DNA sequence for human perlecan encodes for a protein core with a molecular weight of approximately 466.564 kDa (Murdoch et al., *J. Biol. Chem*. 267:8544–8557 (1992)) whereas the DNA sequence for mouse perlecan encodes for a protein core with a molecular weight of approximately 396 kDa (Noonan et al., *J. Biol. Chem*. 266:22939–22947 (1991)). A schematic demonstrating the five structural domains of perlecan is shown in FIG. 1. The genes for human (Murdoch et al., *J. Biol. Chem*. 267:8544–8557 (1992); Kallunki and Tryggvason, *Cell Biol*. 116:559–571 (1992)) and mouse (Noonan et al., *J. Biol. Chem*. 266:22939–22947 (1991)) perlecan have been cloned and the predicted core protein consists of five distinct domains (FIG. 1). Domain I contains the proposed heparan sulfate GAG attachment sites and is unique to perlecan showing no similarity to other known protein sequences. The location of the three Ser-Gly consensus heparan sulfate GAG attachment sites at the N-terminus corresponds with the number and position of known GAG chains (Kokenyesi and Silbert, *Biochem. Biophys. Res. Comm*. 211:262–267

(1995)). Domain II is homologous to the LDL binding domain present in the LDL-receptor, whereas Domain III has homology to the globule-rod regions of the laminin short arms. Domain IV is a highly repetitive region with numerous immunoglobulin-like repeats that show the highest similarity to neural cell adhesion molecule (N-CAM). Domain V has three globular repeats very similar to the domain G repeats in the laminin A chain and the equivalent segment of the A chain homologue, merosin, and two epidermal growth factor-like regions (Noonan and Hassell, *Kidney Int.* 43:53–60 (1993)). The perlecan core protein is therefore a unique and large macromolecule with homology to a number of other well known proteins.

Transgenic Models Trying to Mimic the Neuropathology of Alzheimer's Disease

A number of transgenic animal models have been produced to try to mimic some or all of the neuropathology of AD (reviewed in Greenberg et al., *Neurobiol. Aging* 17:153–171 (1996)). The rationale for most of these models was that overproduction of the beta-amyloid precursor protein (βPP) transgene (containing all or part of the βPP sequence) could lead to the eventual development of Aβ deposits in mouse brain and subsequent plaque and tangle formation. In some of the first βPP transgenic animal model studies, (Wirak et al., *Science* 253:323–325 (1991)) generated transgenic mouse lines containing the Aβ sequence under the control of the human βPP promoter. After 1 year, these mice developed Aβ deposits within hippocampal neurons and formed aggregates of amyloid-like fibrils. Quon et al (*Nature* 352:239–241 (1991)) used a full length βPP-751 sequence linked to a neuron-specific enolase promoter. Transgenic mice with this construct displayed extracellular Aβ immunoreactive deposits, which were infrequently stained with Thioflavin S, but not by Congo red, suggesting a pre-amyloid like composition. Kawabata et al., (*Nature* 354:476–478 (1991)) developed transgenic mouse lines massively overexpressing a construct encoding the C-terminal 100 amino acids of βPP under control of a Thy-1 element. These mice displayed pathology remarkably similar to that observed in AD including amyloid plaques, neurofibrillary tangles and neurodegeneration in hippocampus, neocortex and even cerebellum. While extremely promising, the report by Kawabata et al., (*Nature* 354:476–478 (1991)) was retracted whereas the study by Wirak et al., (*Science* 253:323–325 (1991)) was questioned (Jucker et al., *Science* 255:1443–1445 (1992)).

Recently, two transgenic animal models which probably produce the most advanced neuropathology observed in animals to date, have been described. Games et al., (*Nature* 373:523–527 (1995)) generated transgenic mice using platelet-derived growth factor (PDGF)-β driving a human βPP minigene encoding the βPP-717 mutation (valine at residue 717 substituted by phenylalanine) associated with familial AD. These mice progressively developed some of the neuropathological hallmarks of AD including Thioflavin S positive Aβ deposits, neuritic plaques, synaptic loss, astrocytosis and microgliosis. This transgenic animal model was studied more closely by Masliah et al., (*J. Neurosc.* 16:5795–5811 (1996)) who demonstrated the ultrastructure of the neuritic plaques formed in the brain parenchyma of these mice. No cerebrovascular amyloid deposition nor neurofibrillary tangles were observed to date in these mice.

Another transgenic animal model was recently reported (Hsiao et al., *Science* 274:99–102 (1996)) in which the 695-amino acid isoform of the human βPP containing the double mutation (Lys$^{670}$ to Asn, Met$^{671}$ to Leu), which was found in a large Swedish family with early onset Alzheimer's Disease, was inserted into a hamster prion protein cosmid vector. These mice demonstrated a 5-fold increased in Aβ (1–40) and a 14-fold increase in Aβ (1-42/43) accompanied by numerous amyloid plaques stained with Congo red in cortical and limbic structures. These transgenic animals had normal learning and memory in spatial reference and alternating tasks at 3 months of age but showed impairment by 9–10 months of age. In these mice, no cerebrovascular amyloid deposition nor neurofibrillary tangles were observed.

The most recent transgenic models described above may one day lead to fruitful insights into the pathogenesis of AD and may ultimately be used to screen and identify new therapeutics to treat AD. However, these transgenic models do have a major shortcoming. These models have yet to show convincing cerebrovascular amyloid deposition and neurofibrillary tangle formation in brain. This indicates that these transgenic models are missing two of the three major neuropathological hallmarks of AD (i.e. the other being the neuritic plaque). Is there a missing factor that these transgenic models have yet to take into account?

Heparan Sulfate Containing-Proteoglycans May be the Additional Factor Necessary for Amyloid Plaque and Neurofibrillary Tangle Formation in Alzheimer's Disease Two very recent studies (Goedert et al., *Nature* 383:550–553 (1996); Perez et al., *J. Neurochem.* 67:1183–1190 (1996)) implicate that heparan sulfate containing-PGs may be necessary additional factors which may play roles in the formation of neurofibrillary tangles. In one study, Goedert et al., (*Nature* 383:550–553 (1996)) found that highly sulfated GAGs such as heparin and heparan sulfate stimulated different recombinant isoforms of tau protein to form paired helical filaments in vitro. The paired helical filament formation was found to be GAG-dependent, and phosphorylation-independent indicating that the presence of heparan sulfate GAGs was a key element in neurofibrillary tangle formation. Highly sulfated GAGs such as heparin and heparan sulfate were potent inducers of paired helical filament formation, whereas less sulfated GAGs such as chondroitin sulfate and dermatan sulfate were much less effective. Non-sulfated GAGs such as hyaluronic acid did not induce any paired helical filament formation indicating that sulfation was an important factor. Goedert et al., (*Nature* 383:550–553 (1996)) also confirmed some earlier work (Snow et al., *Am. J. Path.* 137:1253–1270 (1990)) that heparan sulfate accumulates in the cytoplasm of neurons prior to the appearance of neurofibrillary tangles. Heparan sulfate and chondroitin sulfate have also been detected in tangle-bearing neurons in Alzheimer's Disease (Perry et al., *J. Neurosc.* 11:3679–3683 (1991)) and in neurons bearing tangles in other non-Alzheimer's diseases such as progressive supranuclear palsy (DeWitt et al., *Br. Res.* 656:205–209 (1994)). Perez et al., (*J. Neurochem.* 67:1183–1190 (1996)) also found heparin to induce different tau protein fragments to assemble into paired helical filaments in vitro. The induction of paired helical filaments by heparin/heparan sulfate suggests that PGs containing this particular class of GAGs may the missing factor essential for the induction of both amyloid plaques and neurofibrillary tangles in transgenic animals. Overexpression of perlecan (a specific heparan sulfate containing-PG) in transgenic animals may therefore lead to both amyloid plaque and neurofibrillary tangle formation, and ultimately serve as a new animal model of Alzheimer's disease.

Other Co-Components Present in Alzheimer's and in Other Amyloid Diseases

Alzheimer's disease is characterized by numerous changes in the expression levels of various proteins, the biochemical activity and histopathology of brian tissue, as well as cognitive changes in affected individuals. Such characteristic changes associated with Alzheimer's disease have been well documented. The most prominent change, as discussed herein, is the deposition of Aβ into amyloid plaques (Haass and Selkoe, *Cell* 75:1039–1042 (1993)). Besides specific PGs, a variety of other molecules have also been known to be important components of Alzheimer's disease amyloid or neurofibrillary tangles and include tau protein (Grundke-Iqbal et al., *Proc. Natl. Acad. Sci. USA* 83:4913–4917 (1986); Kosik et al., *Proc. Natl. Acad. Sci. USA* 83:4044–4048 (1986); Lee et al., *Science* 251:675–678 (1991)), apolipoprotein E (Corder et al., *Science* 261:921–923 (1993); Strittmatter et al., *Proc. Natl. Acad. Sci. USA* 90:8098–8102 (1993)), alpha$_1$-antichymotrypsin (Abraham et al., *Cell* 52:487–501 (1988)), amyloid P component (Coria et al., *Lab. Invest.* 58:454–458 (1988)), ubiquitin (Mori et al., *Science* 235:1641–1644 (1987)), cytokines (McGeer et al., *Can. J. Neurol. Sci.* 16:516–527 (1989); reviewed in Rogers, *CNS Drugs* 4:241–244 (1994)), growth factors (Hefti and Weiner, *Ann. Neurol.* 20:275–281 (1986); Hefti et al., *Neurobiol. Aging* 10:515–533 (1989); Kato et al., *Neurosc.* 122:33–36 (1991); Tooyama et al., *Neurosc. Lett.* 121:155–158 (1991)), and complement factors (Eikenbloom et al., *Virch. Arch. B Cell Pathol.* 56:259–262 (1989)). Each of these components described above may be utilized for the production of new transgenic animals and/or transfected cells. Overexpression of perlecan with another amyloid or neurofibrillary tangle component described above may also lead to new models of amyloidosis (for Alzheimer's disease and/or other amyloid diseases) and/or models of tangle neuropathology.

Alzheimer's Disease Gene Mutations

A) βPP Mutations

Certain families are genetically predisposed to Alzheimer's disease, a condition referred to as familial Alzheimer's disease, through mutations resulting in an amino acid replacement at position 717 of the full length protein (Goate et al., supra (1991); Murrell et al., supra (1991)). Another FAD mutation contains a change in amino acids at positions 670 and 671 of the full length protein (Mullan et al., supra (1992)). In one form of this mutation, the lysine at position 670 is replaced by asparagine and the methionine at position 671 is replaced by leucine. The effect of this mutation is to increase the production of Aβ in cultured cells approximately 7-fold (Citron et al., *Nature* 360:672–674 (1992); Lai et al., *Science* 259:514–516 (1993)). Additional mutations in βPP at amino acids 669, 670 and 671 have been shown to reduce the amount of Aβ processed from βPP (Citron et al., *Neuron* 14:661–670 (1995)). The βPP construct with Val at amino acid 690 produces an increased amount of a truncated form of Aβ.

βPP expression clones can be constructed to bear a mutation at amino acids 669, 670, 671, 690, 692, or 717 of the full length protein. The mutations from Lys to Asn and from Met to Leu at amino acids 670 and 671, respectively, are sometimes referred to as the Swedish mutation. Additional mutations can also be introduced at amino acids 669, 670 or 671 which either increase or reduce the amount of Aβ processed from βPP. Some mutations at amino acid 717 are sometimes referred to as the Hardy mutation. Such mutations can include conversion of the wild-type Val717 codon to a codon of Ile, Phe, Gly, Tyr, Leu, Ala, Pro, Trp, Met, Ser, Thr, Asn, or Gln, A preferred substitution for Val717 is Phe. These mutations predispose individuals expressing the mutant proteins to develop Alzheimer's disease. It is believed that the mutations affect the expression and/or processing of βPP, shifting the balance towards Alzheimer's pathology. Mutations at amino acid 669 can include conversion of the wild-type Val669 codon to a codon for Trp, or deletion of the codon. Mutations at amino acid 670 can include conversion of the wild-type Lys670 codon to a codon for Asn or Glu, or deletion of the codon. Mutations at amino acid 671 can include conversion of the wild-type Met671 codon to a codon for Leu, Val, Lys, Tyr, Glu or Ile, or deletion of the codon. A preferred substitution for Lys670 is Asn, and a preferred substitution for Met671 is Leu. These mutations predispose individuals expressing the mutant proteins to develop Alzheimer's disease.

B) Presenilin 1 and Presenilin 2

In 1992, evidence for a locus causing early-onset Alzheimer's disease was reported on the long-arm of chromosome 14 (Schellenberg et al., *Science* 258:668–671 (1992)). This result was quickly confirmed by several groups. A positional cloning strategy was then used to isolate a candidate gene (S182, later re-named presenilin 1 or PS1) that carried coding region mutations in families multiply affected by early-onset Alzheimer's disease (Sherrington et al., *Nature* 375:754–760 (1995)). Since then more than 35 different missense mutations have been found in the PS1 gene in over 50 families of different ethnic origins (Van Broeckhoven, *Nat. Genet.* 11:230–232 (1995); Clark et al., *Nat. Genet.* 11:219–222 (1996)). All PS1 gene mutations reported except one are missense mutations.

The mean age of onset of disease in individuals with PS1 mutations is generally earlier than it is in individuals with βPP mutations, but considerable overlap does exist (the age range for PS1 is 29 to 62 years, and for βPP is 43 to 62 years). Several of the PS1 gene mutations are found in families of different ethnic origins suggesting that independent mutational events have occurred at the same nucleotide.

The PS1 gene contains 10 protein-coding exons and 2 or 3 additional exons encoding the 5'-untranslated region. The major RNA transcript of the PS1 gene is about 3 kilobases and is expressed in various human brian regions. The PS1 protein has 467 amino acids and is thought to span the cell membrane 8 times, but its function is unknown.

Soon after the isolation of the PS1 gene it became clear from sequence homologies that PS1 was part of a gene family. Sequences homologous to the PS1 gene were found to map to human chromosome 1, indicating the existence of a second presenilin gene, PS2 (also called the STM2 gene). At about the same time, genetic linkage between Alzheimer's disease and DNA markers on chromosome 1 was detected in a group of Volga Germans with Alzheimer's disease (Levy-Lahad et al., *Science* 269:970–973 (1995)). Since the PS2 gene and the markers linked to the Volga German Alzheimer's disease locus were very close together, the PS2 gene was sequenced in affected individuals from several Volga German families, and a missense mutation causing substitution of asparagine by isoleucine at codon 141 was identified (Levy-Lahad et al., *Science* 269:973–977 (1995)). A second mutation, M239V, has been identified in an Italian pedigree with early-onset familial Alzheimer's disease (Rogacv et al., *Nature* 376:775–778 (1996)).

The PS2 protein contains 448 amino acids and shows 67% identity with the PS1 protein. The PS2 gene is also widely expressed in many tissues, but shows more extensive alternative splicing than PS1 (Prohar et al., Neurorep.

7:1680–1684 (1996)). However, the overall structures of the PS1 and PS2 proteins are similar, and all AD-causing mutations are in the nucleotides coding for amino acids that are conserved between the 2 genes, suggesting that the 2 proteins serve similar functions and that mutant amino acids are at positions within the protein critical to function.

As stated previously, perlecan is a specific heparan sulfate proteoglycan and a common constituent of all amyloid deposits regardless of the specific amyloid protein involved. Perlecan is believed to play a primary role in the pathogenesis of amyloidosis and contributes to the formation, deposition, accumulation and/or persistence of amyloid in a variety of tissues and different clinical settings. Previous animal models or overexpressing a specific amyloid protein only rarely produce some of the pathology associated with different amyloid diseases, or produce fibrillar amyloid in a different location than that observed clinically in humans, making it extremely difficult to screen in vivo for potential therapeutics for the various amyloid diseases. In the present invention, unique restriction sites were used to ligate together 7 overlapping cDNA clones to produce a single 12 kb cDNA clone that encodes for mouse perlecan's ~400 kDa core protein. In a preferred embodiment, a novel construct, designated pCA-DI-V, which utilizes a cytomegalovirus enhancer and chick β-actin promoter, has led to successful overexpression of mouse perlecan (domains I–V) in transfected cells and in transgenic mice.

For these studies, the constructs are introduced into animal embryos using standard techniques such as microinjection or embryonic stem cells. Cell culture based models can also be prepared by two methods. Cell cultures can be isolated from the transgenic animals or prepared from established cell cultures using the same constructs with standard cell transfection techniques.

The specific constructs that are described preferably employ a chick β-actin promoter, which causes high expression of perlecan in all tissues including brain. However, other promoters may be used which may be selected from the following: the human βPP gene promoter, mouse βPP gene promoter, rat βPP gene promoter, metallothionein III gene promoter, metallothionein I promoter, rat neuron specific enolase gene promoter, mouse neuron specific enolase promoter, human β actin gene promoter, human platelet derived growth factor B (PDGF-B) chain gene promoter, rat sodium channel gene promoter, RNA polymerase I promoter, RNA polymerase II promoter, polypeptide chain elongation factor 1-alpha promoter, neurofilament M promoter, neurofilament L promoter, glial fibrillary acidic protein promoter, prion protein promoter, insulin promoter, low affinity nerve growth factor receptor (p75) promoter, mouse myelin basic protein gene promoter, human copper-zinc superoxide dismutase gene promoter, and mammalian POU-domain regulatory gene promoter.

The specific constructs that are described preferably employ a cytomegalovirus enhancer. However, other enhancers may be used which may be selected from the following: immunoglobulin kappa 3'-enhancer, lambda enhancer, IgH 3'-enhancer, T cell receptor alpha enhancer, alpha HS-26 enhancer, alpha HS-40 enhancer, and rat insulin II gene enhancer.

The specific constructs that are described led to an overproduction of perlecan in both COS cells and P19 cells (embryonic carcinoma cells which differentiate into neuron-like cells following retinoic acid treatment). Overproduction of perlecan in P19 cells led to a marked increase in secreted Aβ levels and a marked decrease in neuronal survival. As an example for screening methods for Alzheimer's disease, perlecan transgenic animals, or perlecan-transfected animal cells, either alone or in combination with other amyloid disease co-components, are used to screen for compounds altering the pathological course of Alzheimer's disease as measured by their effect on βPPs, Aβ, and numerous other Alzheimer's disease markers in animals, the neuropathology of the animals, as well as behavioral alterations in the animals. The production of new transgenic animal models, and animal cells of amyloid diseases may be used as in vivo and in vitro screening tools to aid in the identification of lead therapeutics for the amyloidoses and for the treatment of clinical manifestations associated with these diseases. The successful overproduction of perlecan in transfected cells also serves as a new means to isolate perlecan which will meet the increasing demands for use of perlecan for a variety of in vitro and in vivo assays.

In one embodiment, it is an object of the present invention to provide a transgenic animal or transfected cell line whose cells include a recombinant DNA sequence coding for ubiquitous or cell type specific expression of perlecan or analogs thereof. The mating of perlecan transgenic mice with transgenic mice overexpressing a specific amyloid protein or its precursor, or which overproduce another component implicated in the disease, will produce new transgenic mice progeny which overexpress both perlecan and a specific amyloid protein (or its precursor), or both perlecan and a specific amyloid co-component. These transgenic animals which overexpress both perlecan and a specific amyloid protein (or its precursor protein), or both perlecan and a specific amyloid co-component will lead to the production of new transgenic animals which display much or all of the pathology associated with a particular amyloid disease. In addition, perlecan overexpressing transgenic animals may be mated with transgenic animals which underexpress a specific amyloid protein or its precursor, or which underproduce another component implicated in the disease. The production of these new animals will be effective for the study of the etiology of various amyloidoses and the efficacy of drugs in treating each of the amyloid diseases. The amyloid diseases include, but are not limited to, the amyloid associated with Alzheimer's disease, Down's syndrome and hereditary cerebral hemorrhage with amyloidosis of the Dutch type (wherein the specific amyloid is referred to as beta-amyloid protein or Aβ), the amyloid associated with chronic inflammation, various forms of malignancy and Familial Mediterranean Fever (wherein the specific amyloid is referred to as AA amyloid or inflammation-associated amyloidosis), the amyloid associated with multiple myeloma and other B-cell dyscrasias (wherein the specific amyloid is referred to as AL amyloid), the amyloid associated with type II diabetes (wherein the specific amyloid is referred to as amylin or islet amyloid), the amyloid associated with the prion diseases including Creutzfeldt-Jakob disease, Gerstmann-Straussler syndrome, kuru, and animal scrapie (wherein the specific amyloid is referred to as PrP amyloid), the amyloid associated with long-term hemodialysis and carpal tunnel syndrome (wherein the specific amyloid is referred to as beta$_2$-microglobulin amyloid), the amyloid associated with senile cardiac amyloid and Familial Amyloidotic Polyneuropathy (wherein the specific amyloid is referred to as prealbumin or transthyretin amyloid), and the amyloid associated with endocrine tumors such as medullary carcinoma of the thyroid (wherein the specific amyloid is referred to as variants of procalcitonin).

One of the major problems in the past in trying to produce perlecan transgenic mice and perlecan transfected cells was the large size of the perlecan core protein (~400 kDa). A unique strategy had to be developed which allowed one to produce a single 12 kb (from mouse) cDNA clone that encoded for the entire 400 kDa perlecan core protein. Another object of the present invention is to develop a construction strategy using unique restriction sites in overlapping cDNA clones to produce a single 12 kb cDNA clone that encodes for the entire perlecan core protein.

Another object of the present invention is to provide a method to produce new transgenic animals that overexpress both perlecan (or portions thereof) and a specific amyloid protein (or its precursor), or both perlecan and a specific amyloid co-component. These new transgenic animals can be used for the studies pertaining to the etiology of various amyloidoses and the efficacy of drugs in treating each of the amyloid diseases.

Another object of the present invention is to provide transgenic animals which have in their cells unique promoter/coding sequences which can either ubiquitously express perlecan in all types of tissue, or which can express perlecan in specific types of tissue. These perlecan transgenic animals can be used to assess the role that perlecan, and/or portions thereof, play in development and in a number of relevant biological and/or pathological processes.

A further object of the invention relates to the synthesis and use of promoter/coding constructs which express perlecan alone or in combination with specific amyloid proteins (or precursor proteins), or other amyloid co-components, in various tissues of transgenic animals incorporating such constructs in their genome. A feature of the transgenic animals which would coexpress both perlecan and a specific amyloid protein, or both perlecan and a specific amyloid co-component, will be that these new animals will provide both prognostic and diagnostic means for the study of different amyloid diseases and for determining the efficacy of pharmaceutical drugs in treating specific amyloidoses in a human subject. Initially, the transgenic animals may be used as in vivo screening tools to help identify one or more candidate compounds capable of disrupting the formation, deposition, accumulation and/or persistence of a given amyloid protein which is associated with a predisposition to a specific amyloid disease.

Another object of the present invention relates to providing transgenic non-human mammals which yield information regarding the mechanisms (leading to production and deposition) and location of various amyloids, as well as providing necessary in vivo models for testing of potential drugs capable of interfering with or preventing such formation, deposition, accumulation and/or persistence in specific tissues and organs.

Yet another object of the present invention relates to the production of non-human mammals which overexpress, mouse or human perlecan (and/or any other species from which perlecan cDNA sequence is known or will become known).

Yet another object of the present invention is to provide an animal model for Alzheimer's disease that is constructed using transgenic technology.

It is a further object of the present invention to provide transgenic animals exhibiting one or more histopathologies similar to those of Alzheimer's disease.

It is a further object of the present invention to provide transfected cells expressing one or more Aβ-containing proteins at high levels in cell culture media. It is yet a further object of the present invention to provide transgenic animals expressing one or more Aβ-containing proteins at high levels in brain tissue.

It is a further object of the present invention to provide a method of screening potential drugs for the treatment of Alzheimer's disease using transgenic animal models and transfected cell lines.

Yet another object of the present invention relates to the production of mouse and/or human (or any other species from which the perlecan cDNA sequence is known or will become known) perlecan by transfected cells. This invention serves as a new means to provide for cell culture models for testing of potential drugs capable of interfering with or preventing Aβ or βPP (and constituents thereof) formation, deposition, accumulation and/or persistence. In addition, these cell cultures can be utilized to isolate perlecan in sufficient quantities for use in a variety of different in vitro and in vivo assays.

This invention can be used either alone or in combination with other transgenic animals or transfected animal cells which overproduce or underproduce a given amyloid protein or its precursor, or which overproduce or underproduce another component implicated in a given amyloid disease. As an example, a double transgenic mouse has been made which carry the transgenes for both perlecan and the C-terminal 99 amino acids of the beta-amyloid precursor protein of Alzheimer's disease. These model systems provide new in vivo and in vitro methods for the screening and evaluation of potential drugs for the treatment of Alzheimer's disease and other amyloid diseases, and for the production of perlecan in culture for use in biological systems.

Before the processes for making and using such transgenic mice and transfected cells are described, it is to be understood that these inventions are not limited to particular processes and materials described as such methods and materials, may vary. It is also to be understood that the terminology used herein is for the purpose of describing particular embodiments only, and is not intended to be limiting.

A unique feature of the present invention is the strategies employed to produce a single 12 kb cDNA clone that encodes for mouse perlecan's 400 kDa core protein. The initial cDNA clones to murine perlecan were isolated from an expression vector library prepared from Engelbreth-Holm-Swarm (EHS) tumor mRNA by screening the library with rabbit antibodies to murine perlecan. The authenticity of the clones was confirmed by demonstrating an exact match of amino acid sequences from perlecan peptides with that of sequence deduced from the CDNA clones. Additional cDNA clones were obtained by making primer extension libraries and screening them with existing clones to produce 7 overlapping clones covering perlecan's 12 kb message. These overlapping clones were then ligated together using unique restriction sites in the overlapping regions to produce a single 12 kb cDNA clone that encoded for perlecan's ~400 kDa core protein. The single 12-kb perlecan cDNA was cloned into the NotI/XbaI sites of pBluescript II SK (Stratagene Cloning System) to generate pBSDI-V.

Another unique feature of the transgenic mice of the present invention relates to including general or cell specific promoters in front of sequences which encode for domains I to V of mouse or human perlecan. The ability of the transgenic mice to selectively express perlecan core protein, including any fragments thereof, distinguishes the present transgenic mice from others.

The cloned recombinant and/or synthetic DNA sequences used in connection with the present invention are sequences which encode a biologically active, refolded proteoglycan, and contains one or more glycosaminoglycan chains attached to its protein core backbone.

Construction of Expression Vectors

Figure 2A:
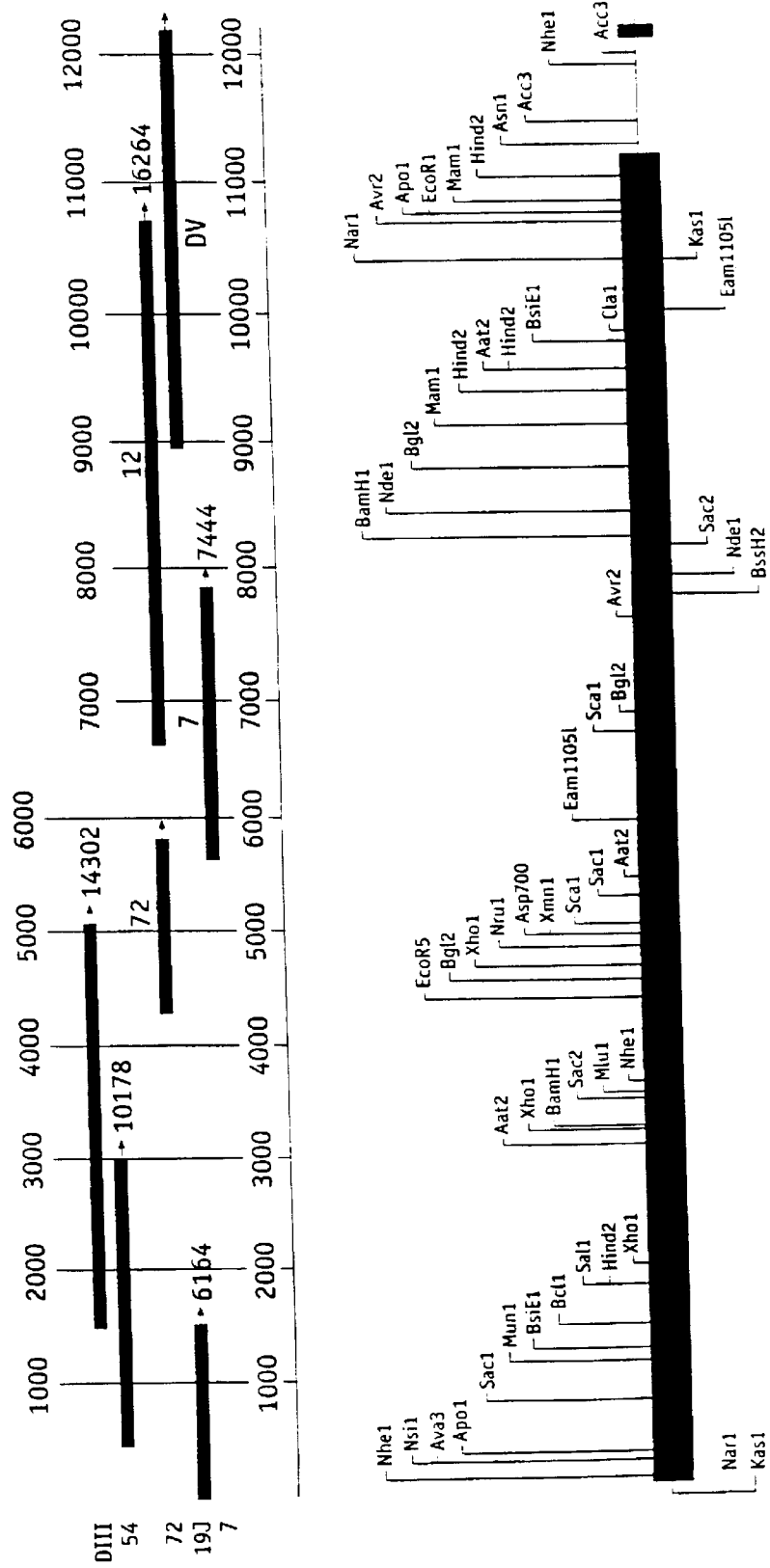
FIGS. 2A–2G are schematics showing the construction strategy of the full-length cDNA for perlecan core protein using plasmid clones containing cDNAs for overlapping parts of perlecan.
Figure 2B:
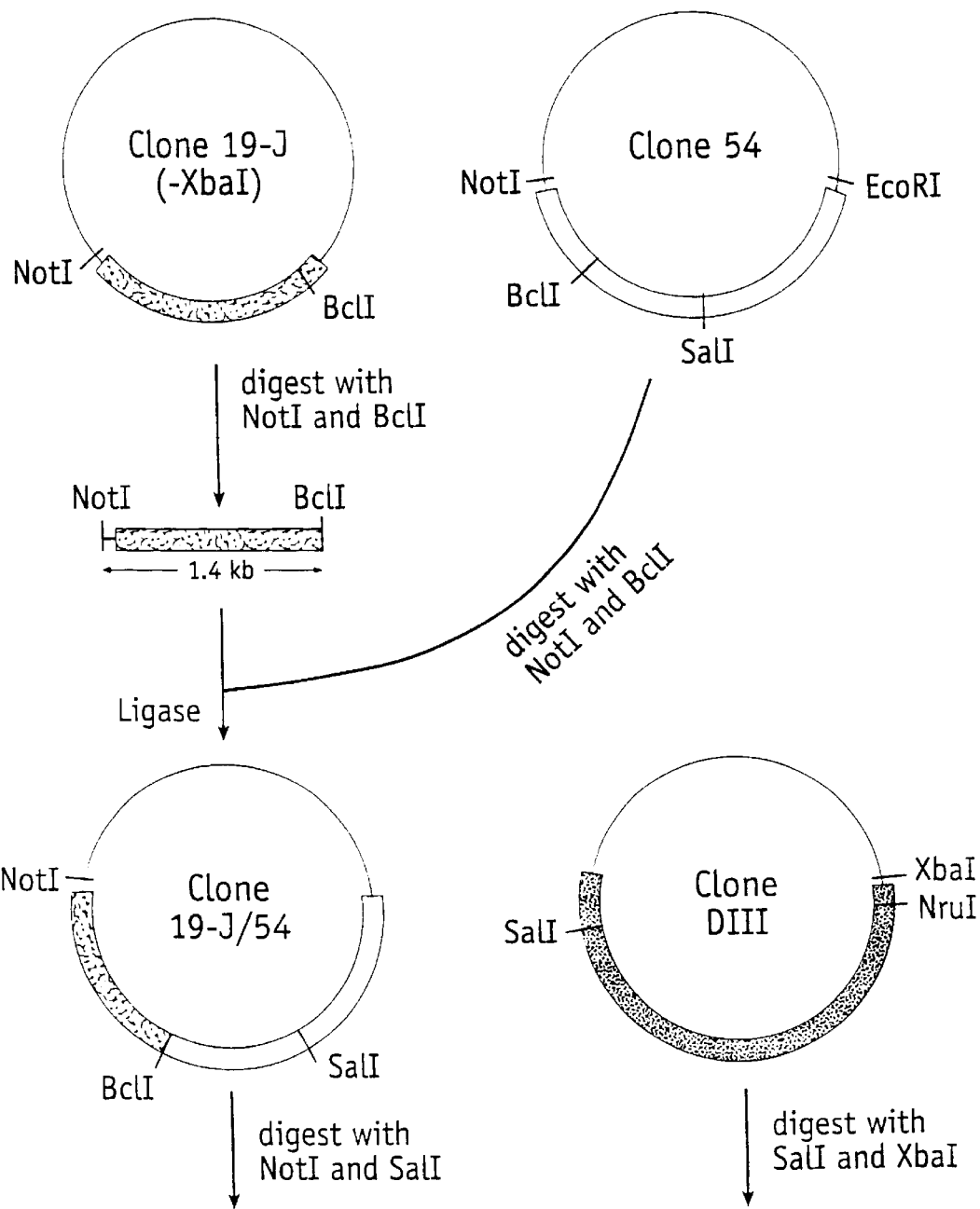
Figure 2C:
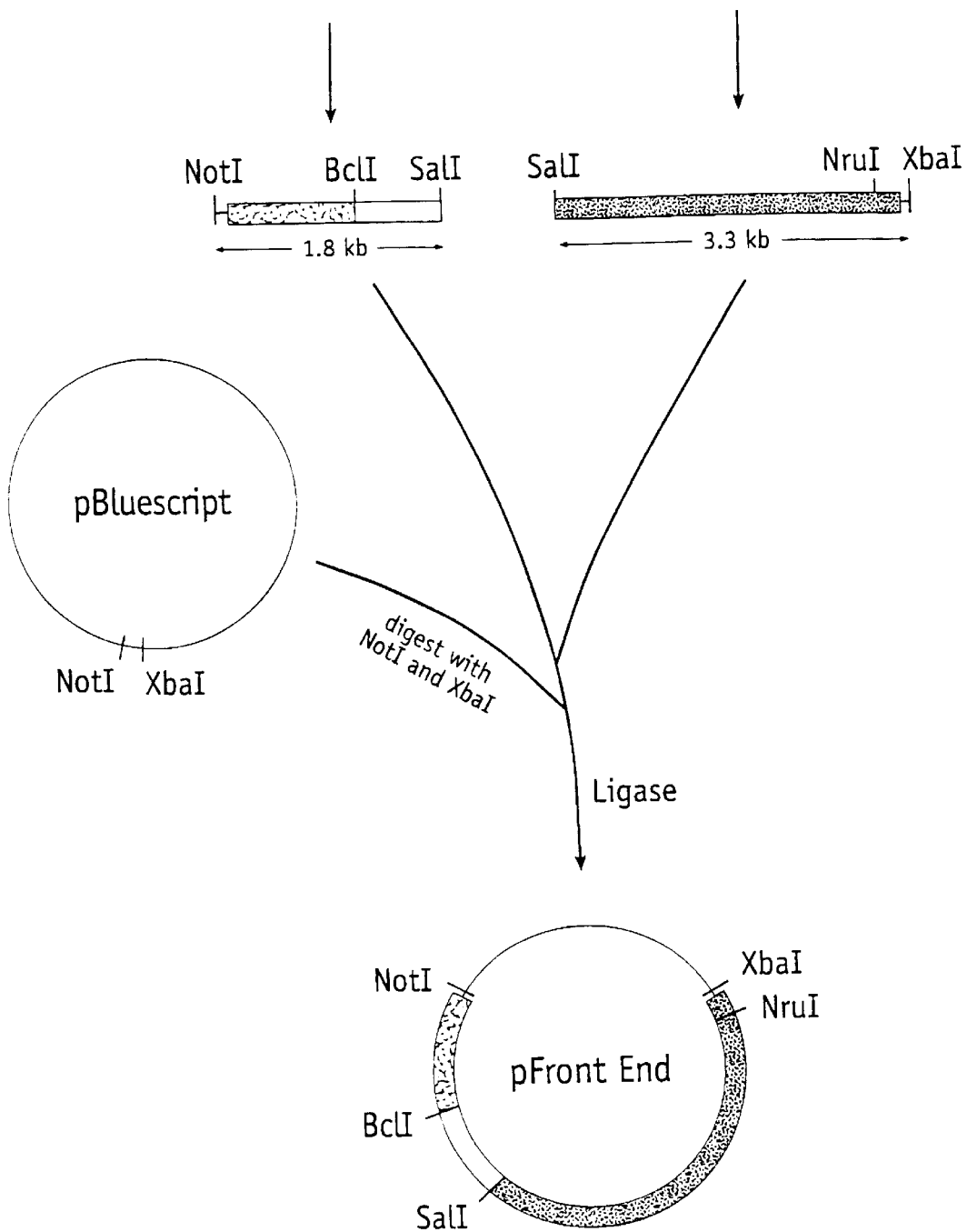
Figure 2D:
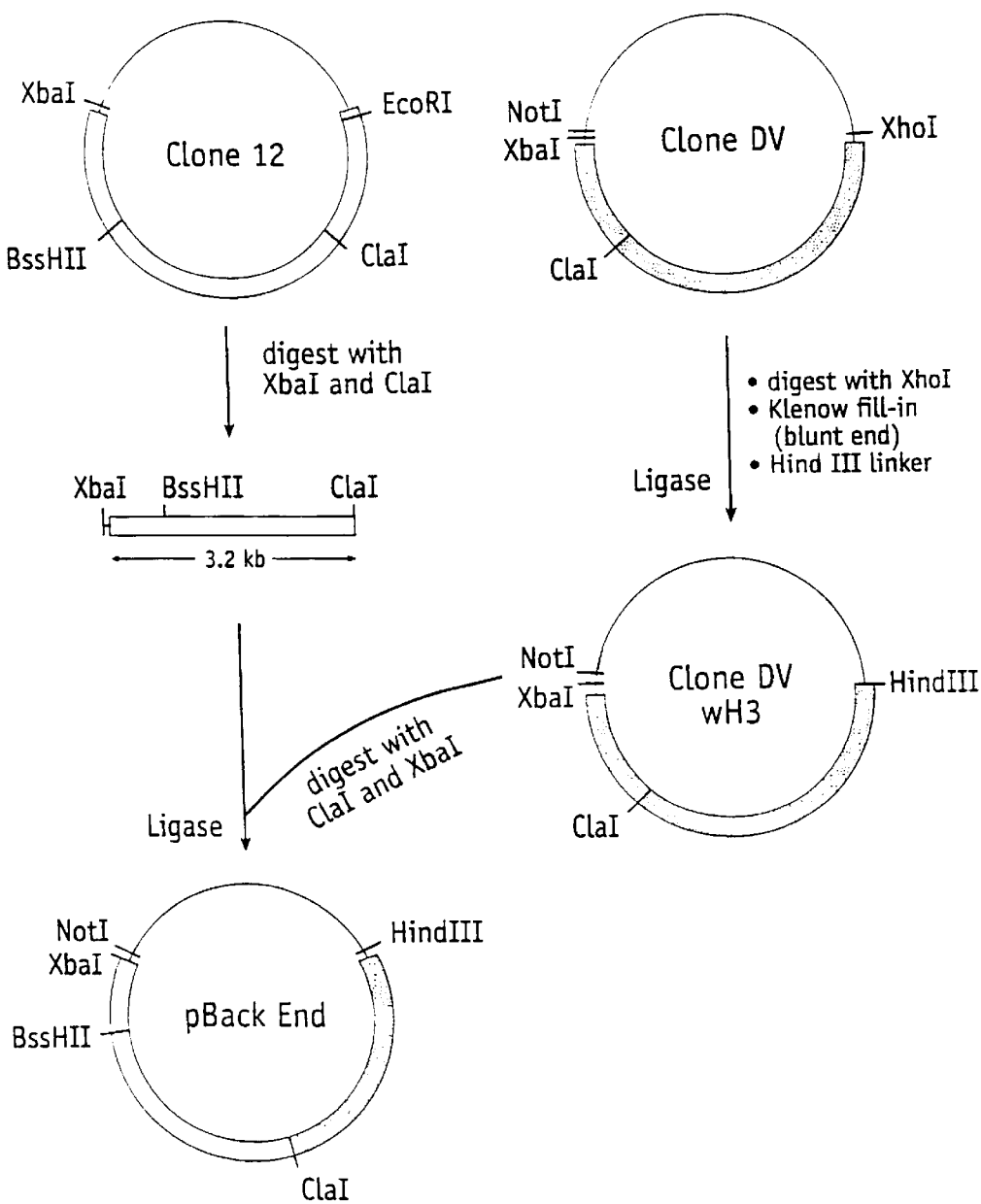
Figure 2E:
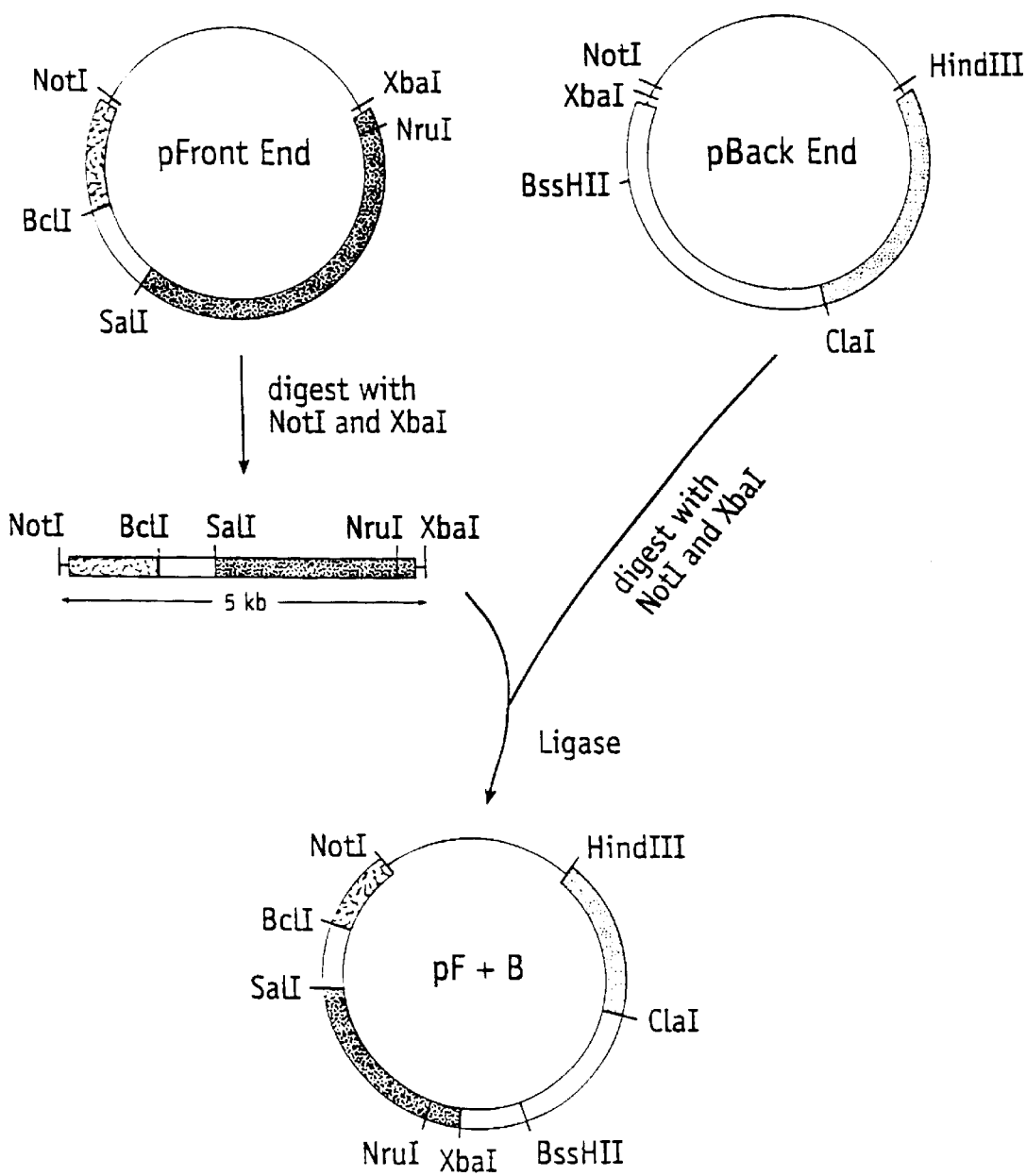
Figure 2F:
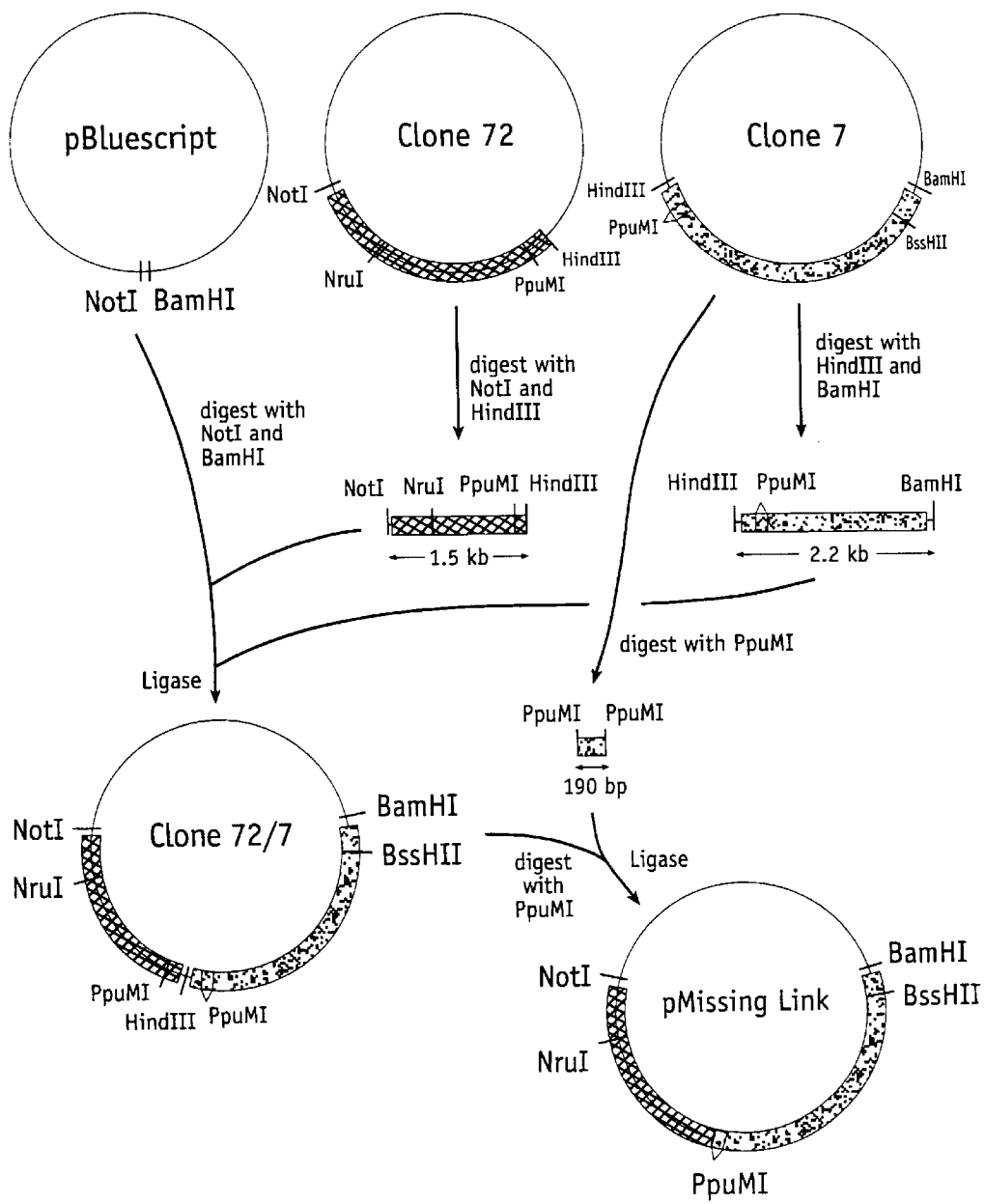
Figure 2G:
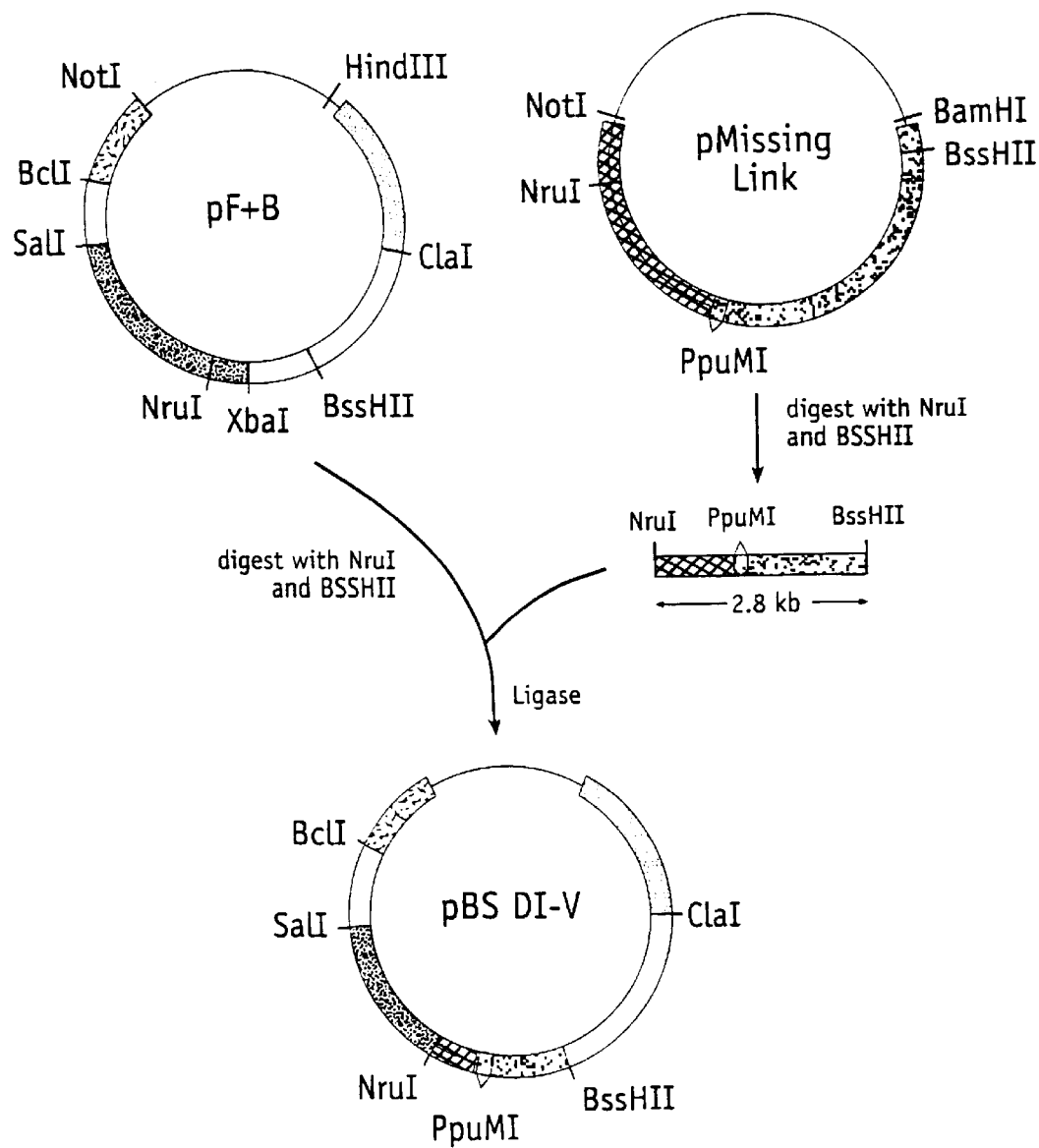

Preferred cDNA clones used in making the transgenic mice and transfected cells include coding sequences which are initially inserted in a suitable expression vector for replication and to confirm production of protein. In a preferred embodiment, a full-length cDNA of murine perlecan core protein is constructed from cDNAs for overlapping parts of perlecan isolated from mouse cDNA libraries (Noonan et al., *J. Biol. Chem.* 266:22939–22947 (1991)). Such clones are in the pBluescript I vector (a product of Strategene) and are illustrated in FIGS. 2A–2G. All clones constructed as described below were verified by sequencing and/or restriction mapping. Firstly, a plasmid (p Front End) containing cDNA for the domains I, II and III of perlecan is constructed from clone 19-J (-XbaI), clone 54 and Clone DIII (FIG. 2B and 2C). The 1.4-kilobase Not I/Bcl I DNA fragment is isolated from clone 19-J (XbaI) and cloned into the NotI and Bcl I sites of clone 54 to produce clone 19-J/54 (FIG. 2B). The 1.8-kilobase Not I/Sal I DNA fragment is isolated from clone 19-J/54 and ligated onto the Sal I site of the 3.3-kilobase Sal I/Xba I fragment isolated from clone DIII. The resulting 5.1-kilobase Not I/Xba I fragment is cloned into the Not I and Xba I site of pBluescript I to produce clone pFront End (FIG. 2C). Secondly, a plasmid clone (p Back End) containing cDNA for most of domain IV of perlecan and all of domain V, is constructed from clone DV and clone 12 (FIG. 2D). To introduce a Hind III site into clone DV, the XhoI site in clone DV is replaced with a Hind III site using Hind III linkers to produce clone DV wH3. The 3.2-kilobase Xba I/Cla I fragment isolated from clone 12 is cloned into the XbaI/Cla I sites of clone DV with H3 from which the smaller Xba I/Cla I fragment is previously removed. The resulting clone is designated p Back End (FIG. 2D). Thirdly, the Front and Back Ends are connected together to produce clone pF+B that contains cDNA for the entire core protein of perlecan except for a small region in the N-terminal part of domain IV (FIG. 2E). The 5.0-kilobase Not I/Xba I fragment isolated from p Front End is cloned into the same restriction enzyme sites of p Back End to produce p F+B (FIG. 2E). Next, a plasmid (p Missing Link) containing cDNA for the small region of the N-terminal part of perlecan domain IV is constructed from clone 72 and clone 7 (FIG. 2F). The 1.5-kilobase Not I/Hind III fragment isolated from clone 72 and the 2.2-kb Hind III/Bam HI fragment isolated from clone 7 are cloned into the Not I and Bam HI sites of pBluescript I to produce clone 72/7 (FIG. 2F). The 190-base pair Ppu MI fragment isolated from clone 7 is inserted into the same restriction enzyme site of clone 72/7 from which the smaller Ppu MI fragments are previously removed. The resulting plasmid is designated as p Missing Link (FIG. 2F). Finally, cDNA in p Missing Link is inserted into pF+B to produce pBS DI-V that contains a full-length cDNA for perlecan (FIG. 2G). The 2.8-kilobase Nru I/Bss HII fragment isolated from p Missing Link is cloned into the same restriction sites of pF+B from which the smaller Nru I/Bss HII fragment is previously removed. The resulting plasmid is designated pBS DI-V (FIG. 2G).

Figure 3A:
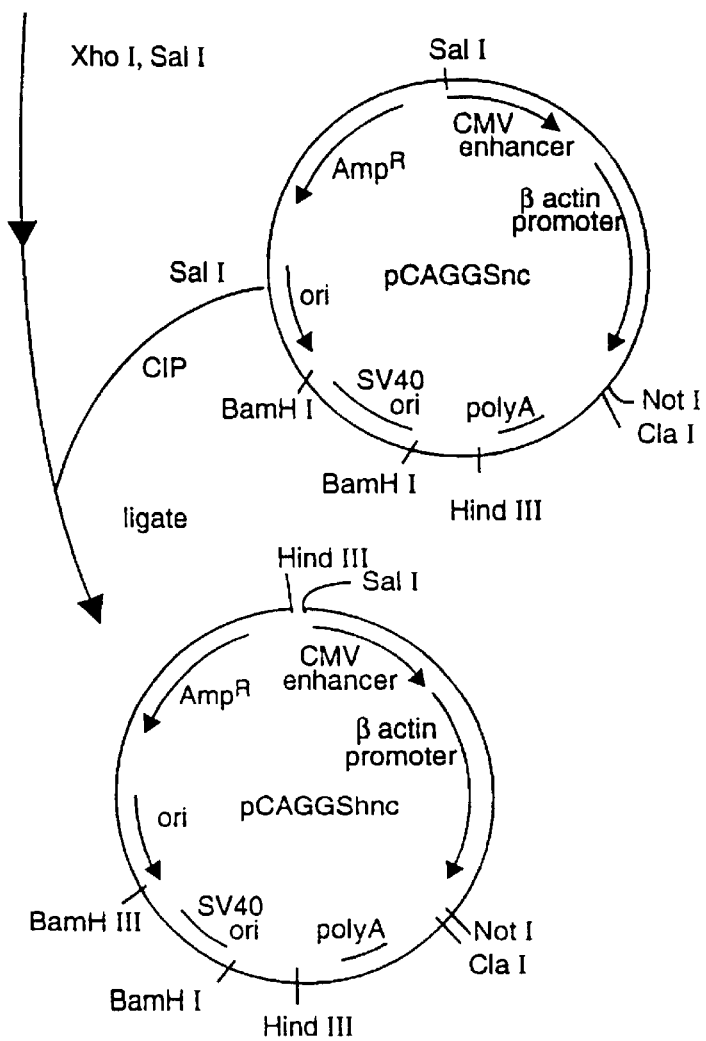
FIGS. 3A–C shows the construction strategy for the cytomegalovirus enhancer/chick β-actin promoter linked to the expression vector pCA-DI-V used to overexpress mouse perlecan in transgenic mice and in transfected cells (SEQ ID NO: 1, SEQ ID NO: 2, SEQ ID NO: 3 and SEQ ID NO: 4).
Figure 3B:
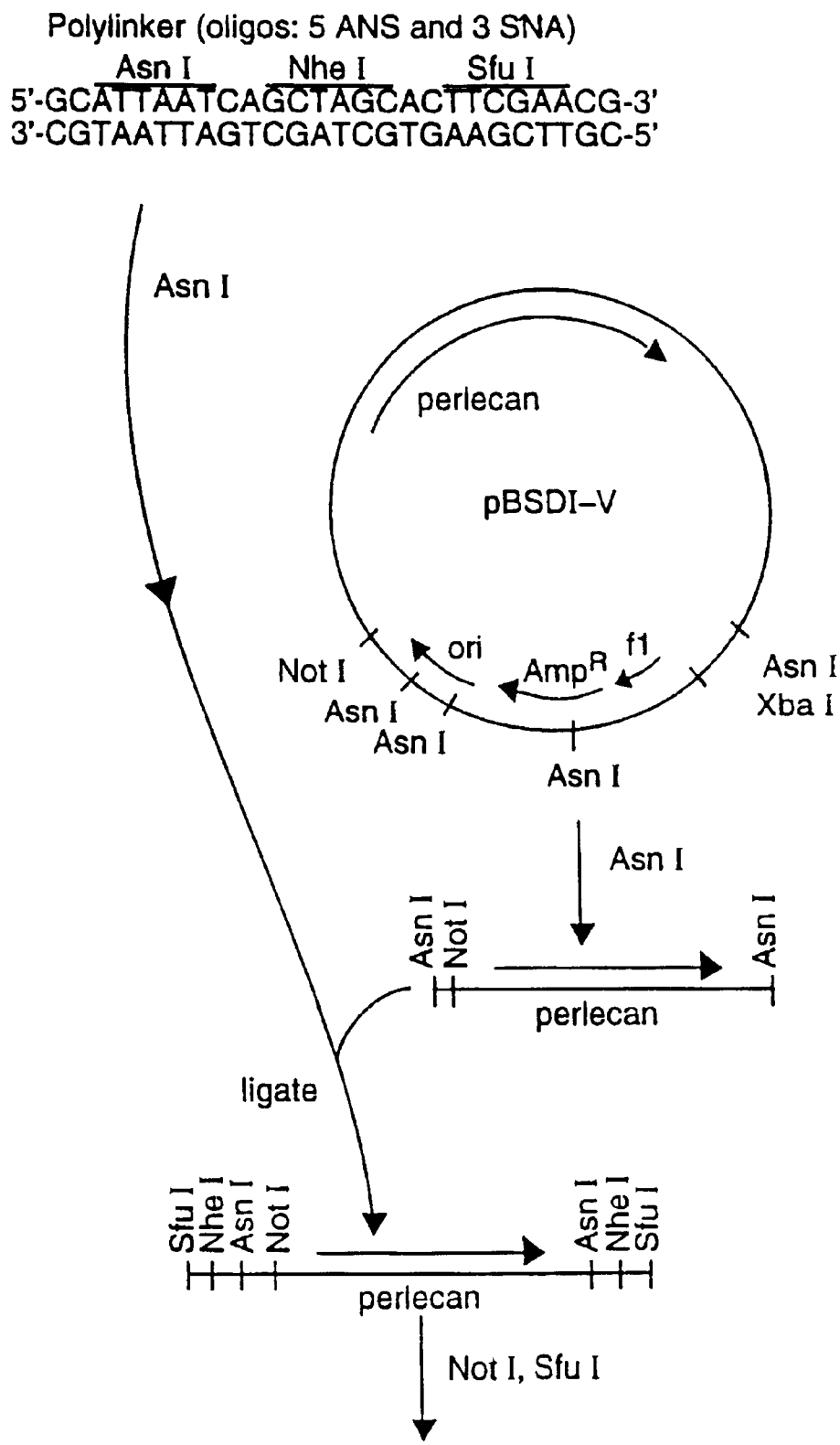
Figure 3C:
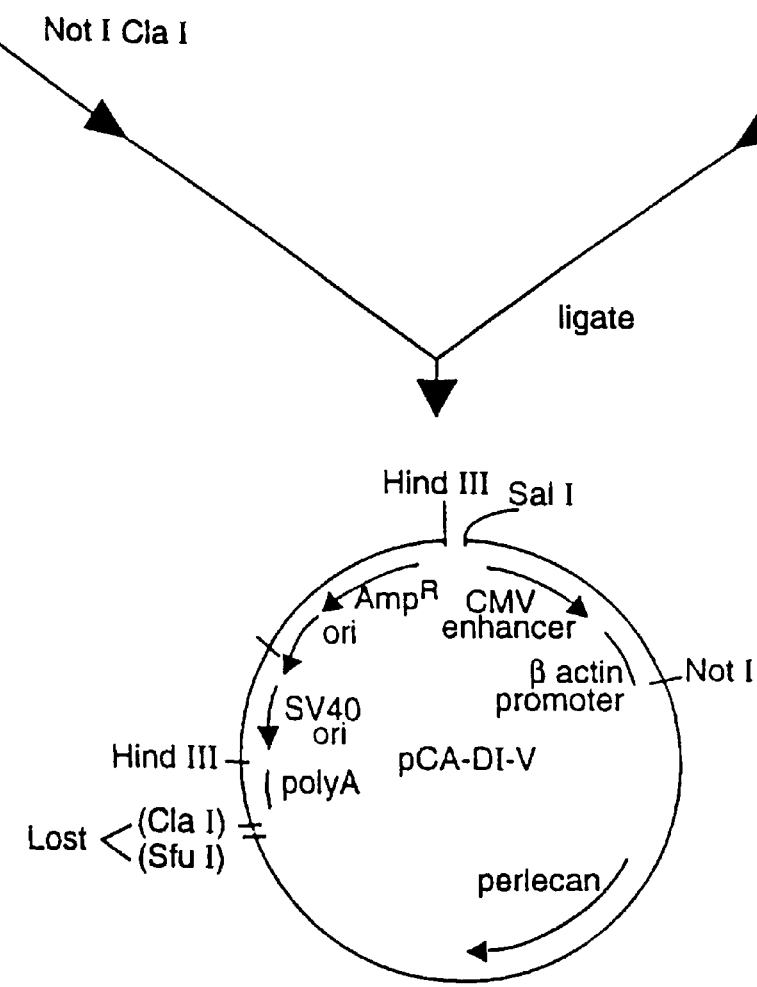

The expression vector, pCA-DI-V, is then constructed to overexpress the entire perlecan core protein under the control of a cytomegalovirus enhancer and a chick beta-actin promoter (FIGS. 3A–3C). This expression vector contains intron 1 of chick β-actin gene and intron 3 of rabbit β-globulin gene. First, a Hind III restriction enzyme site is added next to the Sal I site in pCAGGSnc (Fukuchi et al., *Exp. Exp. Neurol.* 127:253–264 (1994)) using a polylinker containing XhoI, Hind III, and Sal I sites (FIG. 3A). pCAGGSnc is linearized by Sal I digestion and treated with calf intestinal alkaline phosphatase. The polylinker containing XhoI, Hind III, and Sal I sites is digested with Xho I and Sal I and ligated onto the Sal I site of pCAGGSnc to create pCAGGhnc. In a separate reaction, pBSDI-V which contains full length perlecan cDNA in pBluescript II SK (Stratagene Cloning System) is digested with Asn I and a 11.5-kb DNA fragment containing perlecan cDNA is isolated (FIG. 3B). A polylinker containing Asn I, Nhe I, and SfuI sites is digested with AsnI and ligated onto the same restriction enzyme site of the isolated 11.5-kb DNA fragment (FIG. 3B). The isolated fragment is then digested with Not I and Sfu I and ligated onto the Not I and Cla I sites of pCAGGShnc which was previously cut with Not I and Cla I (FIG. 3C). Cla I is compatible with Sfu I. The resulting vector is designated as pCA-DI-DV; pCA-DI-V is used to establish lines of transgenic mice and cells.

In another preferred embodiment, a full-length cDNA of human perlecan core protein can be constructed from cDNAs for overlapping parts of perlecan isolated from human cDNA libraries. As demonstrated by Murdoch et al., (*J. Biol. Chem.* 267:8544–8557 (1992)), commercially available cDNA libraries such as human colon cDNA library (HL103b, a product of Clontech), or cDNA libraries prepared from a human fibroblast cell line (CRL 1262, available from American Tissue Culture Collection) and a human amnion cell line (WISH also available from American Tissue Culture Collection) can also be used to isolate overlapping clones covering the entire coding sequence for human perlecan core protein. These overlapping clones can be ligated to form a single cDNA using appropriate restriction sites in the clones in any manner known to those skilled in the art. The single 14kb cDNA clone is then cloned into multiple cloning sites of pCAGGS or pCAGGShnc to create an expression vector for human perlecan. Expression vectors are not limited to pCAGGS or pCAGGShnc. Indeed, any other expression vectors containing the promoters listed below (or any other promoters that seem appropriate by those skilled in the art) can be used and the construction of these expression vectors can be achieved in any manner known to those skilled in the art.

In another preferred embodiment, a full-length cDNA of bovine perlecan core protein can be similarly constructed and can be used to overexpress bovine perlecan in transgenic mice and in cultured cells. For example, bovine perlecan cDNA can be isolated by screening a bovine kidney cDNA library (BL3001b, a product of Clontech) using several parts of mouse cDNA as probes. The isolated overlapping clones can be ligated into a single cDNA coding for the entire bovine perlecan and then cloned into any expression vectors, in any manner known to those skilled in the art.

Promoter/Perlecan Sequence Fusion Constructs
A) Promoters that Permit Ubiquitous Expression of Transgenes The following promoters allow transgenes to express at high levels in virtually all tissues. Therefore such ubiquitous promoters can be used to make any type of amyloid animal models. Such useful promoters which can be used to create constructs and inserted into transgenic animals in connection with the present invention include, but are not limited to:

Beta-actin Promoter

Beta actin is essential and abundantly expressed in virtually all cells. pCAGGS (Niwa et al., *Gene* 108:193–200 (1991)) that contained the beta-actin promoter was used to construct expression vectors for mouse perlecan and beta-amyloid precursor protein as in Example 10.

RNA Polymerase I Promoter

RNA polymerase I catalyzes synthesis of ribosomal RNA. Therefore, this promoter permits transgene expression in virtually all tissues with the exception of erythrocytes. RNA polymerase I transcripts, however, are poorly translated as MRNA since they retain a triphosphate at their 5' termini rather than receiving a trimethyl G cap. In the absence of a trimethyl G cap, ribosomes appear not to recognize the transcript as message and translation initiation is impaired. Insertion of an internal ribosome entry site (IRES) into the 5' leader of the RNA polymerase I transcript allows high level protein production under control of the RNA polymerase I promoter (Palmer et al., *Nucleic Acid Res.* 21:3451–3457 (1993)). Such RNA polymerase promoters with IRES are available in the plasmid, pMENA (Palmer et al., *Nucleic Acid Res.* 21:3451–3457 (1993)).

RNA Polymerase II Promoter

RNA polymerase catalyzes the synthesis of RNA transcription from genes and therefore its promoter permits the ubiquitous expression of transgenes with the exception of erythrocytes. The RNA polymerase II promoter is cloned in pHBII CATm (Ahearn et al., *J. Biol. Chem.* 262:10695–10705 (1987)).

Polypeptide Chain Elongation Factor 1-alpha promoter

Polypeptide chain elongation factor 1-alpha (EF-1-alpha) promotes the GTP-dependent binding of an aminoacyl-tRNA to ribosomes. EF-1-alpha is one of the most abundant proteins in eukaryotic cells and expressed in all kinds of mammalian cells. An expression vector, pEF-BOS, containing EF-1-alpha promoter has been constructed and demonstrated to be a strong ubiquitous promoter (Mizushima and Nagata, *Nucleic Acids Res.* 18:5322 (1990)).

B) Promoters that Restrict Expression to Specific Tissues

Other useful promoters may also be used to produce perlecan transgenic animals which may prove useful for the ultimate development of new transgenic animals that mimic the amyloid diseases. Some useful promoters which can also be used to create constructs and inserted into transgenic animals in connection with the present invention include, but are not limited to:

Platelet-Derived Growth Factor (PDGF) Promoter

This promoter has recently been used to produce transgenic mice that overexpress the beta-amyloid precursor protein and that deposit fibrillar beta-amyloid protein deposits in an extracellular location (Games et al., *Nature* 373:523–527 (1995)). It is possible that when perlecan expression is driven by a PDGF promoter, these resulting transgenic mice may prove more useful for the ultimate development of a transgenic mouse model for Alzheimer's disease and Down's syndrome (i.e. beta-amyloid protein) amyloidosis. A plasmid, psisCAT6a, that contains the PDGF-β chain promoter is available (Sasahara et al., *Cell* 64:217 (1991)).

Neurofilament M or L Promoters

These promoters demonstrate a high level of expression and are found in connection with the most abundant neural protein. They are characterized by central nervous system/peripheral nervous system neuronal-specific expression. The mouse gene for this promoter is a published sequence and the isolation of the promoter region is necessary in order to use the promoter in connection with the present invention. The neurofilament L promoters (Begemann et al., *Proc. Natl. Acad. Sci. USA* 87:9042–9046 (1990)) and M promoters (Begemann et al., *Mol. Brain Res.* 15:99–107 (1992)) have been characterized and are available.

Glial Fibrillary Acidic Protein (GFAP) Promoters

Such promoters are characterized by murine specificity and CNS/PNS glial-specific expression. The promoter has been characterized and is available (Balcarek et al., *Nucleic Acids Res.* 13:5527–5543 (1985)).

Methallothionein III (MT-III) Promoters

MT-III is a third member of the methallothionein gene family and its expression appears to be restricted to brain in mice. MT-III is abundant in human brain and is immunohistochemically localized to astrocytes in the grey matter (Uchida et al., *Neuron* 7:337–347 (1991)). In the Alzheimer's disease cortex, the number of MT-III positive astrocytes are drastically reduced and this reduction is highly correlated with the abundance of neurofibrillary tangles and curly fibers (Uchida et al., *Neuron* 7:337–347 (1991)). The involvement of astrocytes in beta-amyloid protein amyloidosis as observed in Alzheimer's disease has been previously suggested (Potter et al., *Prog. Brain Res.* 94:447–458 (1992)). The MT-III promoter has been cloned and characterized (Palmiter et al., *Proc. Natl. Acad. Sci. USA* 89:6333–6337 (1992)).

Prion Protein Promoter

This promoter has been shown to drive position-independent copy number-dependent transgene product expression in the mouse brain (Scott et al., *Cell* 59:847–857 (1989); Prusiner et al., *Cell* 63:673–686 (1990)). This promoter was also used to create transgenic mice that overexpress the beta-amyloid precursor protein (Hsiao et al., *Neuron* 15:1203–1218 (1995)).

Insulin Promoter

The insulin promoter can be used for the development of a transgenic mouse model to mimic islet amyloidosis as observed in patients with type II diabetes (Verchere et al., *Proc. Natl. Acad. Sci. USA* (in Press) (1996)). The insulin promoter can be used to achieve the specific expression of transgene in beta-cells (Sarvetnick et al., *Cell* 52:773–782 (1988)). The human insulin promoter has been characterized and is available.

Neuron-Specific Enolase Promoter

This promoter directs the neural-specific expression of a reporter gene in transgenic mice (Fross-Petter et al., *Neuron* 5:187–197 (1990)) and has been used to make transgenic mice which overexpress the beta-amyloid precursor protein (Quon et al., *Nature* 352:239–241 (1991)).

Low-affinity Nerve Growth Factor Receptor (p75) Promoter p75 is mainly expressed in central and peripheral cholinergic neurons. The activity of p75 promoter has been tested in cultured neurons (Taiji et al., *Mol. Cell. Biol.* 12:2193–2202 (1992)). Since loss of cholinergic neurons in brain represents an important feature of Alzheimer's disease, this promoter can be useful to create such models.

Methallothionein I Promoter

This promoter was used to create transgenic mice that produce a mutant form of human transthyretin as a potential model for type I familial amyloidotic polyneuropathy (Yi et al., *Am. J. Path.* 138:403–412 (1991)). These mice develop amyloid deposits in the gastrointestinal tract, cardiovascular system, and kidney, but not in the peripheral nervous system where amyloid deposition occurs in humans. Therefore, this promoter may be effective for producing perlecan transgenic mice and/or transgenic mice which overexpress both perlecan and transthyretin, for a new animal model of prealbumin/transthyretin amyloidosis.

Other known promoters that are tissue specific may also be used to produce animal models of amyloidoses affecting specific organ systems. Such promoters can be used by those skilled in the art. In addition, new promoters may become available which may be also used by those skilled in the art to drive the expression within desired tissues or organs for the ultimate production of amyloid transgenic mice.

It is understood that modifications which do not substantially affect the activity of various embodiments of this invention are also included within the definition of the invention provided herein. Accordingly, the following examples are intended to illustrate but not limit the present invention.

EXAMPLE 1

Expression of Domains I–V of Murine Perlecan in COS and P19 Cells

To facilitate the expression of murine perlecan in mammalian cells, the expression vector, designated pCA-DI-V was transfected into an African green monkey kidney cell line (COS), and into embryonic carcinoma cells (P19 cells) which upon stimulation with the appropriate amount of retinoic acid differentiate into neuron-like cells. This transfection was done by liposome-mediated gene transfer (Lipofectamine, a product of Life technologies) according to the manufacturer's protocol. The neomycin-resistance gene that confers G418-resistance was also transfected together with the pCA-DI-V vector. By screening the transfected cells with G418, 20 clones for each cell line (COS and P19 cells) were isolated and subjected to Western blot analysis to determine the levels of perlecan expression. More precisely, COS-7 cells (African green monkey kidney cell line; available from American Tissue Culture Collection, ATCC# CRL-1651) and P19 cells (Rudnicki and McBurny in *Teratocarcinoma and Embryonic Stem Cells: A Practical Approach*, IRL Press, Washington, D.C., pp. 19–50, (1987)) were cultured in Dulbecco's modified Eagle's medium (DMEM) containing 10% fetal bovine serum, 100 $\mu$g/ml streptomycin and 100 units/ml penicillin (regular medium). 1–2×10$^5$ cells/60 mm dish were inoculated one day before transfection of DNA. The cells were washed with Opti-MEM I Reduced-Serum Medium (a product of Life Technologies) prior to transfection to remove serum from the culture. Three $\mu$g of pCA-DI-V, 0.1 $\mu$g of pMAMneo (a product of Clontech Laboratories Inc.) and 20 $\mu$l of Lipofectamine were mixed, incubated for 15 minutes at room temperature and added to the cells cultured in Optim-MEM I Reduced Serum Medium. The COS-7 and P19 cells were incubated at 37° C. in a humidified atmosphere of 5% CO$_2$ for 18 and 6 hours, respectively, and Optim-MEM I Reduced-Serum medium was replaced with regular medium. Two days after transfection, the cells were treated with 0.05% trypsin and 530 $\mu$M EDTA and replaced at a concentration of 10,000 cells/100 mm dish with selection medium (regular medium with 800 $\mu$g/ml G418). Two to three weeks after transfection, emerging resistant colonies were isolated using clonal rings and propagated for storage and Western blot analysis. For each cell line, approximately 20 clones were isolated.

EXAMPLE 2

Up-Regulation of Perlecan Levels in Transfected COS and P19 Cells as Revealed by Western Blot Analyses To determine the potential differences in perlecan levels in transfected versus non-transfected COS and P19 cells, the media and cell layers were analyzed by Western blotting with a specific monoclonal antibody (HK-102) against perlecan core protein. From each cell culture dish, the media was collected for analysis as described below, making sure that equal volumes of media were analyzed from either transfected or non-transfected cells. The cell layers were harvested by scraping into urea buffer (urea buffer contained 7 M urea, 0.2 M NaCl, 0.1% (w/v) CHAPS, 50 mM Tris-HCl, pH 8.0, containing a protease inhibitor cocktail including 10 mM EDTA, 10 mM NEM, 10 mM 6-aminohexanoic acid, 5.0 mM benzamidine-HCl, and 1 mM PMSF).

For COS cells, PGs from cell layer and media extracts were then purified by DEAE-Sephacel ion-exchange chromatography. Briefly, cell layer and media extracts were pooled separately, and supplemented with 0.5% Triton X-100 (v/v) and applied to a 1 ml DEAE-Sephacel column packed in a plastic syringe equilibrated with urea buffer (urea buffer contained 7 M urea, 0.2 M NaCl, 0.1% (w/v) CHAPS, 50 mM Tris-HCl, pH 8.0, containing a protease cocktail including 10 mM EDTA, 10 mM NEM, 10 mM 6-aminohexanoic acid, 5.0 mM benzamidine-HCl, and 1 mM PMSF). Proteins and non-PGs were removed by first washing the column with 5 column volumes of urea buffer (described above) containing 1% Triton X-100 and 0.25M NaCl. Bound PGs were then eluted with 5 column volumes of urea buffer containing 3M NaCl. Equal proportions of each sample were then precipitated by adding 3.5 volumes of 95% ethanol, 1.5% potassium acetate (w/v), cooled on dry ice for 1 hour and centrifuged (using an Eppendorf 5415C desktop centrifuge) at 14,000×g for 20 minutes. Samples were then left either undigested, or digested with heparinase/ heparitinase and/or chondroitinase ABC. For heparinase/ heparitinase digestion, samples were suspended in 50 $\mu$l of 0.2M Tris-HCl, 5 mM calcium acetate (pH 7.0) and digested with a mixture of heparinase I, II, and III (i.e. heparitinase) (Sigma Chemical Co.) used at 1U each (approximately 10 mU/$\mu$g protein) in 30 $\mu$l of glycerol:distilled water (1:1). Following addition of 10 $\mu$l of a 10× protease inhibitor cocktail (as described above), heparinase/heparitinase containing samples were incubated overnight at 41° C. and ethanol precipitated (as described above), prior to separation by SDS-PAGE. Samples treated with chondroitinase ABC were digested with 100 mU of chondroitin ABC lyase (ICN Biochemicals) in Tris-buffered solution (50 mM Tris, 50 mM sodium acetate, 10 mM EDTA, and protease inhibitor cocktail as described above, pH 7.5) at 37° C. for 2 hours. Each sample was then heated for 5 minutes in a boiling water bath, loaded onto SDS-PAGE and electrophoresed at 100V for 45 minutes along with pre-stained molecular weight protein standards (a product of Bio-Rad). SDS-PAGE were performed according to the procedure of Laemmli (*Nature* 227:680–685 (1970)) using a Mini-Protean II electrophoresis system with precast 4–15% polyacrylamide gels. Samples were run under non-reducing conditions for use with a monoclonal antibody (HK-102) against perlecan core protein. Following SDS-PAGE, separated proteins were transferred to nitrocellulose using a Mini transblot electrophoresis transfer cell. Electrotransfer was performed at 100V for 2 hours. Following transfer, membranes were rinsed in water and blocked overnight with 0.15% (w/v) bovine serum albumin, 1% (v/v) normal goat serum, 100 mM Tris-HCl, and 3mM NaN$_3$ (pH 7.4). Blots were probed with a monoclonal antibody (HK-102) which recognizes the perlecan core protein, diluted 1:3000 in TBS containing 100 mM Tris-HCl, 50 mM NaCl, 0.05% Tween-20, and 3 mM NaN$_3$ (pH 7.4) (TTBS). Blots were incubated with primary antibody for 3 hours, washed with TTBS three times (10 minutes each), followed by a 1 hour incubation in biotinylated goat-anti-rat Ig's (IgG and IgM) (Jackson Immunoresearch, West Groven, Pa.) diluted 1:1000 with TTBS. The membranes were then rinsed three times (10 minutes each) with TTBS, probed for 30 minutes with avidin alkaline phosphatase conjugate (Vectastain), rinsed again (as described above), followed by the addition of an alkaline phosphatase substrate solution (Vectastain). Following color development, the reaction was stopped by flushing the membranes with double-distilled water. Immunodetection of perlecan core protein using the monoclonal (HK-102) antibody was employed in at least three different cell culture experiments in order to determine reproducibility. For comparisons perlecan was isolated from the Engelbreth-Holm-Swarm tumor as previously described (Castillo et al., *J. Biochem.* 120:433–444 (1996)) and digested with heparinase I, II and III (as described above) prior to Western blotting.

Figure 4:
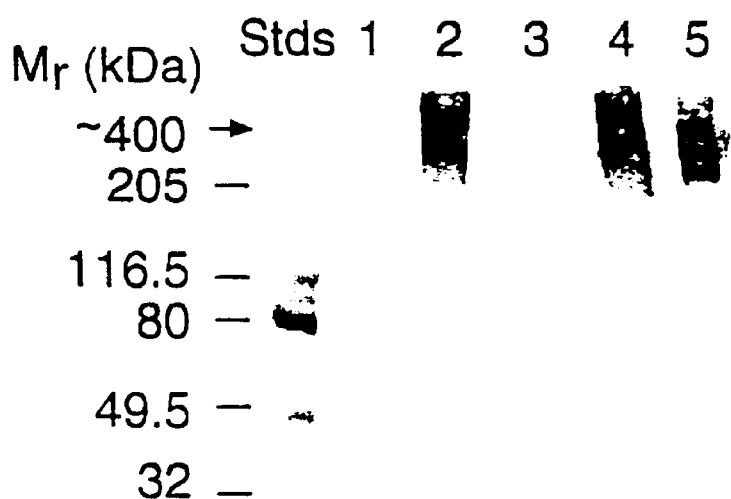
FIG. 4 is a black and white photograph of Western blots from the cell lysates of non-transfected versus transfected COS cells. Overexpression of perlecan in the cell layer of transfected COS cells is demonstrated.

As shown in FIG. 4, Western blot analyses of PGs isolated from the cell layer of non-transfected COS cells demonstrated no immunoreactivity on Western blots probed with a monoclonal antibody (HK-102) which recognizes perlecan core protein (FIG. 4, lanes 1 and 3). On the other hand, western blot analyses of PGs isolated from the cell layer of transfected COS cells overexpressing the entire perlecan core protein, revealed a ~400 kDa band using the monoclonal antibody (HK-102) specific for perlecan core protein (FIG. 4, lane 2 and lane 4). Chondroitinase ABC digestion did not appear to cause a shift in the ~400 kDa band in the cell layer of transfected cells when compared to undigested sample (not shown), suggesting that little to no chondroitin sulfate chains were present on the perlecan core protein produced. On the other hand, a slight shift and/or tighter ~400 kDa band was observed in the cell layer of transfected cells following heparinase/heparitinase digestion (FIG. 4, lane 4 when compared t6 undigested sample (FIG. 4, lane 2), suggesting that the perlecan core protein produced in the cell layer of transfected cells contained heparan sulfate chains that were either shorter or less in number than normal (i.e. perlecan is usually thought to contain 3 glycosaminoglycan chains attached to its core protein). The perlecan core protein band on immunoblots from cell layer of transfected COS cells (FIG. 4, lanes 2 and 4) was similar in position to that of pure perlecan isolated from the Engelbreth-Holm-Swarm tumor (FIG. 4, lane 5). However, whereas isolated perlecan gave a characteristic doublet at ~400 kDa (FIG. 4, lane 5), the cell layer from transfected COS cells demonstrated a single major band at ~400 kDa (FIG. 4, lane 2 and lane 4).

Figure 5:
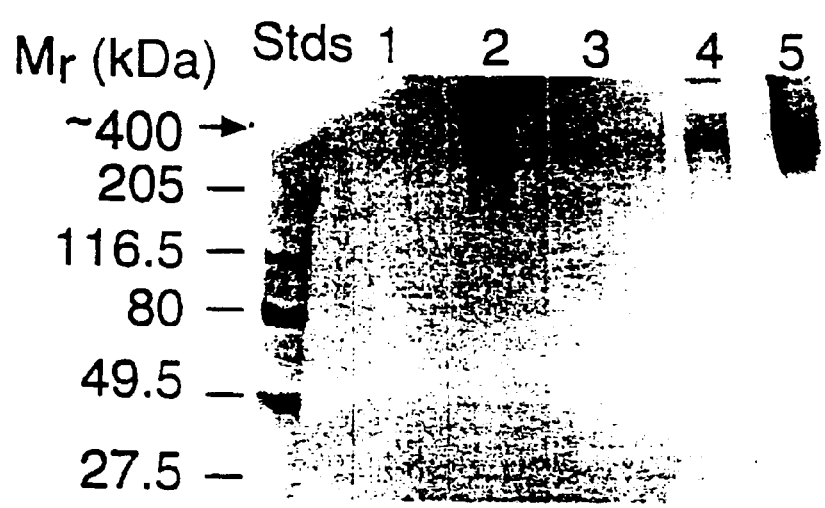
FIG. 5 is a black and white photograph of Western blots from the media of non-transfected versus transfected COS cells. Overexpression of perlecan in the media of transfected COS cells is demonstrated.

Similar results were obtained by Western blot analyses of PGs isolated from the media (FIG. 5) of non-transfected (FIG. 5, lanes 1 and 3) and transfected (FIG. 5, lanes 2 and 4 ) COS cells, when probed with the monoclonal antibody (HK-102) against perlecan core protein. A marked accumulation of perlecan core protein immunoreactivity was observed in transfected COS cells (FIG. 5, lanes 2 and 4) in comparison to non-transfected cells (FIG. 5, lanes 1 and 3). Chondroitinase ABC digestion did not cause a shift in the ~400 kDa band isolated from the media of transfected cells (FIG. 5, lane 4) when compared to undigested sample (FIG. 5, lane 2), suggesting that little to no chondroitin sulfate chains were present on the perlecan core protein secreted. On the other hand, a slight shift and/or tighter ~400 kDa band was observed in the media of transfected cells following heparinase/heparitinase digestion when compared to undigested sample from transfected media (not shown), suggesting that the perlecan core protein produced in the media of transfected cells contained heparan sulfate chains that were either shorter in length or less in number than normal. Perlecan core protein band on immunoblots from media of transfected COS cells (FIG. 5, lanes 2 and 4) was similar in position to that obtained from pure perlecan (FIG. 5, lane 5), and a similar characteristic double band at ~400 kDa was observed in media from transfected COS cells (FIG. 5, lanes 2 and 4).

The fact that the perlecan bound to DEAE-Sephacel for isolation indicated that the perlecan most likely contained glycosaminoglycan chains. Since heparinase/heparitinase digestion, and not chondroitinase ABC caused a slight shift in the position of the ~400 kDa core protein on Western blots of both media and cell layer from transfected COS cells, it suggested that heparan sulfate GAG chains (although shorter in length or less in number than usual) were present on the perlecan core protein of transfected cells. Nonetheless, this study represents the first time that successful transfection of the entire perlecan core protein has been achieved, and represented the first important critical step for the development of perlecan transgenic mice over expressing the entire ~400 kDa core protein.

For P19 cells, following isolation of PGs from cell layer and media, and SDS-PAGE, as described above, the proteins were transferred to PVDF membrane (a product of Millipore) at 260 mA for 18 hours using the Bio-Rad Transblot System. The membranes were blocked with PBS containing 5% nonfat dried milk (w/v), 0.02% sodium azide, and 0.02% Tween 20, then incubated at 4° for 18 hours with primary antibodies (polyclonal or monoclonal antibodies recognizing perlecan core protein) and immunostained with an enhanced chemiluminescence system (a product of Amersham). As found with the overexpression of perlecan core protein in transfected COS cells, the western blot analyses of P19 cell layer and media revealed high levels of perlecan production in transfected cells, whereas non-transfected cells showed little to no immunoreactivity (not shown). These studies confirmed that overexpression of the perlecan core protein could be achieved in transfected COS and P19 cells by the construction strategy used in the present invention.

EXAMPLE 3

Up-Regulation of Secreted Aβ in Media of P19 Cells Overexpressing Both Perlecan and βPP-695

A P19 derived cell clone had previously been established and designated P19 695B2, which overexpresses the 695 amino acid isoform of the human beta-amyloid precursor protein (βPP-695)(Fukuchi et al., *J. Neurochem.* 66:2201–2204 (1996)). In this example, the P19 695B2 cells were transfected with the pCA-DI-V vector, and stable transformants designated P19 695B2 PCB6 and P19 695B2 PCD3, which overexpress both perlecan and βPP-695 were established using the methods described in Example 1. Overexpression of βPP-695 and perlecan was confirmed by western blotting as in Example 2.

Figure 6:
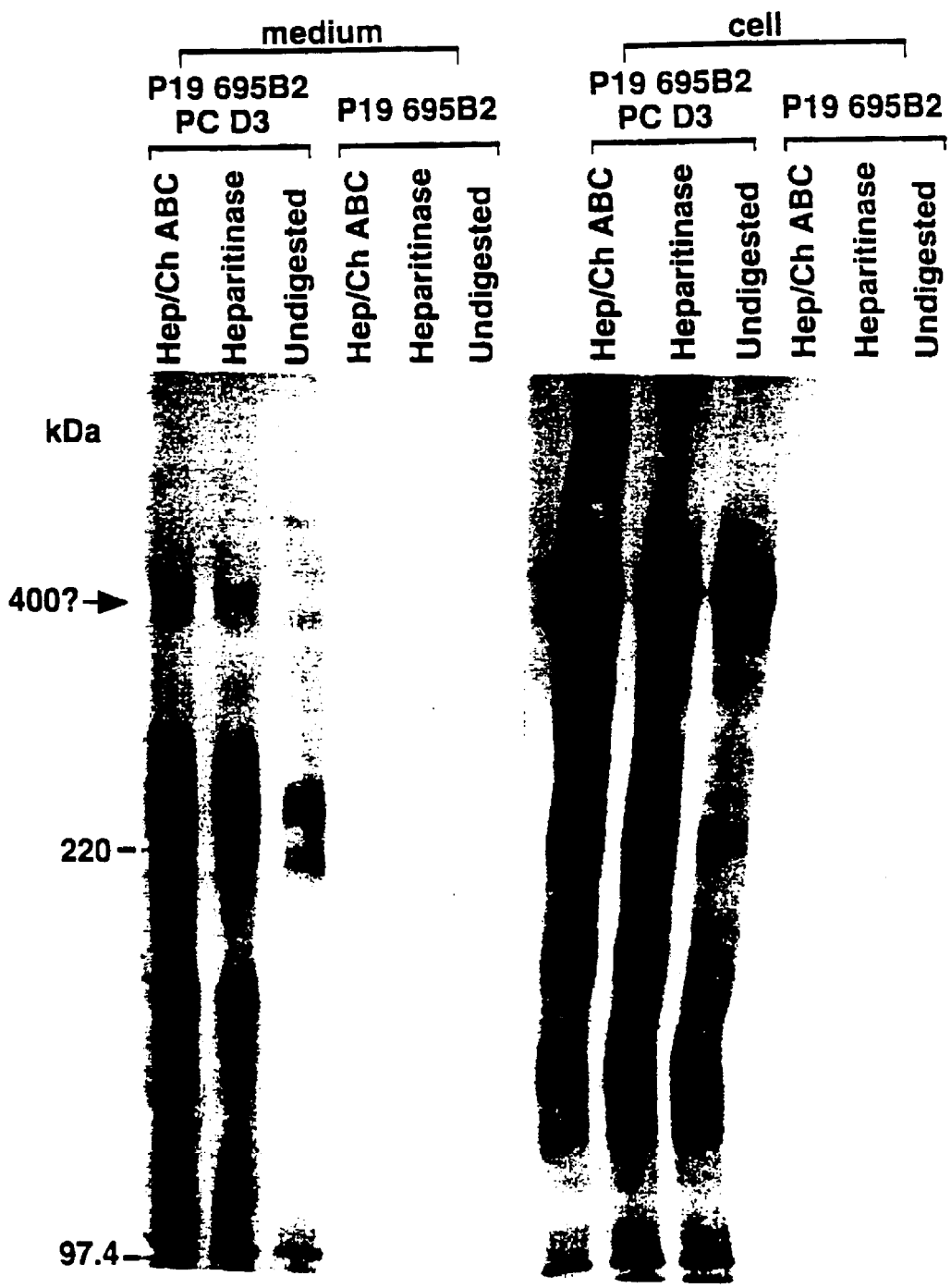
FIG. 6 is a black and white photograph of Western blots from the media and cell lysates of non-transfected versus transfected P19 cells. Overexpression of perlecan in the cell layer and media is demonstrated.

To demonstrate that overexpression of perlecan in P19 695B2 D3 led to increased perlecan protein production, perlecan was isolated and analyzed by Western blotting in the presence or absence of heparitinase and/or chondroitinase ABC pretreatment (to degrade heparan sulfate and/or chondroitin/dermatan sulfate GAGs, respectively) as described in Example 2. As shown in FIG. 6, P19 cells only overexpressing βPP-695 (i.e. P19 695 B2) did not demonstrate detectable perlecan in cell lysates or media. On the other hand, P19 cells overexpressing both perlecan and βPP-695 (i.e. P19 695B2 PC D3) demonstrated a marked increase in perlecan protein in both cell lysates and media as demonstrated by Western blots using a specific perlecan polyclonal antibody (FIG. 6). Cellular perlecan was identified as a ~400 kDa band or smear using the specific perlecan antibody (FIG. 6). Heparitinase digestion (to remove heparan sulfate GAG chains) only slightly increased the immunodetection of cellular perlecan, suggesting that cellular perlecan may be lacking full length heparan sulfate GAG chains. On the other hand, the ~400 kDa band of perlecan isolated from media was visualized only after heparitinase and heparitinase/Chondroitinase ABC treatments (FIG. 6, arrow), indicating that secreted perlecan produced in these cells had heparan sulfate GAG chains. Thus, overexpression of perlecan in P19 cells leads to overproduction of perlecan in media which may be useful for the isolation of perlecan in relatively large quantities.

To determine the potential effects of perlecan overexpression on βPP and Aβ levels in P19 cells, the media and cell layers of P19 cells overexpressing both perlecan and βPP-695 (i.e. P19 695B2 PC B6 and P19 695B2 PC D3) were compared to cells overexpressing βPP-695 only 20 (i.e. P19 695 B2 PC), by immunoprecipitation followed by Western blotting with specific antibodies (6E10 which recognizes human Aβ, and 6561 which recognizes the C-terminus of βPP). All cells (P19 695B2, P19 695B2 PC B6, and P19 695B2 PC D3) were induced to differentiate into neurons by treatment with retinoic acid as previously described (Fukuchi et al., J. Neurochem. 58:1863–1873 (1996)). On the 8th day of differentiation, the media was collected and centrifuged at 12,000×g for 1 hour and the supernatant was made to 10 mM Tris, 1% Nonidet P-40, 0.5% cholic acid, 0.1% sodium dodecyl sulfate (SDS), and 5 mM EDTA, 2 μg/ml leupeptin and 0.1 μg pepstain (pH 8.0). After preabsorption with 50 μl of protein A-agarose (previously coupled to rabbit antibody against mouse IgG), the media was incubated with primary antibodies 6E10 and 40 μl of protein A-agarose (pretreated as described above) for 16 hours. Precipitates were washed three times with TBS containing 1% Nonidet P-40, 5 mM EDTA, 2 μg/ml leupeptin, 2 mM phenylmethyl sulfonylfluoride and was boiled in 20 μl of 2× laemmli buffer for 5 minutes before loading onto 7.5% (to detect higher molecular weight bands) or 16.5% (to detect low molecular weight bands) SDS polyacrylamide gels. The cells were lysed by adding 2× Laemmli buffer (1×=62.5 mM Tris-HCl, pH 6.8, 2% SDS, 10% glycerol, 5% 2-mercaptoethanol, 0.001% bromophenol blue), boiled for 5 minutes, and sheared with a 26-gauge needle. Protein concentrations were determined by Bio-Rad Protein Assay (a product of Bio-Rad laboratories). Aliquots corresponding to 30 μg of protein were applied to 7.5% SDS-polyacrylamide gel electrophoresis (PAGE) and Tris-Tricine 16.5% SDS-PAGE. Following electrophoresis, proteins were electrotransferred to a polyvinylidine difluoride (PVDF) membrane (Immobilon-P, a product of Millipore). The membrane was blocked with phosphate-buffered saline (PBS) containing 5% nonfat dried milk (w/v), 0.02% sodium azide, and 0.02% Tween 20, then incubated at 4° C. for 16 hours with the 6561 antibody (which recognizes amino acids 681–695 of βPP-695) or 6E10 antibody (which recognizes human Aβ) and immunostained with an enhanced chemiluminescence system (a product of Amersham Co.). The relative concentration of the protein was determined by densitometric scanning (Molecular Analyst/PC, a product of Bio-Rad).

Figure 7:
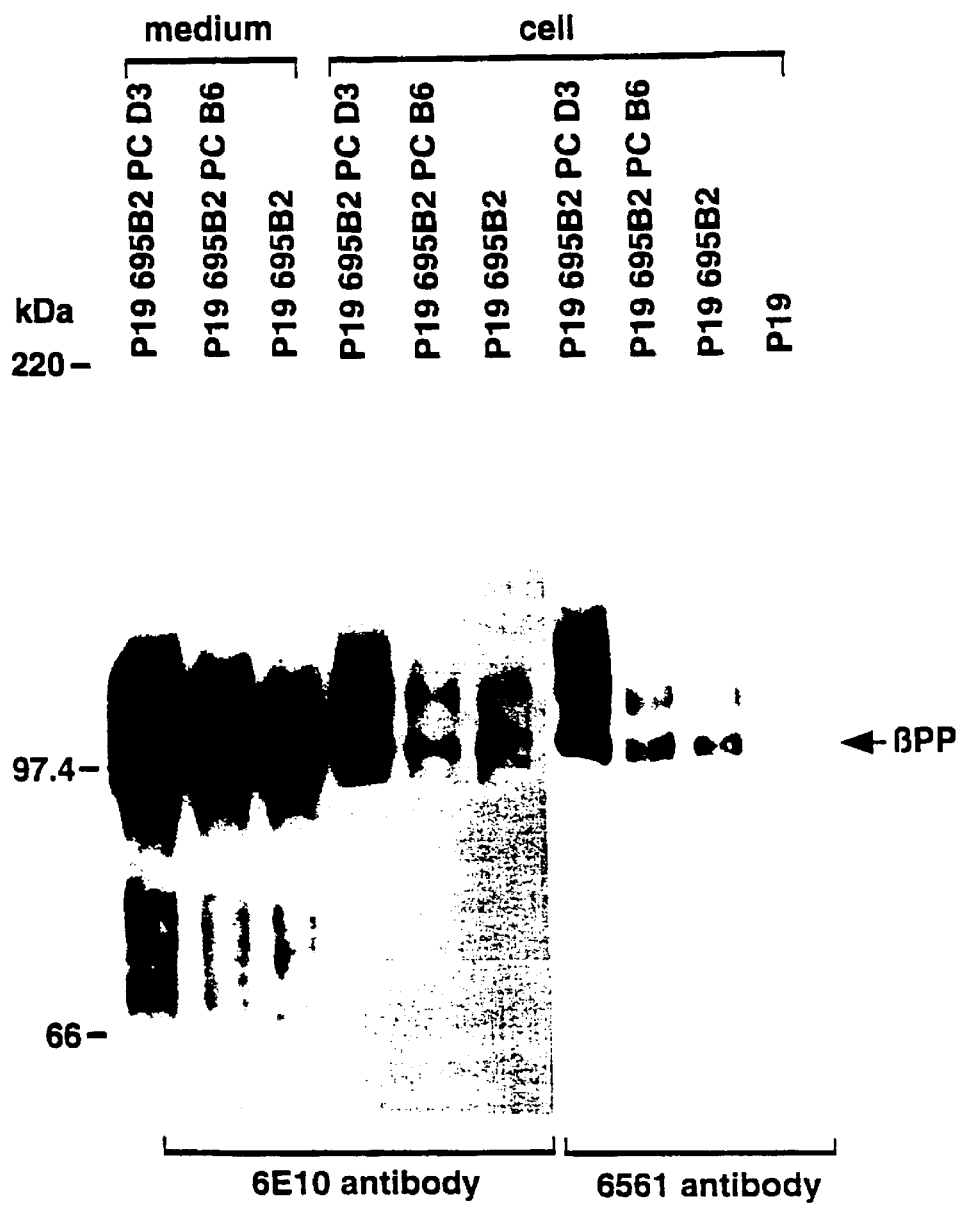
FIG. 7 is a black and white photograph of Western blots detecting βPP from the media and cell lysates of P19 cells overexpressing both perlecan and βPP-695, versus only βPP-695.

As shown in FIG. 7, βPP was evident in both the cell lysates and media of transfected P19 cells overexpressing βPP-695 (i.e. P19 695B2) as discrete or smeared bands at ~100 and 130 kilodaltons (arrow) following Western blots using the 6561 or 6E10 antibodies. On the other hand, a ~4-fold increase in βPP levels in the media was apparent in transfected P19 cells overexpressing both perlecan and βPP-695 (i.e. P19 695B2 PC B6 and P19 695B2 PC D3) (FIG. 7). The P19 695B2 PC D3 cell clone also demonstrated a ~4-fold increase in βPP levels in the cell lysates. These studies indicate that overexpression of both perlecan and βPP-695 leads to a marked increase in βPP levels in the media and cell layer of P19 cells, as compared to P19 cells which overexpress only βPP-695. Overexpression of perlecan may therefore contribute to changes in βPP metabolism and levels.

Figure 8:
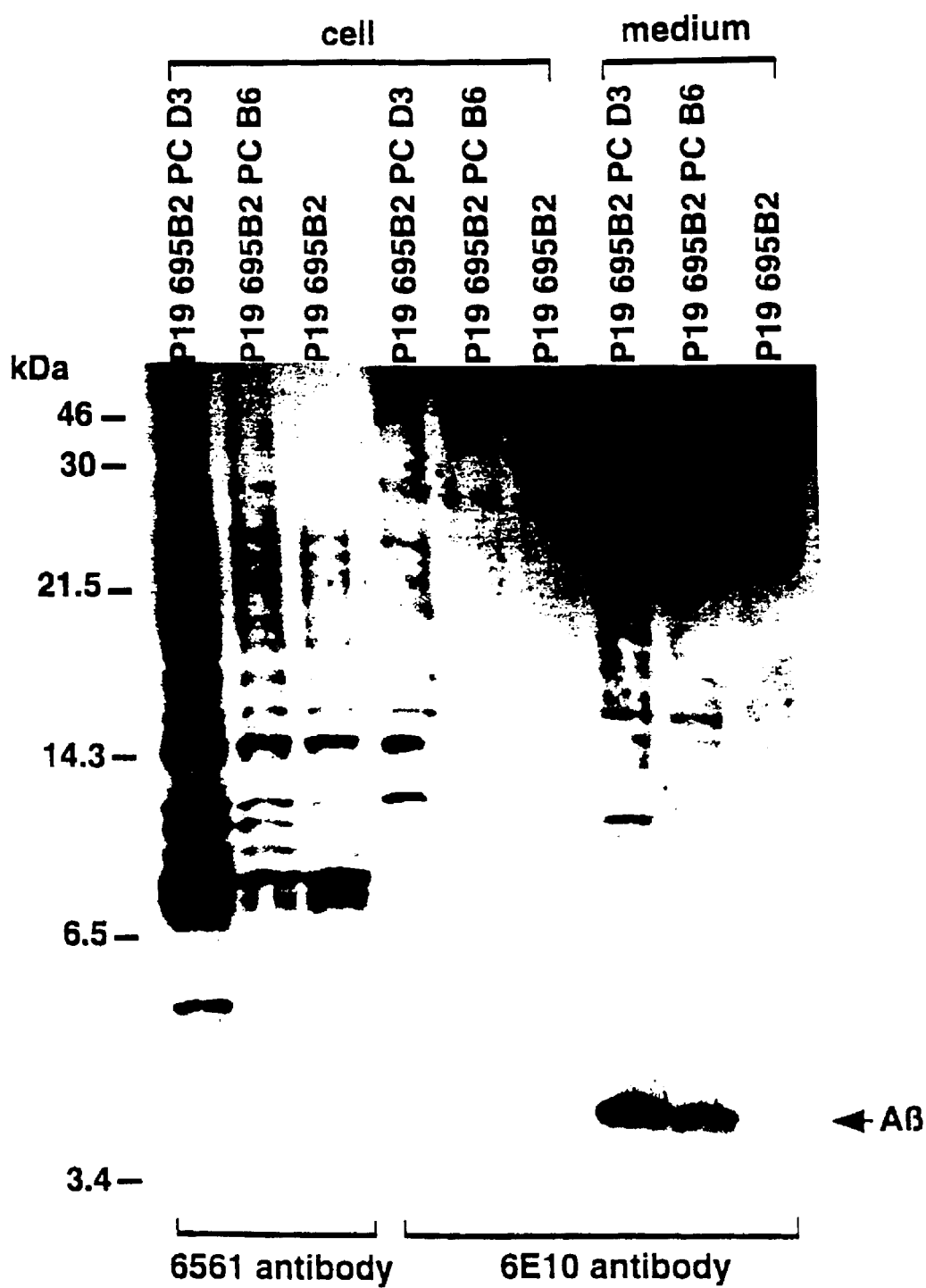
FIG. 8 is a black and white photograph of Western blots detecting secreted Aβ in the media from P19 cells overexpressing both perlecan and βPP-695, versus only βPP-695.
Figure 9:
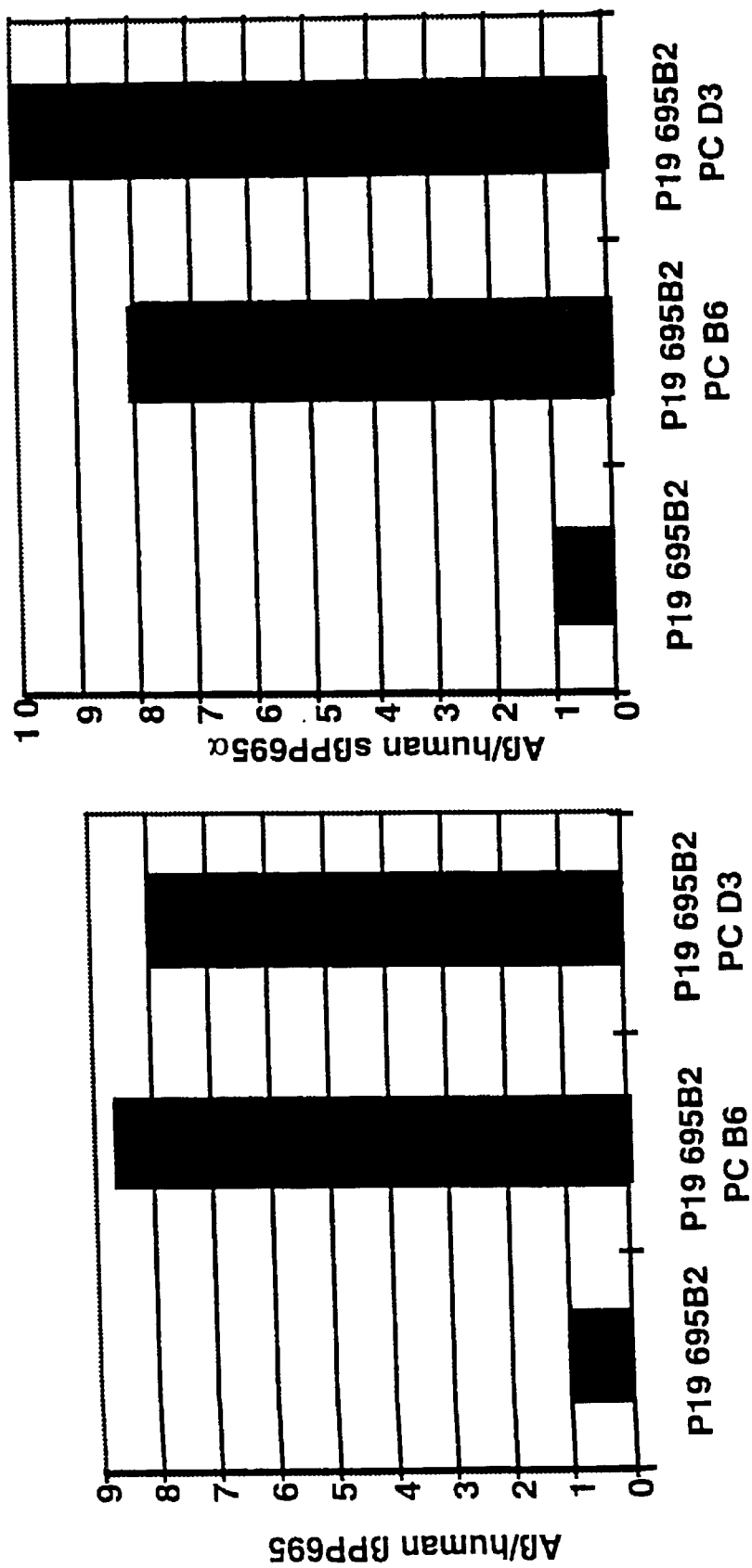
FIG. 9 shows bar graphs indicating normalized levels of secreted Aβ in the media from P19 cells overexpressing both perlecan and βPP-695, versus only βPP-695. A marked 8–10 fold increase in the levels of Aβ in cells overexpressing both perlecan and βPP-695 is demonstrated.

Besides an effect on increasing levels of βPP in both media and cell, perlecan overexpression also led to a marked increase in the secretion of Aβ into the media. As shown in FIG. 8, Western blot analysis utilizing the 6E10 antibody barely detected Aβ (FIG. 8) in media from cells overexpressing βPP-695 only (i.e. P19 695B2). On the other hand, overexpression of both perlecan and βPP-695 (i.e. P19 695B2 PC B6 and P19 695B2 PC D3) led to a marked increase in Aβ levels in the media (FIG. 8, arrow). When secreted Aβ levels were normalized to levels of cellular and secreted βPP, an 8–10-fold increase was demonstrated in P19 cells which overexpress both perlecan and βPP-695 (FIG. 9). These results indicate that overexpression of perlecan leads to an increase in secreted Aβ levels.

EXAMPLE 4

Overexpression of Perlecan Leads to Degeneration of P19-Derived Neurons

Figure 10:
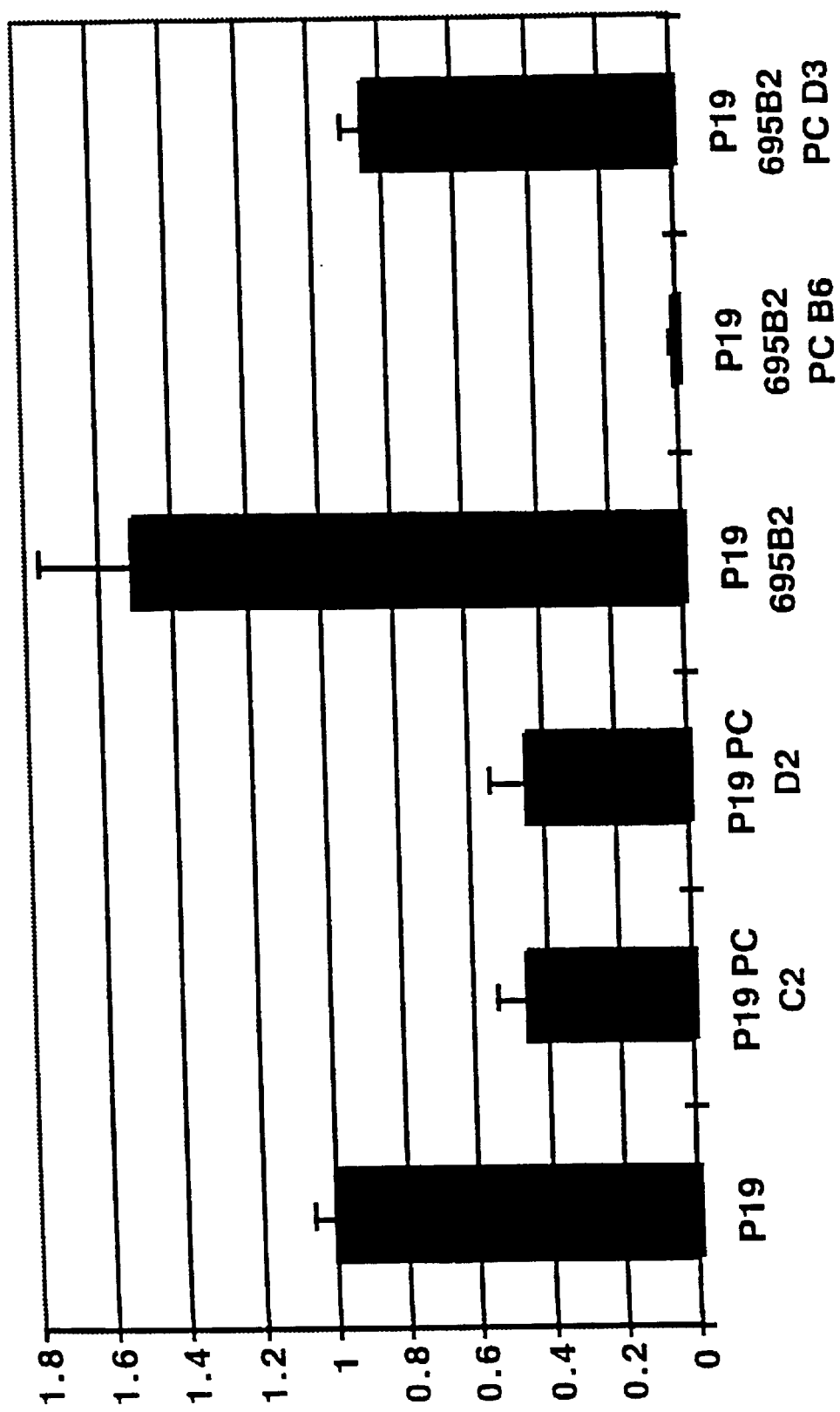
FIG. 10 shows bar graphs comparing the number of surviving neurons in P19 cells overexpressing perlecan only, βPP-695 plus perlecan, βPP-695 only, and control parental cells (P19 only). Overexpression of perlecan only or perlecan plus βPP-695 leads to decreased neuronal survival.

To study the effects of perlecan overexpression on neuronal survival, P19 cells overexpressing perlecan only (designated P19 PC C2 and P19 PC D2) were also induced to differentiate into neurons. These additional P19 cell lines were isolated by stable transfection of pCA-DI-V and perlecan overexpression in these two clones was confirmed by Western blot analysis as described in Example 1 and Example 2. Transformed cell clones overexpressing perlecan only (P19 PC C2, P19 PC D2), perlecan and βPP-695 (P19 695B2 PC B6 and P19 695B2 PC D3), βPP-695 only (P19 695B2) and their parental cells (P19) were induced to differentiate into neuronal cells by treatment with retinoic acid. Proliferating non-neuronal cells were eliminated from the cultures by treatment with 10 μM of cytosine β-D-arabinofuranoside (Ara C). Eight days following initial treatment with retinoic acid, surviving neurons were quantified by measuring produced formazan from MTS according to the manufacturer's protocol (Cell Titer 96 Aqueous Assay, a product of Promega). For each cell clone 5 independent cultures were prepared and subjected to statistical analysis. The results are shown in FIG. 10. Cell survival of the clones overexpressing perlecan only (i.e. P19 PC C2, P19 PC D2) were significantly lower than control P19 cells (i.e. P19), and in comparison to cells overexpressing βPP-695 only (i.e. P19 695B2). The P19 695B2 PC D3 line which overexpresses both perlecan and βPP-695 also showed a decrease in neuronal survival, especially when compared to cells which only overexpress βPP-695 (i.e. P19 695B2). All of the cells of the P19 695B2 PCB6, which overexpress both perlecan and βPP-695 died out. These studies therefore demonstrated that overexpression of perlecan also has an effect on neuronal cell survival. Therefore, cells which overexpress perlecan only, and perlecan and βPP may be utilized a screening tools for the development of new therapeutic and preventive agents for Alzheimer's disease. In a preferred embodiment, anti-Alzheimer's compounds can be tested and will be deemed effective if they cause a lowering of secreted Aβ levels in the media, and/or increase neuronal survival.

EXAMPLE 5

Construction of Perlecan Transgenic Expression Plasmids

The expression vector, pCA-DI-V (FIG. 3C), was used to prepare DNA for microinjection into mouse fertilized eggs. pCA-DI-V was digested with Hind III enzyme and electrophoresed on agarose to separate the bacterial DNA sequences from the DNA construct to be used for microinjection. The DNA construct that contained the cytomegalovirus enhancer/beta-actin promoter, cDNA for the entire perlecan core protein, and a polyadenylation signal were electrophoresed onto a DEAE-cellulose membrane. The DNA on the membrane was eluted by a high-salt buffer (50 mM Tris-HCl, pH 8.0, 1M NaCl, and 10 mM EDTA, pH 8.0) and extracted with phenol and chloroform. After precipitating the DNA by ethanol, the DNA was resuspended in Tris-EDTA (10 mM Tris-HCl, pH 7.5, 0.25 mM EDTA) and used for microinjection into fertilized eggs.

EXAMPLE 6

Collection and Injecting the Eggs with the DNA Construct

The transgenic organisms of the invention all include within a plurality of their cells a cloned recombinant or synthetic DNA sequence which is believed to relate to the pathogenesis of the amyloid diseases. More specifically, the transgenic organisms contain specific sequences of exogenous genetic material which are comprised of a specific promoter sequence which allows for production of perlecan core protein. Since it is possible to produce transgenic organisms of the invention, a general description will be given of the production of transgenic organisms by referring generally to exogenous genetic material. This general description can be adapted by those skilled in the art in order to incorporate the above-described specific DNA sequences into organisms and obtain expression of those sequences utilizing the materials and methods described below. For more information regarding the production of transgenic mice refer to U.S. Pat. No. 4,873,191 issued Oct. 10, 1989 (incorporated herein by reference to disclose methods producing transgenic mice), and to the scientific publications referred to and cited therein.

One-cell stage embryos (F2 of C57BL/6J X SJL) were collected from the oviducts of F1 female mice of C57BL/6J X SJL/J that had been already mated with F1 male mice of C57BL/6J X SJL/J. These embryos should be early enough to distinguish male pronuclei from female pronuclei. Cumulus cells surrounding oocytes were removed by hyaluronidase treatment, washed properly and incubated at 37° C. in an atmosphere of 5% $CO_2$ for a certain time prior to DNA injection. Any method which allows for the addition of the exogenous genetic material can be utilized as long as it is not destructive to the cell, nuclear membrane or other existing cellular or genetic structures. The exogenous genetic material is preferably inserted into the nucleic genetic material by microinjection. Microinjection of cells and cellular structures is known and is used in the art. About 1–2 picoliters (pl) of the DNA construct prepared in Example 5 (about 100–200 copies of the transgene per pl) was microinjected into a male pronucleus. Approximately 100 embryos were injected with the DNA construct described in Example 5. The injected embryos were incubated from several hours to one day and then transplanted to the oviducts of pseudopregnant ICR foster mothers of Day 1 of pregnancy. The day when a vaginal plug was recognized was recorded as Day 1. The transplanted foster mothers were fed until a delivery of the fetus. After delivery, neonates (25 pups) were nursed by the foster mothers for 4 weeks until weaning. At the time of weaning, the tails of the neonates were cut for Southern blot analysis to determine the integration of transgenes into mouse chromosomes. The founder mice, judged as transgenic by Southern blot analysis, were back-crossed with C57BL/6J mice to establish lines of transgenic mice with C57BL/6J genetic background.

EXAMPLE 7

Determination of Transgene Copy Numbers

Figure 11:
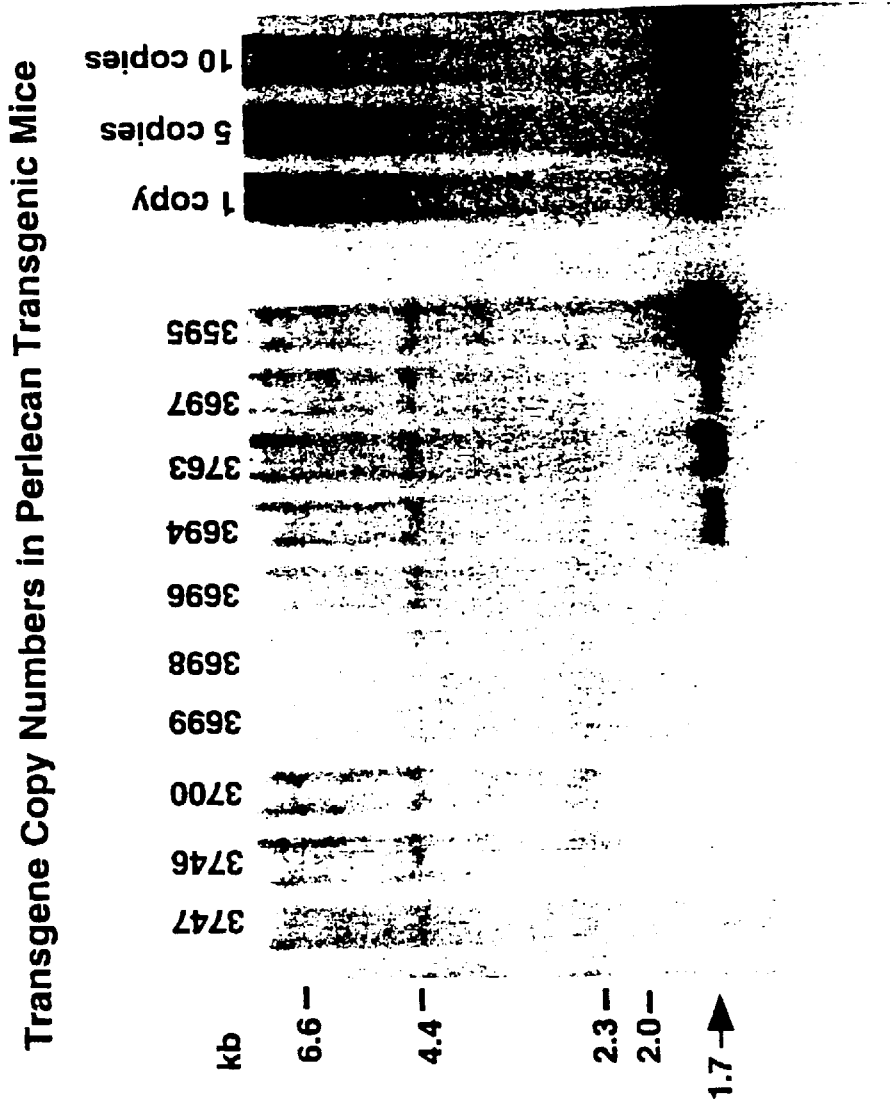
FIG. 11 is a black and white photograph of Southern blots of DNA taken from transgenic mice overexpressing mouse perlecan (domains I–V). Chromosomal integration of the perlecan transgene is demonstrated in Southern blots of DNA taken from transgenic mice, and four perlecan transgenic founder mice are shown.

Pups produced from microinjection of the DNA construct (pCA-DI-V) were grown to 4 to 6 weeks old and then the tails of the pups were cut. The DNA was isolated from the tails using QIAamp tissue kit (a product of Qiagen Inc.). 10 μg of DNA isolated from mouse tails were digested with Sca I restriction enzyme and separated by electrophoresis on a 0.9% agarose gel. Additionally, PCA-DI-V was digested with Sca I restriction enzyme and 0.045 ng (1 copy), 0.225 ng (5 copies) and 0.45 ng (10 copies) of the digested pCA-DI-V were also separated on the same agarose gel as a reference positive control. The separated DNA was then blotted onto a nylon membrane. The membrane was prehybridized for 6 hours at 42° C. in 50% formamide, 5× saline sodium citrate (SSC; 1×SSC=0.15M NaCl and 0.015 M sodium citrate, pH 7.0), 5× Denhardt's solution (1× Denhardt's solution=0.02% each of Ficoll, polyvinylpyrrolidone, and bovine serum albumin), 0.1% sodium dodecyl sulfate (SDS), and 100 mg/ml of denatured herring sperm DNA and then hybridized in the above solution containing 10% dextran sulfate and ~$10^7$ cpm of a radiolabeled probe at 42° C. for 18 hours. The radiolabeled probe was the 1.7-kb Sca I fragment of mouse perlecan cDNA (bp 5523–7215 of perlecan cDNA)(Noonan et al., *J. Biol. Chem.* 266:22939–22947 (1991)). The membrane was then washed at 65° C. in 0.2×SSC and 0.5% SDS. The membrane was exposed to Kodak XAR film with an enhancer screen, at ~−80° C. for 4 days. As shown in FIG. 11, out of approximately 25 pups, the integrated transgene in the mouse genome was identified as a 1.7-kb fragment on Southern blot in four founder mice (designated #3595, 3697, 3763 and 3694 in FIG. 11). Founder mouse #3595 was found to have 5–10 copies of pCA-DI-V whereas founder mouse #3697, 3763 and 3694 had approximately one copy of pCA-DI-V.

EXAMPLE 8

Confirmation of Perlecan Overexpression in Perlecan Transgenic Mice

The founder mice (#3595, 3697, 3763 and 3694) were mated with C57BL/6J mice. Each of the male founders (#3694 and 3595) were housed in one cage together with two C57BL/6J female mice, and each of the female founders (# 3697 and 3763) were housed in one cage together with one C57BL/6J male mouse. Every female mated gave birth to 8–12 mice indicating that the founders were fertile. The mouse tails from the progeny are cut to perform Southern blot analysis as described above to demonstrate the transgene segregation. Mice determined as transgenic by Southern blot analysis are mated with C57BL/6J mice for propagation.

Levels of transgene expression in the transgenic mice were determined by Northern blotting for MRNA, Western blotting and immunostaining for protein. Most of the techniques which are used to perform Northern and Western blot analysis are widely practiced in the art and most practitioners are familiar with the standard resource materials as well as specific conditions used in the procedures.

Figure 12:
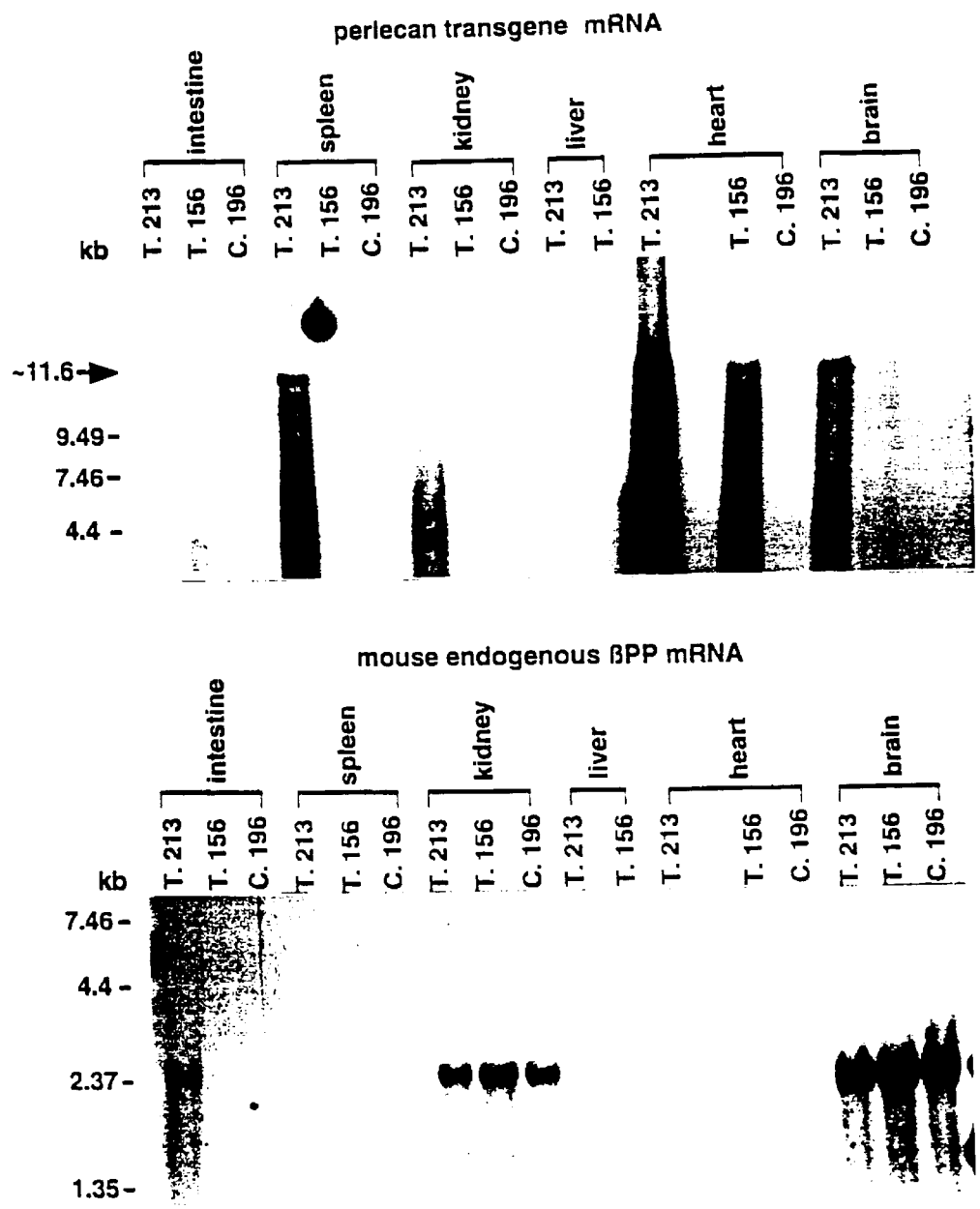
FIG. 12 is a black and white photograph of Northern blots of RNA isolated from tissues of perlecan transgenic mice versus control litter-mates. Overexpression of perlecan MRNA in several tissues is demonstrated.

Northern Blotting: Three mice were sacrificed by cervical dislocation under anesthesia; T 213, a 3-month old progeny from perlecan transgenic founder 3595 (5 copy founder); T 156, a 3-month old progeny from perlecan transgenic founder 3694 (1 copy founder), and c 196, a 3-month non-transgenic control litter-mate of T 213. Tissues including brain, heart, liver, kidney, spleen and intestine were quickly removed and homogenized in a denaturing solution consisting of 4M guanidinium thiocyanate, 25mM sodium citrate, pH 7.0; 0.5% sarcosyl, 0.1M 2-mercaptoethanol) and passed through a syringe fitted with a 27 gauge needle. After adding sodium acetate, the RNA was extracted with phenol/chloroform and precipitated with isopropanol. The precipitated RNA was resuspended again with the above denaturing-solution and precipitated with isopropanol. After rinsing the RNA with 75% ethanol, the RNA was resuspended with sterile double distilled water. 20 µg of total RNA from each tissue was electrophoresed through a 1% agarose-formaldehyde gel, followed by capillary transfer to a nylon membrane. A perlecan probe (mouse perlecan cDNA, bp 5523–7215 of perlecan cDNA as described in Noonan et al., *J. Biol. Chem.* 266:22939–22947 (1991)) was radiolabeled with $^{32}$p dCTP to a specific activity of $4\times10^8$ cpm/µg using a random primed labeling kit (a product of Boehringer Mannheim). The membrane was hybridized for 20 hours at 42° C. in 50% formamide 5xSSC (1xSSC= 0.15M NaCl, 0.015M sodium citrate, pH 7.0), 0.1% SDS and 100 µg/ml of denatured herring sperm DNA. Following hybridization, the membrane was washed twice at 65° C. in 0.2xSSC and 0.2% SDS for 30 minutes each. The membrane was then exposed to Kodak XAR film with enhancer screens at ~70° C. for 6 hours. The results are shown in FIG. 12. High levels of expression of the transgene mRNA with the expected 11.6 kb size, were observed in brain, heart, kidney, spleen and intestine of T 213 (progeny of founder with 5 copies of transgene). Levels of perlecan mRNA in T 156 (progeny of founder with 1 copy of transgene) were much lower than those in T 213 (FIG. 12). No endogenous mRNA for perlecan was detected in any of the C 196 tissues. This study demonstrated that perlecan overexpression was particularly evident in brain and in other tissues of transgenic mice carrying ~5 copies of the transgene.

Figure 13:
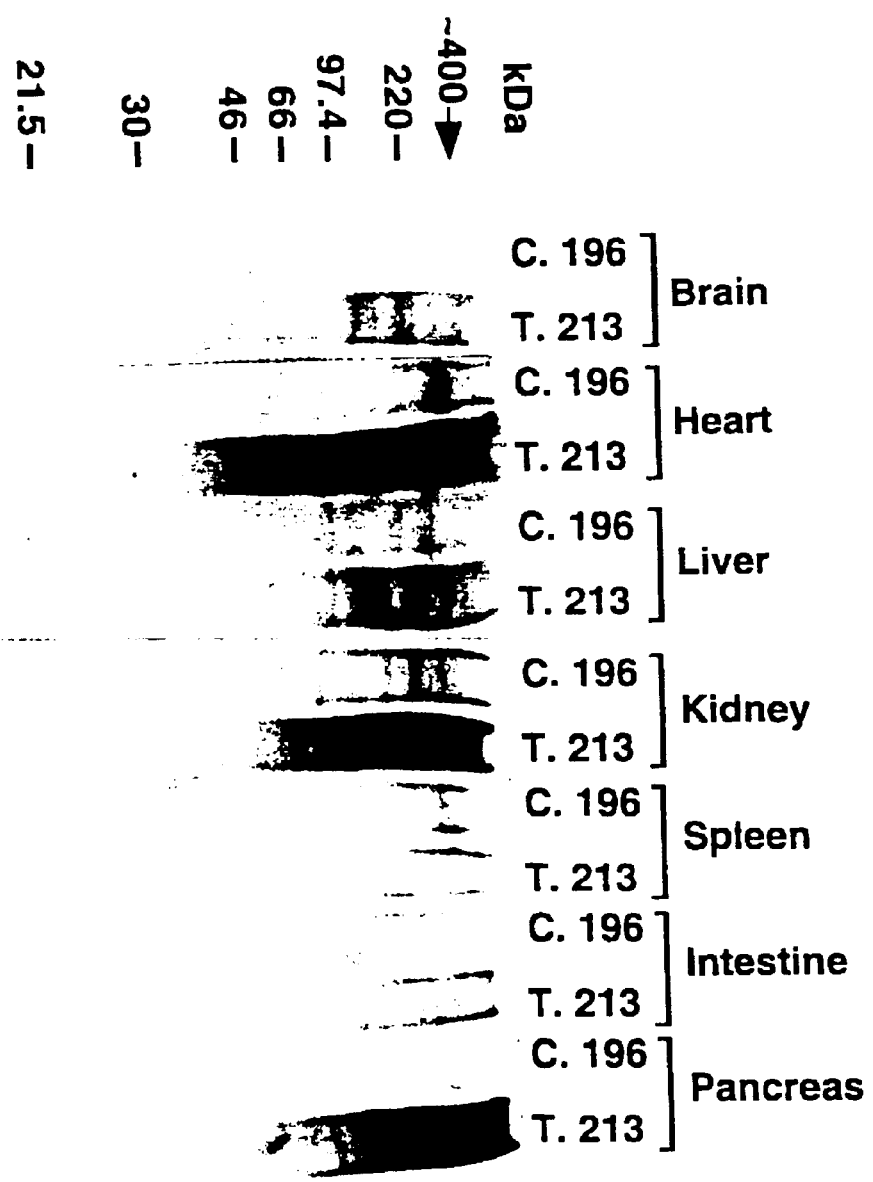
FIG. 13 is a black and white photograph of Western blots of protein isolated from tissues of perlecan transgenic mice versus control litter-mates. Overproduction of perlecan proteoglycan in various organs of transgenic mice is demonstrated.

Western Blotting: Levels of the protein products from the transgene in the transgenic mice were determined by Western blot analysis. The tissues (i.e. brain, heart, liver, kidney, spleen, intestine and pancreas) isolated from transgenic T 213 and control C 196 were homogenized in 2x Laemmli buffer (1x=62.5 mM Tris-HCl, pH 6.8, 2% SDS, 10% glycerol, 5% 2-mercaptoethanol, 0.001% bromophenol blue), boiled for 5 min, and sheared with a 26-gauge needle. Protein concentration was determined by Bio-Rad Protein Assay (a product of Bio-Rad). AliquQts corresponding to 30 µg of protein were applied to 4–20% gradient gels for SDS-PAGE. Following electrophoresis, proteins were electrotransfered to a polyvinylidine difluoride (PVDF) membrane (Immobilon-P, Millipore). The membrane was blocked with phosphate-buffered saline containing 5% nonfat dried milk (w/v), 0.02% sodium azide, and 0.02% Tween 20, then incubated at 4° C. for 16 hours with perlecan monoclonal or polyclonal antibodies which recognize perlecan core protein, and immunostained with an enhanced chemiluminescence system (a product of Amersham). The results are shown in FIG. 13. Substantial increased amounts of transgene protein product (i.e. perlecan detected as a ~400 kDa band or smear) were observed in brain, heart, liver, kidney, and pancreas of T 213 in comparison to control (i.e. C196). This study demonstrated that perlecan overproduction successfully occurred in brain and in other tissues, and was apparent in a 3-month old perlecan transgenic mouse.

Figure 14:
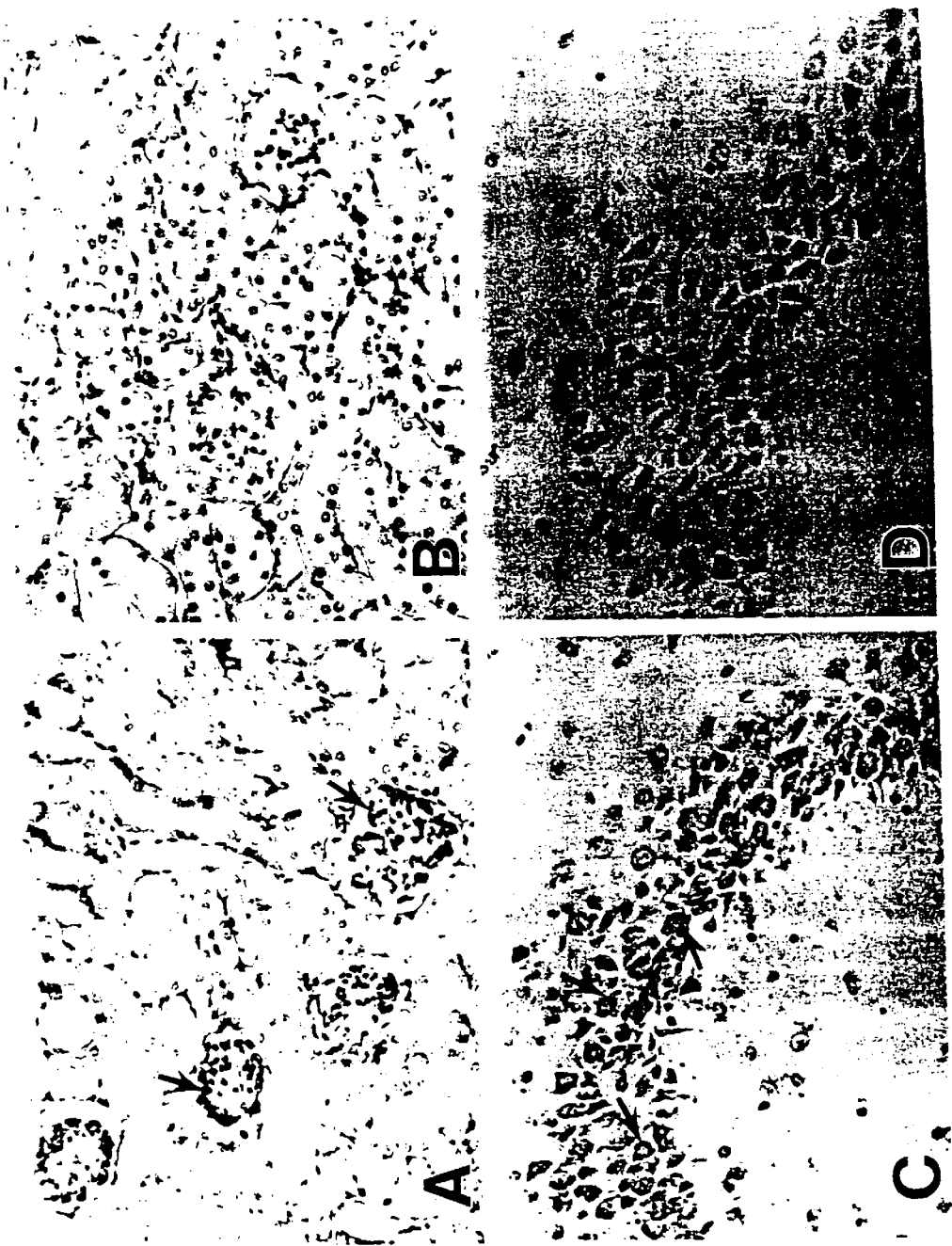
FIG. 14 are black and white microphotographs from brain and kidney tissues of 5-month old perlecan transgenic mice versus control litter-mates. The tissues were immunostained with an antibody specific to perlecan, followed by counterstaining with hematoxylin. Accumulation of overproduced perlecan in tissues of transgenic mice is demonstrated.

Immunostaining: For immunostaining studies, animals were first sacrificed by deep anesthesia. The tissues of two 5-month old transgenic progenies from the 3595 (5 copy founder) and two 5-month old non-transgenic litter-mates were subjected to immunostaining. The tissues including brain, heart, intestine, kidney and pancreas were removed, fixed by 10% formalin and embedded in paraffin by procedures known to those skilled in the art. 10 µm sections were then cut and subjected to the avidin-biotin immunoperoxidase method to detect perlecan using perlecan specific antibodies and the Vectastain ABC kit (a product of Vector Laboratories) as described below. Endogenous peroxidase was eliminated by treatment with 3% hydrogen peroxide for 30 minutes after deparaffinization of the sections. After rinsing with distilled water, the sections were blocked with 15% goat serum in Tris-buffered saline (TBS) for 60 minutes at room temperature and incubated with a perlecan primary polyclonal antibody (which specifically recognizes the core protein of perlecan; antibody of Dr. J. Hassell) in 0.1M TBS containing 15% goat serum for 16 hours at 4° C. The sections were then rinsed in 0.1 M TBS containing 1% goat serum and incubated with biotinylated goat anti-rabbit IgG secondary antibody for 1 hour at room temperature. After washing, the sections were incubated with Vectastain reagent for 60 minutes at room temperature. Peroxidase activity was then detected by treatment with 3,3'-diaminobenzidine. Strong immunoreactivity for perlecan was evident in transgenic mice but not in control liter-mates, especially in the epithelium of the choroid plexus, the myofibrils of the heart, the acidophil cells of the gastric gland, the glomeruli of the kidney, and the cells in the islets of Langerhans in pancreas. In addition, transgenic mice, but not control litter-mates demonstrated moderate perlecan immunostaining in the C3A neuronal layer of the hippocampus, the Purkinje cell layer of the cerebellum and the large neurons of the brain stem. FIG. 14 demonstrates strong perlecan immunostaining in kidney glomeruli (FIG. 14A, arrows), and in the C3A neuronal layer of the hippocampus (FIG. 14C, arrows) of a 5-month old perlecan transgenic mouse. In comparison, control litter-mates demonstrate weak to no staining for perlecan in kidney glomeruli (FIG. 14B) and hippocampal neurons (FIG. 14D). These results confirm that perlecan overexpression leads to perlecan protein accumulation in specific sites in brain and in systemic organs.

EXAMPLE 9

Figure 15A:
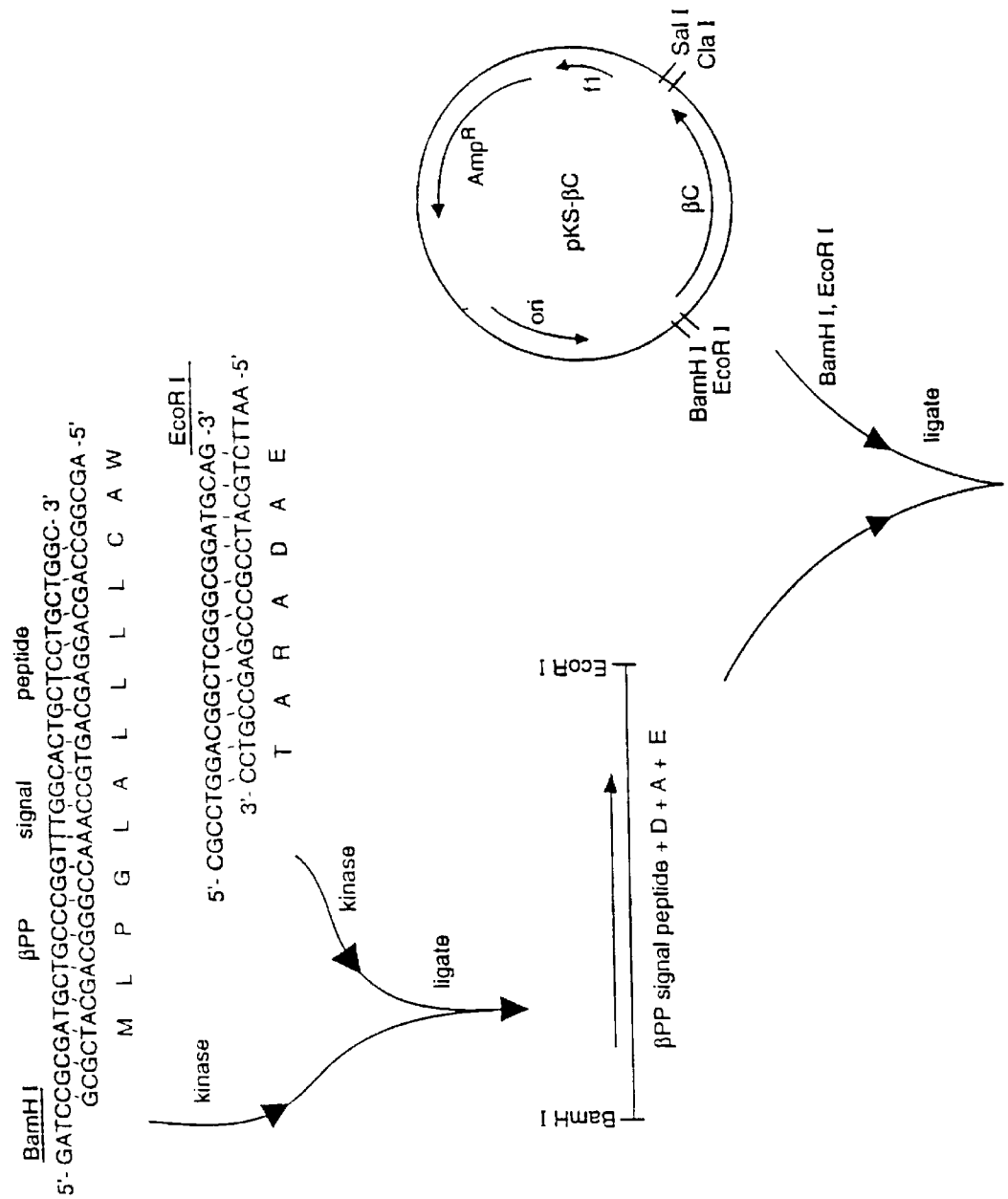
FIGS. 15A and 15B demonstrate the construction strategy for the cytomegalovirus enhancer/chick β-actin promoter linked to the signal peptide and to the C-terminal 99 amino acids of the beta-amyloid precursor protein as an example to produce beta-amyloid precursor protein transgenic mice (CA-SβC) (SEQ ID NO: 5, SEQ ID NO: 6, SEQ ID NO: 7, SEQ ID NO: 8, SEQ ID NO: 9 and SEQ ID NO: 10).
Figure 15B:
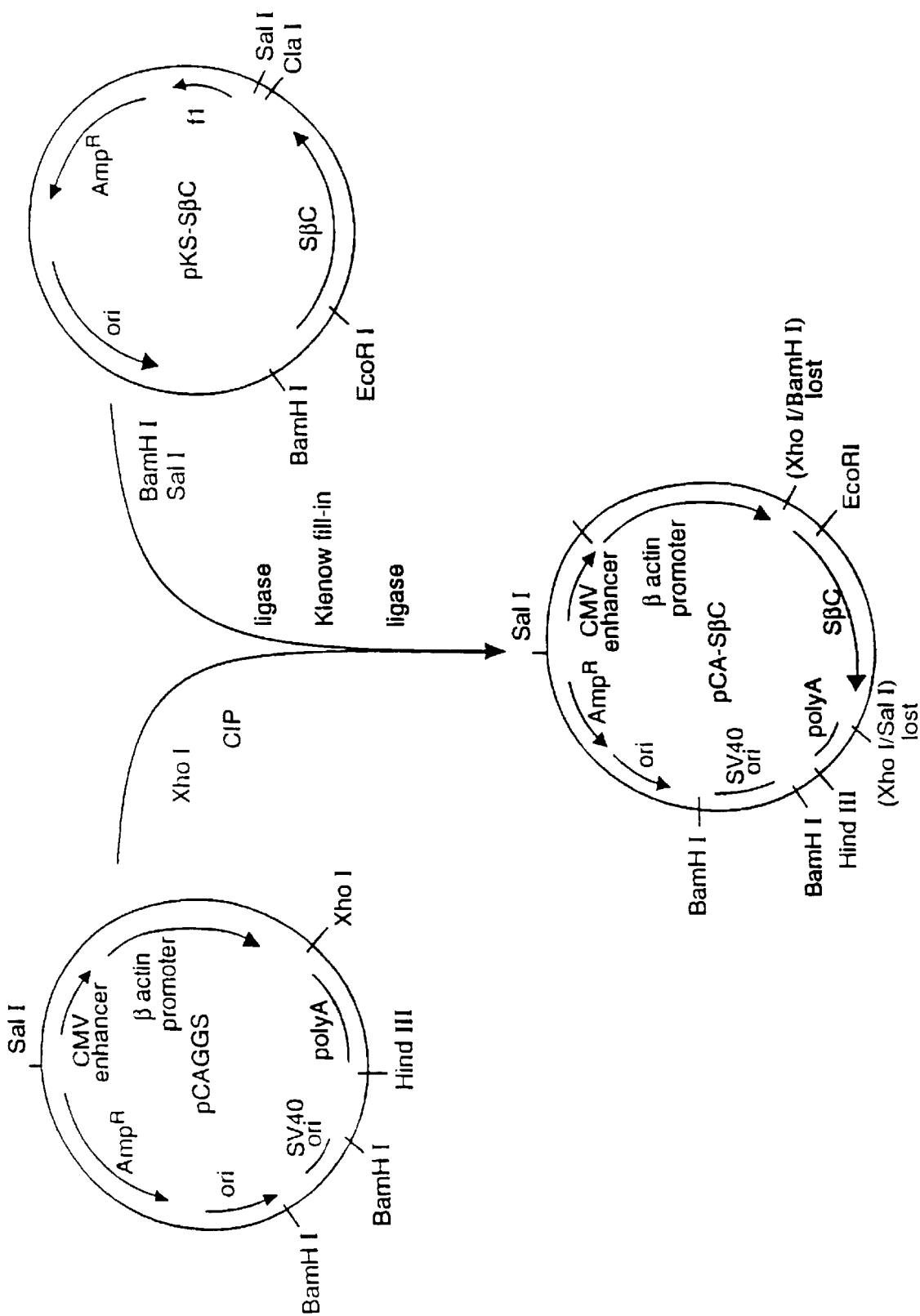

Production of Beta-Amyloid Precursor Protein Mice as a First Step in Producing a New Animal Model of Alzheimer's Disease Amyloidosis Four founder lines of transgenic mice that constitutively overproduce the signal sequence and the 99 amino acid C-terminal region of the human beta-amyloid precursor protein were established. The cDNA for the signal sequence and the 99 amino acid C-terminal region (the construct referred to as SβC) of the human beta-amyloid precursor protein (hereinafter called βPP) was placed under the control of a cytomegalovirus enhancer and a chick beta-actin promoter in pCAGGS (FIG. 15A)(Niwa et al., *Gene* 108:193–200 (1991)). To overexpress SβC under control of a cytomegalovirus enhancer and a chick β actin promoter, an expression vector, pCA-SβC was constructed. Using the LMG2 human brain stem lambda gt11 cDNA library (a product of ATCC, catalog #ATCC37432), a partial cDNA of the human βPP, extending from base pairs 901–2851 (Kang et al., *Nature* 325:733–736 (1987)) was isolated. The EcoRI/ClaI fragment (bp 1796–2473; Kang et al., *Nature* 325:733–736 (1987)) of the cDNA was subcloned into pBluescript KS (a product of Stratagene) at the same restriction enzyme sites to create pKS-βC (FIG. 15A). In a separate reaction the signal peptide coding sequence for βPP and the sequence for the first 3 amino acids of the beta-amyloid protein (BamHI site+bp-4-51+bp 1789–1795+EcoRI site; bps are in Kang et al., *Nature* 325:733–736 (1987)) was chemically synthesized (FIG. 15A). This synthetic fragment was also ligated to the EcoRI/ClaI fragment (bp 1796–2473) of βPP in pKS-βC using BamHI and EcoRI sites to create the pKS-SβC plasmid. This plasmid was digested with BamHI and SalI and the 0.8-kb fragment coding for SβC of βPP was isolated. The SalI site of the 0.8-kb fragment was ligated onto one of the XhoI sites of the expression vector, pCAGGS (Niwa et al., *Gene* 108:193–200 (1991)), which was previously digested with XhoI (FIG. 15B). The other ends were ligated after blunt end formation with the Klenow fill-in reaction to create pCA-SβC (FIG. 15B). Fertilized eggs were injected into pCA-SβC after removing bacterial sequence from pCA-SβC. Four independent lines of transgenic mice were established. To determine the levels of mRNA expression from the transgene, the total RNA from transgenic mice was isolated and analyzed by Northern blot using a radiolabeled human cDNA probe (bp 1795–2851; Kang et al., *Nature* 325:733–736 (1987)). The high levels of expression of MRNA with the expected size, 1.06-kb from the transgene were observed in virtually all tissues examined including the brain (Fukuchi et al., *Am J Path* 149:219–227 (1996)). Native mRNA with a size of 3.2 kb was also observed in the brain and kidney. On Western blots, ~11–17 kDa protein products from the transgene were observed in lung, muscle, intestine, liver and kidney in transgenic mice, whereas no corresponding fragments were observed in Western blots from the same tissues of non-transgenic mice. A 3–5 fold increase in the C-terminal fragments of βPP was found in the brains of transgenic mice compared to controls. The amount of the C-terminal fragments in the intestine was at least 50 times greater than that observed in the brain of transgenic mice, and at least 3 times greater than that observed in the heart of transgenic animals (Fukuchi et al., *Am. J. Path*. 149:219–227 (1996)).

Six-month, 9-month, 12-month, 14-month and 16-month-old transgenic mice bearing CA-SβC were sacrificed for immunohistochemical and histopathological analysis. Non-transgenic siblings, ranging from 12–16 months were used as controls. By immunohistochemical analysis, using antibodies 1282 (a rabbit polyclonal antiserum raised against beta-amyloid protein; Tamaoka et al., *Proc. Natl. Acad. Sci. USA* 89:1345–1349 (1992)) and 10D5 (directed against amino acids 1–16 of beta-amyloid protein; Hyman et al., *J. Neuropath. Exp. Neurol*. 51:76–83 (1992)), large immunoreactive deposits were found in the lamina propria of the mucosa of the small intestine from transgenic mice >12 months of age, but not in younger mice. These deposits were positive for Congo red (indicative of amyloid) demonstrating a red/green birefringence as viewed under polarized light and consisted of fibrils 7–10 nm in diameter as observed by electron microscopy. Surprisingly, these beta-amyloid eposits were also found to be positive for perlecan sing perlecan specific core protein antibodies. The accumulation of both beta-amyloid and perlecan in these deposits suggests that both components are necessary for amyloid deposition and serves as further evidence for the basis of the present invention. Although fibrillar beta-amyloid deposits were observed in the small intestine in these transgenic mice, no pathological changes were observed in the brains of transgenic mice indicating that other co-factors, such as perlecan, are probably necessary for the ultimate formation, deposition and persistence of fibrillar beta-amyloid protein in brain.

EXAMPLE 10

Production of Perlecan-Amyloid Protein Double Transgenic Animals

Figure 16:
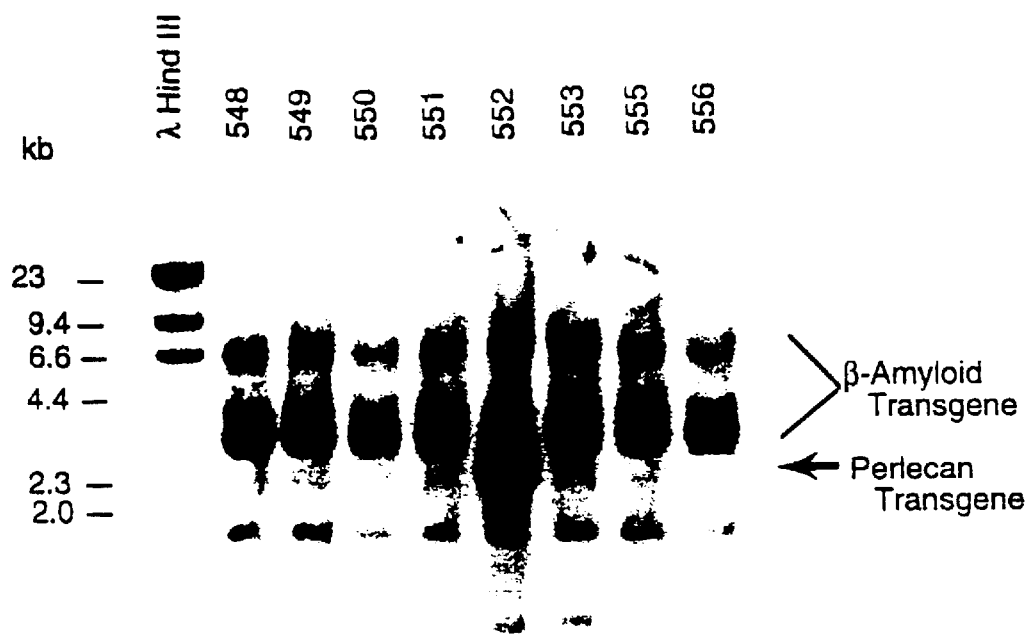
FIG. 16 is a black and white photograph of Southern blots taken from mouse tail DNA of double transgenic mice produced by mating perlecan transgenic mice with transgenic mice that overproduce the C-terminal 99 amino acids of the beta-amyloid precursor protein. Pup #552 was found to incorporate the genes for both perlecan and the C-terminal 99 amino acids of the beta-amyloid precursor protein.

Perlecan-amyloid protein transgenic animals are produced by the mating of perlecan transgenic mice with, for example, beta-amyloid precursor protein transgenic animals. Double transgenic mice carrying both transgenes (CA-SβC and perlecan) were created by mating the two lines of transgenic mice. Generally, 25% of emerging pups from mating heterozygous parents for each transgene should carry both transgenes, and 50% of emerging pups from mating heterozygous mice for one transgene with homozygous mice for the other transgene should carry both transgenes. Homozygous mice for CA-SβC transgenes were established by mating heterozygous mice for CA-SβC. The homozygotes for CA-SβC was confirmed by crossing the homozygous mice for CA-SβC to C57BL/6J non-transgenic mice. A homozygous male for CA-SβC was crossed to a heterozygous female (a progeny from founder 3595) for the perlecan transgene. Eight pups were produced by the mating and the tails from the pups were cut to extract the DNA for Southern blot analysis. The DNA was hybridized with radiolabeled perlecan (bp 5523–7215 of perlecan cDNA in Noonan et al., *J. Biol. Chem*. 266:22939–22947 (1991)) and beta-amyloid (bp 1796–2473 in Kang et al., *Nature* 325:733–736 (1987)) probes. The results are shown in FIG. 16. Pup #552 was found to positive for both perlecan and beta-amyloid precursor protein (C-terminal portion which contains the Aβ region)(shown in FIG. 16) and verified the successful production of a double transgenic mouse which carried transgenes for both perlecan and beta-amyloid.

EXAMPLE 11

Screening of Compounds for Treatment of Alzheimer's and Other Amyloid Diseases

The transgenic animals, transfected cells, or animal cells derived from transgenic animals, can be used to screen compounds for a potential effect in the treatment of Alzheimer's disease and other amyloidoses using standard methodology. In such screening assays, the compound is administered to the animals, or introduced into the culture media of transfected cells, or cells derived from these animals, over a period of time and in various dosages. Then the animals or animal cells are examined for alteration in amyloid protein or amyloid precursor protein processing, expression levels, or localization of other Alzheimer's disease or other amyloid disease markers, and/or histopathology. In the case of animals utilized for Alzheimer's disease, behavior tests are implemented utilizing standard known memory tests known to those skilled in the art. In general, any improvement in behavioral tests, alteration in Alzheimer's disease-associated markers, reduction in the severity of Alzheimer's disease-related histopathology, reduction in the expression of Aβ or βPP cleavage products, and/or changes in the presence, absence or levels or other compounds that are correlated with Alzheimer's disease which are observed in treated animals, relative to untreated animals, is indicative of a compound useful for treating Alzheimer's disease. The specific proteins, and/or histopathology of those proteins, that are associated with and characteristic of Alzheimer's disease are referred to herein as markers. Expression or localization of these markers characteristic of Alzheimer's disease has either been detected, or is expected to be present, in the disclosed transgenic animals. These markers can be measured or detected, and those measurements compared between treated and untreated transgenic animals to determine the effect of a tested compound.

Markers useful for Alzheimer's disease screening assays are selected based on detectable changes in these markers that are associated with Alzheimer's disease. Many such markers have been identified in Alzheimer's disease and are expected to be present in the isclosed animals. These markers fall into several categories based on their nature, location or function. Preferred examples of markers useful in Alzheimer's disease screening assays are described below, grouped as Aβ-related markers, plaque-related markers, cytoskeletal and neuritic markers, inflammatory markers, and neuronal and neurotransmitter-related markers.

A. Aβ-Related Markers

Expression of the various forms of βPP and Aβ can be directly measured in treated and untreated transgenic animals both by immunocytochemistry and by quantitative ELISA measurements. Currently, it is known that two forms of βPP products are found, βPP and Aβ (Haass and Selkoe, *Cell* 75:1039–1042 (1993)). They have been shown to be intrinsically associated with the pathology of Alzheimer's disease in a time dependent manner. Therefore, preferred assays compare age-related changes in βPP and Aβ expression in the transgenic mice. Generally, specific forms of Aβ can be assayed, either quantitatively or qualitatively using specific antibodies. When referring to amino acid positions in forms of Aβ, the positions correspond to the Aβ region of βPP. Amino acid 1 of Aβ corresponds to amino acid 672 of βPP, and amino acid 42 of Aβ corresponds to amino acid 714 of βPP.

Also preferred as targets for assay measurement are βPP markers. For example, different forms of secreted βPP (termed βPP-alpha and βPP-β) can also be measured (Seubert et al., *Nature* 361:260–263 (1993)). βPP forms are also preferred targets for assays to assess the potential for compounds to affect Alzheimer's disease. The absolute level of βPP and βPP transcripts, the relative levels of the different βPP forms and their cleavage products, and localization of βPP expression or processing are all markers associated with Alzheimer's disease that can be used to measure the effect of treatment with potential therapeutic compounds. The localization of βPP to plaques and neuritic tissue is an especially preferred target for these assays.

Quantitative measurement can be accomplished using many standard assays. For example, transcript levels can be measured using RT-PCR and hybridization methods including RNase protection assays, Northern blot analysis, and R-dot analysis. βPP and Aβ levels can be assayed by ELISA, Western blot analysis, and be comparison of immunohistochemically stained tissue sections. Immunohistochemical staining can also be used to assay localization of βPP and Aβ to particular tissues and cell types.

B. Plaque-Related Markers

A variety of other molecules are also present in plaques of individuals with Alzheimer's disease, and their presence in plaques and neuritic tissue can be detected. Preferred plaque markers are tau protein (Grundke-Iqbal et al., *Proc. Natl. Acad. Sci. USA* 83:4913–4917 (1986); Kosik et al., *Proc. Natl. Acad. Sci.* 83:4044–4048 (1986); Lee et al., *Science* 251:675–678 (1991)), apolipoprotein E (Corder et al., *Science* 261:921–923 (1993); Strittmatter et al., *Proc. Natl. Acad. Sci. USA* 90:8098–8102 (1993)), alpha$_1$-antichymotrypsin (Abraham et al., *Cell* 52:487–501 (1988)), amyloid P component (Coria et al., *Lab. Invest.* 58:454–458 (1988)), ubiquitin (Mori et al., *Science* 235:1641–1644 (1987)), cytokines (McGeer et al., *Can. J. Neurol. Sci.* 16:516–527 (19B9); reviewed in *Rogers, CNS Drugs* 4:241–244 (1994)), growth factors (Hefti and Weiner, *Ann. Neurol.* 20:275–281 (1986); Hefti et al., *Neurobiol. Aging* 10:515–533 (1989); Kato et al., *Neurosc.* 122:33–36 (1991); Tooyama et al., *Neurosc. Lett.* 121:155–158 (1991))), complement factors (Eikenbloom et al., *Virch. Arch. B Cell Pathol.* 56:259–262 (1989)), advanced glycosylation end products (Smith et al., *Proc. Natl. Acad. Sci. USA* 91:5710 (1994)), receptor for advanced glycosylation products, growth inhibitory factor, as well as heparan sulfate PGs (Snow et al., *Am. J. Path.* 133:456–463 (1988)), chondroitin sulfate PGs (DeWitt et al., *Exp. Neurol.* 121:149–152 (1993)), dermatan sulfate PGs (Snow et al., *J. Histochem. Cytochem.* 40:105–113 (1992)) and keratan sulfate PGs (Snow et al., *Exp. Neurol.* 138:305–317 (1996)). While the above markers can be used to detect specific components of plaques and neuritic tissue, the location and extent of plaques can also be determined by using well known histochemical stains, such as Congo red and Thioflavin S.

C. Cytoskeletal and Neuritic Markers

Changes in cytoskeletal markers can also be used in Alzheimer's disease screening assays to determine the effect of compounds on Alzheimer's disease. Many of the changes in cytoskeletal markers occur in the neurofibrillary tangles or dystrophic neurites associated with plaques. The following are preferred cytoskeletal and neuritic markers that exhibit changes in and/or an association with Alzheimer's disease. These markers can be detected, and changes can be determined, to measure the effect of compounds on the disclosed transgenic animals, or transgenic animals formed by mating with the disclosed animals. Spectrin exhibits increased breakdown in Alzheimer's disease. Tau and neurofilaments display an increase in hyperphosphorylation in Alzheimer's disease, and levels of ubiquitin increase in Alzheimer's. Tau protein, ubiquitin, MAP-2, neurofilaments, heparan sulfate PGs, dermatan sulfate PGs, chondroitin sulfate GAGs and keratan sulfate PGs are localized to plaques and neuritic tissues in Alzheimer's disease and in general change from their normal localization. GAP43 levels are decreased in the hippocampus in Alzheimer's disease.

D. Inflammatory Markers

Alzheimer's disease is also known to stimulate an inflammatory response, with a corresponding increase in inflammatory markers (McGeer et al., *Can. J. Neurol. Sci.* 16:516–527 (1989); Rogers, *CNS Drugs* 4:241–244 (1994)). The following are preferred inflammatory markers that exhibit changes in and/or an association with Alzheimer's disease. Detection of changes in these markers are useful in Alzheimer's disease screening assays. Acute phase proteins and glial markers such as alpha1-antitrypsin, C-reactive protein, alpha2-macroglobulin (Tooyama et al., *Molecular and Chem. Neuropath.* 18:153–160 (1993)), glial fibrillary acidic protein, Mac-1, F4/80, and cytokines, such as interleukin-1alpha and β, TNF-alpha, interleukin-8, MIP-1alpha (Kim et al., *J. Neuroimmunology* 56:127–134 (1995)), MCP-1 (Kim et al., *J. Neurol. Sci.* 128:28–35 (1995); *J. Neuroimmunol.* 56:127–134 (1995)) and interleukin-6, all increase in Alzheimer's disease and are expected to increase in the disclosed animals. Complement markers such as C3d, C1q, C5, C4d, C4bp, and C5a-C9 are localized in plaques and neuritic tissue. Major histocompatibility complex (MHC) glycoproteins, such as HLA-DR and HLA-A, HLA-D,HLA-C increase in Alzheimer's disease. Microglial markers, such as CR3 receptor, MHCI, MHCII, CD31, CD11a, CD11b, CD11c, CD68, CD45RO, CD45RO, CD45RD, CD18, CD59, CR4, CD4S, CD64, and CD44 (Akiyama et al., *Br. Res.* 632:249–259 (1993)) increase in Alzheimer's disease. Additional inflammatory markers useful in Alzheimer's disease screening assays include alpha2-macroglobulin receptor, fibroblast growth factor (Tooyama et al., *Neurosc. Letts.* 121:155–158 (1991)), ICAM-1 (Akiyama et al., *Acta Neuropath.* 85:628–634 (1993)), lactotransferrin (Kawamata et al., *Am. J. Path.* 142:1574–1585 (1993)), C1q, C3d, C4d, C5b-9, Fc gamma RII, CD8 (McGeer et al., *Can. J. Neurol. Sc.* 16:516–527 (1989)), LCA (CD45)(Akiyama et al., *J. Neuroimmunol.* 50:195–201 (1994)), CD18 (beta-2 integrin)(Akiyama and McGeer, *J. Neuroimmunology* 30:81–93 (1990)), CD59 (McGeer et al., *Br. Res.* 544:315–319 (1991)), vitronectic (McGeer et al., *Can. J. Neurol. Sci.* 18:376–379 (1991)), vitronectin receptor, beta-3 integrin, Apo J, clusterin (McGeer et al., *Br. Res.* 579:337–341 (1992)), type 2 plasminogen activator inhibitor (Akiyama et al., *Neurosc. Lett.* 164:233–235 (1993)), CD44 (Akiyama et al., *Br. Res.* 633:249–259 (1993)), midkine (Yasuhara et al., *Biochem. Biophys. Res. Comm.* 192:246–251 (1993)), macrophage colony stimulating factor receptor (Akiyama et al., *Br. Res.* 639:171–174 (1994)), MRP14, 27E10, and interferon-alpha (Akiyama et al., *J. Neuroimmunol.* 50:195–201 (1994)). Additional markers which are associated with inflammation or oxidative stress include 4-hydroxynonenal-protein conjugates (Uchida and Stadtman, *Meth. Enz.* 233:371–380 (1994)), IkappaB, NFkappaB (Kaltschmidt et al., *Mol. Aspects. Med.* 14:171–190 (1993)), cPLA$_2$ (Stephenson et al., *Neurobiol. Dis.* 3:51–63 (1996)), COX-2 (Chen et al., *Neuroreport* 6:245–248 (1995)), matrix metalloproteinases (Backstrom et al., *J. Neurochem.* 58:983–992 (1992)), membrane lipid peroxidation, protein oxidation (Smith et al., *Proc. Natl. Acad. Sci. USA* 88:10540–10543 (1991)) and diminished ATPase activity (Mark et al., *J. Neurosc.* 15:6239 (1995)). These markers can be detected, and changes can be determined to measure an effect of compounds on the disclosed transgenic animals.

E. Neuronal and Neurotransmitter-Related Markers

Changes in neuronal and neurotransmitter biochemistry have been associated with Alzheimer's disease. In Alzheimer's, there is profound reduction in cortical and hippocampal cholinergic innervation. This is evidenced by the dramatic loss of the synthetic enzyme choline acetyltransferase and decreased acetylcholinesterase, synaptosomal choline uptake and synthesis and release of acetylcholine (Sims et al., *J. Neurochem.* 40:503–509 (1983)), all of which are useful markers.These markers can be used in Alzheimer's disease screening assays to determine the effect of compounds on Alzheimer's disease. There is also a loss of basal forebrain neurons and the galanin system becomes hypertrophic in Alzheimer's disease.

In addition to changes in the markers described above in Alzheimer's disease, there is also atrophy and loss of basal forebrain cholinergic neurons that project to the cortex and hippocampus (Whitehouse et al., *Science* 215:1237–1239 (1982)), as well as alterations of entorhinal cortex neurons (Van Hoesan et al., *Hippocampus* 1:1–8 (1991)). Based upon these observations measurement of these enzyme activities, neuronal size, and neuronal count numbers are expected to decrease in the disclosed transgenic animals and are therefore useful targets for detection in Alzheimer's disease screening assays. Basal forebrain neurons are dependent on nerve growth factor. Brain-derived neurotrophic factor (BDNF) may also decrease in the hippocampus and is therefore a useful target for detection in Alzheimer's disease screening assays. In addition, screening assays that measure the effect of compounds on neurotransmitter receptors can possibly be used to identifying compounds useful in treating Alzheimer's disease.

In addition to the well-documented changes in the cholinergic system, dysfunction in other receptor systems such as the serotinergic, adrenergic, adenosine and nicotine receptor systems, has also been documented. Markers characteristic of these changes, as well as other neuronal markers that exhibit both metabolic and structural changes in Alzheimer's disease are listed below. Changes in the level and/or localization of these markers can be measured using similar techniques as those described for measuring and detecting the earlier markers.

The following are preferred cytoskeletal and neuritic markers that exhibit changes in and/or an association with Alzheimer's disease. Levels of cathepsin D, cathepsin B, cathepsin G, and neuronal thread protein, and phosphorylation of elongation factor-2, increase in Alzheimer's. Cathepsin D, cathepsin B, protein kinase C and NADPH are localized in plaque and neuritic tissue in Alzheimer's disease. Activity and/or levels of nicotine receptors, 5-HT$_2$ receptor, NMDA receptor, alpha2-adrenergic receptor, synaptophysin, synaptoglycan (SV2PG), p65, glutamine synthetase, glucose transporter, PPI kinase, drebrin, GAP43, cytochrome oxidase, heme oxygenase, calbindin, adenosine A1 receptors, mono amine metabolites, choline acetyltransferase, acetylcholinesterase, and symptosomal choline are all reduced in Alzheimer's disease.

Additional markers that are associated with Alzheimer's disease or after treatment of cells with Aβ include a) cPLA$_2$ which is upregulated in Alzheimer's disease (Stephenson et al., *Neurobiol. Dis.* 3:51–63 (1996)), b) heme oxygenase-1 (Smith et al., *Am. J. Path.* 145:42–47 (1994)), c-jun (Anderson et al., *Exp. Neurol.* 125:286–295 (1994)), c-fos (Zhang et al., *Neurosci.* 46:9–21 (1992)), HSP27 (Renkawek et al., *Acta Neuropath.* 87:511–519 (1994)), HSP70 (Cisse et al., *Acta Neuropath.* 85:233–240 (1993)) and MAP5 (Geddes et al., *J. Neurosc. Res.* 30:183–191 (1991)), which are induced in Alzheimer's disease and in cortical cells after Aβ treatment and c) junB, junD, fosB, fral (Estus et al., *J. Cell Biol.* 127:1717–1727 (1994)), cyclin D1 (Freeman et al., *Neuron* 12:343–355 (1994)), NGFI-A (Vaccarino et al., *Mol. Br. Res.* 12:233–241 (1992)), and NGFI-B, which are induced in cortical cells after Aβ treatment.

F. Measuring the Amounts and Localization of Alzheimer's Disease Markers

Quantitative measurements can be accomplished using many standard assays. For example, transcript levels can be measured using RT-PCR and hybridization methods including RNase protection, Northern analysis, and R-dot analysis.

Protein marker levels can be assayed by ELISA, Western analysis, and by comparison of immunohistochemically stained tissue sections. Immunohistochemical staining can also be used to assay localization of protein markers to particular tissues and cell types. The localization and the histopathological association of Alzheimer's disease markers can be determined by histochemical detection methods such as antibody staining, laser scanning confocal imaging, and electron and immunoelectron microscopy.

In the case of receptors and enzymatic markers, activity of the receptors or enzymes can be measured. For example, the activity of neurotransmitter metabolizing enzymes such as choline acetyltransferase and acetylcholine esterase can be measured using standard radiometric enzyme activity assays.

G. Screening Assays Using Cultured Cells

Screening assays for determining the therapeutic potential of compounds can also be performed using cells derived from animals transgenic for the disclosed perlecan constructs or cell cultures stably transfected with the disclosed constructs, or from cells derived from progeny derived from the mating of perlecan transgenic mice with other transgenics implicated in Alzheimer's disease. For example, P19 cells which overproduce perlecan also demonstrate a marked increase in A$\beta$ levels in the media. In a preferred embodiment, a potential therapeutic compound for Alzheimer's disease is tested on perlecan transfected P19 cells, or other cells types that also demonstrate increased A$\beta$ production due to perlecan transfection. For such testing, derived transgenic cells or transfected cell cultures, following an overnight incubation at 37° C. in an incubator equilibrated with 5% carbon dioxide, will have the media removed and replaced with media containing a compound to be tested for a 2 hour pretreatment period with the cells then incubated as above. At the end of the pretreatment period, the media are again removed and replaced with fresh media containing the compound to be tested (as described above) and cells are incubated for an additional 2 to 16 hours. After treatment, plates are centrifuged in a Beckman GPR at 1200 rpm for 5 minutes at room temperature to pellet cellular debris from the conditioned media. From each well, 100 $\mu$l of conditioned media or appropriate dilutions thereof are transferred into an ELISA plate precoated with antibody 266 (an antibody directed against amino acids 13 to 28 of A$\beta$) as described in International patent Application No. 94/10569 and stored at 4° C. overnight. An ELISA assay employing any labelled antibody against A$\beta$ (such as 4G8 from Senetek) can be run to measure the amount of A$\beta$ produced. Different capture and detection antibodies can also be used. In addition, various cytotoxicity assays, such as the MTS assay described in Example 6 of the disclosed invention, can be utilized to determine whether the compound protect cells from neurodegeneration or neuronal death.

H. Screening for Compounds Effective in Other Amyloid Diseases

Use of the perlecan transgenic mice, transfected cells, or cells derived from transgenic mice as disclosed in the present invention, can be used either alone or in combination with other transgenic mice, transfected cells, or cells derived from other transgenic mice implicated.in a given amyloid disease, to produce new animal and cell culture models of amyloid diseases (other than the Alzheimer's-type of amyloid disease). For example, the mating of perlecan mice with transgenic animals which overproduce islet amyloid (amylin) may produce progeny which exhibit a new animal model completely mimicking islet amyloid deposition in pancreas. In such transgenic animals amyloid formation, deposition, accumulation and/or persistence of an amyloid protein (other than the Alzheimer's disease A$\beta$) is occurring in peripheral tissues, making these animals useful for the screening of anti-amyloid compounds to determine if said compounds affect or diminish accumulation of a specific amyloid protein in the tissues. Initial analysis may include, but is not limited to, detecting levels and immunolocalization of a given amyloid protein using specific anti-amyloid antibodies which are commercially available including those against AA amyloid, AL amyloid, islet amyloid (i.e. amylin), beta$_2$-microglobulin, transthyretin/prealbumin, procalcitonin, and PrP amyloid (brain amyloidosis), and comparison of compound-treated versus placebo-treated animals. In addition, qualitative and quantitative assessment of the extent of amyloid can be made following detection by specific amyloid stains such as Congo red (and viewed under polarized light) or Thioflavin S (viewed under fluorescent light). In such assessments, a given compound is administered to an animal at various dosages, for various treatment periods, and at varying stages of amyloid formation, deposition accumulation and persistence in tissues. A given compound is said to be effective by reducing or eliminating the amyloid by a correlative decrease or elimination of amyloid protein immunostaining, Congo red staining (as viewed under polarized light) or Thioflavin T fluorescence. In addition, electron microscopic analysis can be used for the detection and localization of amyloid fibrils in a given tissue, and qualitative and quantitative assessments can be made prior-to and following compound treatments in groups of animals. In all of the screening assays described above, the effective compounds will be the ones which diminish or eliminate amyloid in a particular tissue or animal.

New Amyloid Disease Models

The strategy of crossing perlecan transgenic mice with transgenic mice that overexpress any other amyloid protein, or another component implicated in a given amyloid disease, will also produce new animal models of different amyloidoses which can be utilized as screening tools to identify new therapeutics for the treatment of amyloidoses.

In one preferred embodiment, perlecan transgenic mice mated with transgenic mice overexpressing any isoform of beta-amyloid precursor protein (and/or its portions thereof) produce transgenic progeny that overexpress both perlecan and $\beta$PP. This new transgenic animal model can be used as a screening tool to identify potential therapeutics targeting A$\beta$ amyloidosis as observed in Alzheimer's disease, Down's syndrome and cerebral hemorrhage with amyloidosis of the Dutch type.

In another preferred embodiment, perlecan transgenic mice are mated with transgenic mice wherein the A$\beta$-containing protein consists of all or a contiguous portion of a protein selected from a group consisting of $\beta$PP-770, $\beta$PP-770 bearing a mutation in one or more of the amino acids selected from the group consisting of amino acids 669, 670, 671, 690, 692 and 717, $\beta$PP-751, $\beta$PP-751 bearing a mutation in one or more of the amino acids selected from the group consisting of amino acid 669, 670, 671, 690, 692 and 717, $\beta$PP-695, and $\beta$PP-695 bearing a mutation in one or more of the amino acids selected from the group consisting of amino acid 669, 670, 671, 690, 692 and 717, wherein the A$\beta$-containing protein includes amino acids 672 to 714 of human $\beta$PP.

In another preferred embodiment, perlecan transgenic mice are mated with transgenic mice which overexpress presenilin 1, presenilin 2, or transgenics which contain mutations to either presenilin 1 or presenilin 2.

In another preferred embodiment, perlecan transgenic mice are mated with transgenic mice which overexpress a protein selected from the group consisting of laminin, type IV collagen, heparan sulfate PGs, chondroitin sulfate PGs, dermatan sulfate PGs, keratan sulfate PGs, glypican, syndecan, syndecan-3, neurocan, phosphacan, aggrecan, decorin, biglycan, hyaluronan, amyloid P component, alpha$_1$-antichymotrypsin, cathepsin D, cathepsin G, cathepsin B, neuronal thread protein, nicotine receptors, 5-HT$_2$ receptor, NMDA receptor, alpha2-adrenergic receptor, synaptophysin, p65, glutamine synthetase, glucose transporter, PPI kinase, GAP43, cytochrome kinase, heme oxygenase, calbindin, adenosine A1 receptors, choline acetyltransferase, acetylcholinesterase, glial fibrillary acidic protein, alpha1-antitrypsin, C-reactive protein, alpha2-macroglobulin, interleukin-1alpha, interleukin-1β, TNF-alpha, interleukin-6, HLA-DR, HLA-A, HLA-D, HLA-C, CR3 receptor, MHC I, MHC II, CD 31, CR4, CD45, CD64, CD4, spectrin, tau protein, ubiguitin, MAP-2, apolipoprotein E, apolipoprotein E4, apolipoprotein E2, apolipoprotein E3, nerve growth factor, brain-derived neurotrophic factor, advanced glycosylation end products, receptor for advanced glycosylation end products, COX-2, CD18, C3, fibroblast growth factor, CD44, ICAM-1, lactotransferrin, C1q, C3d, C4d, C5b-9, gamma R1, Fc gamma RII, CD8, CD59, vitronectin, vitronectin receptor, beta-3 integrin, Apo J, clusterin, type 2 plasminogen activator inhibitor, midline, macrophage colony stimulating factor receptor, MRP14, 27E10, interferon-alpha, S100β, cPLA$_2$, c-jun, c-fos, HSP27, HSP70, MAP5, membrane lipid peroxidase, protein carbonyl formation, junB, junD, fosB, fral, cyclin D1, p53, NGFI-A, NGFI-B, I-kappa-B, NF-kappa-B, interleukin-8, MCP-1, MIP-1alpha, matrix metaloproteinases, and 4-hydroxynonenal-protein conjugates.

In another preferred embodiment, perlecan transgenic mice mated with transgenic mice overexpressing AL amyloid (and/or its portions thereof) produce transgenic progeny that overexpress both perlecan and AL amyloid. This new transgenic animal model can be used as a screening tool to identify potential therapeutics targeting AL amyloidosis as observed in multiple myeloma and other β-cell dyscrasias.

In another preferred embodiment, perlecan transgenic mice mated with transgenic mice overexpressing islet amyloid (amylin) produce transgenic progeny that overexpress both perlecan and amylin. This new transgenic animal model can be used as a screening tool to identify potential therapeutics targeting islet amyloidosis as observed in type II diabetes.

In another preferred embodiment, perlecan transgenic mice mated with transgenic mice overexpressing PrP amyloid produce transgenic progeny that overexpress both perlecan and PrP protein. This new transgenic animal model can be used as a screening tool to identify potential therapeutics targeting PrP amyloidosis as observed in Creutzfeldt-Jakob disease, Gerstmann-Straussler syndrome, kuru and animal scrapie.

In yet another preferred embodiment, perlecan transgenic mice mated with transgenic mice overexpressing beta$_2$-microglobulin produce transgenic progeny that overexpress both perlecan and beta$_2$-microglobulin. This new transgenic animal model can be used as a screening tool to identify potential therapeutics targeting beta$_2$-microglobulin amyloidosis as observed in long-term hemodialysis and carpal tunnel syndrome.

In another preferred embodiment, perlecan transgenic mice mated with transgenic mice overexpressing prealbumin/transthyretin produce transgenic progeny that overexpress both perlecan and prealbumin/transthyretin. This new transgenic animal model can be used as a screening tool to identify potential therapeutics targeting prealbumin/transthyretin amyloidosis as observed in senile cardiac amyloid and Familial Amyloidotic Polyneuropathy.

In yet another preferred embodiment, perlecan transgenic mice mated with transgenic mice overexpressing variants of procalcitonin produce transgenic progeny that overexpress both perlecan and variants of procalcitonin. This new transgenic animal model can be used as a screening tool to identify potential therapeutics targeting the amyloid associated with endocrine tumors such as in medullary carcinoma of the thyroid.

In yet another preferred embodiment, perlecan transgenic mice are mated with "knock-out" transgenic mice which do not express, or express at much reduced levels than normal, a given amyloid protein or protein implicated to be important in amyloid disease as listed above. These new transgenic animal models can be used as a screening tool to identify potential therapeutics targeting various amyloid diseases.

In yet another preferred embodiment, transgenic mice that overexpress both perlecan and any amyloid protein, (amyloid precursor protein and/or a fragment thereof), is produced by injection of both perlecan and amyloid protein DNA constructs into fertilized mouse eggs (one cell stage embryos). The embryos bearing both the DNA constructs are transferred to the oviducts of pseudopregnant foster mothers. The tails from the emerging pups are cut for Southern blot analysis or PCR to determine the chromosomal integration of both the transgenes. Pups determined positive for both the transgenes are crossed with other mice (example: C57BL/6J) to establish lines of transgenic mice bearing both the DNA constructs.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What we claim is:

1. A transgenic mouse whose genome comprises a transgene encoding a mouse perlecan domains I–V, wherein the transgene is operatively linked to a chick B-actin promoter and a cytomegalovirus (CMV) enhancer, whereby expression of the transgene results in over expression of mouse perlecan, as compared to a non-transgenic mouse.

2. A transgenic mouse whose somatic and germ cells comprise a transgene encoding mouse perlecan domains I–V, wherein the transgene is operatively linked to a chick B-actin promoter and a cytomegalovirus (CMV) enhancer, wherein the expression of the transgene results in over expression of the mouse perlecan in all cells, as compared to non-transgenic cells.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 28 NUCLEOTIDES
      (B) TYPE: NUCLEIC ACIDS (C) STRANDEDNESS: SINGLE
                (D) TOPOLOGY: LINEAR (ii) MOLECULE TYPE: OLIGONUCLEOTIDE PRIMERS (xi) SEQUENCE DESCRIPTION: SEQ ID NO:1:

CCCTCGAGAA GCTTCTTAAG GTCGACGG                                               28

(2) INFORMATION FOR SEQ ID NO:2:

(i) SEQUENCE CHARACTERISTICS:
                (A) LENGTH: 28 NUCLEOTIDES
                (B) TYPE: NUCLEIC ACIDS
                (C) STRANDEDNESS: SINGLE
                (D) TOPOLOGY: LINEAR (ii) MOLECULE TYPE: OLIGONUCLEOTIDE PRIMERS (xi) SEQUENCE DESCRIPTION: SEQ ID NO:2:

CCGTCGACCT TAAGAAGCTT CTCGAGGG                                               28

(2) INFORMATION FOR SEQ ID NO:3:

(i) SEQUENCE CHARACTERISTICS:
                (A) LENGTH: 26 NUCLEOTIDES
                (B) TYPE: NUCLEIC ACIDS
                (C) STRANDEDNESS: SINGLE
                (D) TOPOLOGY: LINEAR (ii) MOLECULE TYPE: OLIGONUCLEOTIDE PRIMERS (xi) SEQUENCE DESCRIPTION: SEQ ID NO:3:

GCATTAATCA GCTAGCACTT CGAACG                                                 26

(2) INFORMATION FOR SEQ ID NO:4:

(i) SEQUENCE CHARACTERISTICS:
                (A) LENGTH: 26 NUCLEOTIDES
                (B) TYPE: NUCLEIC ACIDS
                (C) STRANDEDNESS: SINGLE
                (D) TOPOLOGY: LINEAR (ii) MOLECULE TYPE: OLIGONUCLEOTIDE PRIMERS (xi) SEQUENCE DESCRIPTION: SEQ ID NO:4:

CGTTCGAAGT GCTAGCTGAT TAATGC                                                 26

(2) INFORMATION FOR SEQ ID NO:5:

(i) SEQUENCE CHARACTERISTICS:
                (A) LENGTH: 40 NUCLEOTIDES
                (B) TYPE: NUCLEIC ACIDS
                (C) STRANDEDNESS: SINGLE
                (D) TOPOLOGY: LINEAR (ii) MOLECULE TYPE: OLIGONUCLEOTIDE PRIMERS (xi) SEQUENCE DESCRIPTION: SEQ ID NO:5:

GATCCGCGAT GCTGCCCGGT TTGGCACTGC TCCTGCTGGC                                  40

(2) INFORMATION FOR SEQ ID NO:6:

(i) SEQUENCE CHARACTERISTICS:
                (A) LENGTH: 40 NUCLEOTIDES
                (B) TYPE: NUCLEIC ACIDS
                (C) STRANDEDNESS: SINGLE
                (D) TOPOLOGY: LINEAR (ii) MOLECULE TYPE: OLIGONUCLEOTIDE PRIMERS

-continued (xi) SEQUENCE DESCRIPTION: SEQ ID NO:6:

AGCGGCCAGC AGGAGCAGTG CCAAACCGGG CAGCATCGCG          40

(2) INFORMATION FOR SEQ ID NO:7:

(i) SEQUENCE CHARACTERISTICS:
       (A) LENGTH: 26 NUCLEOTIDES
       (B) TYPE: NUCLEIC ACIDS
       (C) STRANDEDNESS: SINGLE
       (D) TOPOLOGY: LINEAR (ii) MOLECULE TYPE: OLIGONUCLEOTIDE PRIMERS (xi) SEQUENCE DESCRIPTION: SEQ ID NO:7:

CGCCTGGACG GCTCGGGCGG ATGCAG                         26

(2) INFORMATION FOR SEQ ID NO:8:

(i) SEQUENCE CHARACTERISTICS:
       (A) LENGTH: 25 NUCLEOTIDES
       (B) TYPE: NUCLEIC ACIDS
       (C) STRANDEDNESS: SINGLE
       (D) TOPOLOGY: LINEAR (ii) MOLECULE TYPE: OLIGONUCLEOTIDE PRIMERS (xi) SEQUENCE DESCRIPTION: SEQ ID NO:8:

AATTCTGCAT CCGCCCGAGC CGTCC                          25

(2) INFORMATION FOR SEQ ID NO:9:

(i) SEQUENCE CHARACTERISTICS:
       (A) LENGTH: 13 AMINO ACIDS
       (B) TYPE: AMINO ACIDS
       (C) STRANDEDNESS: SINGLE
       (D) TOPOLOGY: LINEAR (xi) SEQUENCE DESCRIPTION: SEQ ID NO:9:

Met Leu Pro Gly Leu Ala Leu Leu Leu Cys Ala Trp
1               5                   10

(2) INFORMATION FOR SEQ ID NO:10:

(i) SEQUENCE CHARACTERISTICS:
       (A) LENGTH: 7 AMINO ACIDS
       (B) TYPE: AMINO ACIDS
       (C) STRANDEDNESS: SINGLE
       (D) TOPOLOGY: LINEAR (xi) SEQUENCE DESCRIPTION: SEQ ID NO:10:

Thr Ala Arg Ala Asp Ala Glu
1               5